(12) United States Patent
Deck et al.

(10) Patent No.: US 12,144,502 B2
(45) Date of Patent: Nov. 19, 2024

(54) FIRING SYSTEM FOR LINEAR SURGICAL STAPLER

(71) Applicant: Cilag GmbH International, Zug (CH)

(72) Inventors: Andrew C. Deck, Cincinnati, OH (US);
Jason Jones, Cincinnati, OH (US);
Gregory J. Bakos, Mason, OH (US);
Brian D. Schings, Maineville, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/454,168

(22) Filed: Aug. 23, 2023

(65) Prior Publication Data

US 2023/0397910 A1    Dec. 14, 2023

Related U.S. Application Data

(63) Continuation of application No. 17/090,382, filed on Nov. 5, 2020, now Pat. No. 11,786,242, which is a
(Continued)

(51) Int. Cl.
*A61B 17/072*    (2006.01)
*A61B 17/00*    (2006.01)
(Continued)

(52) U.S. Cl.
CPC ...... *A61B 17/072* (2013.01); *A61B 17/07207* (2013.01); *A61B 2017/00477* (2013.01);
(Continued)

(58) Field of Classification Search
CPC .............. A61B 17/068; A61B 17/072; A61B 17/07207; A61B 17/115; A61B 17/2833;
(Continued)

(56) References Cited

U.S. PATENT DOCUMENTS

| | | |
|---|---|---|
| 4,520,817 A | 6/1985 | Green |
| 4,863,088 A | 9/1989 | Redmond et al. |
| | (Continued) | |

FOREIGN PATENT DOCUMENTS

| | | |
|---|---|---|
| CN | 202875415 U | 4/2013 |
| EP | 0061466 A1 | 10/1982 |
| | (Continued) | |

OTHER PUBLICATIONS

European Search Report, Extended, and Written Opinion dated Dec. 2, 2019, for Application No. 19191312.8, 12 pages.
(Continued)

*Primary Examiner* — Scott A Smith
(74) *Attorney, Agent, or Firm* — Frost Brown Todd LLP

(57) ABSTRACT

A surgical stapler includes a first elongate member, a second elongate member, and a clamp member operable to releasably clamp the first elongate member against the second elongate member. A distal portion of the first elongate member supports an anvil surface having a plurality of staple forming pockets. A distal portion of the second elongate member is configured to receive a staple cartridge. A firing assembly of the surgical stapler is translatable from a first longitudinal position to a second longitudinal position to fire the staple cartridge when the first elongate member is clamped against the second elongate member. A retaining assembly of the surgical stapler includes a first retaining member configured to releasably couple a proximal end of the first elongate member with a proximal end of the second elongate member, and a second retaining member configured to releasably retain the firing assembly in the first longitudinal position.

20 Claims, 35 Drawing Sheets

Related U.S. Application Data continuation of application No. 16/102,164, filed on Aug. 13, 2018, now Pat. No. 10,898,187.

(51) Int. Cl.
  *A61B 17/068* (2006.01)
  *A61B 17/28* (2006.01)
  *A61B 17/29* (2006.01)

(52) U.S. Cl.
  CPC ... *A61B 2017/00862* (2013.01); *A61B 17/068* (2013.01); *A61B 2017/07214* (2013.01); *A61B 2017/07264* (2013.01); *A61B 2017/07271* (2013.01); *A61B 2017/07278* (2013.01); *A61B 17/2833* (2013.01); *A61B 2017/2927* (2013.01)

(58) Field of Classification Search
  CPC ...... A61B 17/2841; A61B 2017/00477; A61B 2017/07214; A61B 2017/07271; A61B 2017/2927; A61B 2017/2929
  USPC ..... 227/19, 175.1, 175.2, 176.1; 606/1, 139, 606/219
  See application file for complete search history.

(56) References Cited

U.S. PATENT DOCUMENTS

| | | |
|---|---|---|
| 4,991,764 A | 2/1991 | Mericle |
| 5,141,144 A | 8/1992 | Foslien |
| 5,636,779 A | 6/1997 | Palmer |
| 5,792,135 A | 8/1998 | Madhani et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 7,524,320 B2 | 4/2009 | Tierney et al. |
| 7,631,794 B2 | 12/2009 | Rethy et al. |
| 7,691,098 B2 | 4/2010 | Wallace et al. |
| 7,806,891 B2 | 10/2010 | Nowlin et al. |
| 7,905,381 B2 | 3/2011 | Baxter, III et al. |
| 7,954,686 B2 | 6/2011 | Baxter, III et al. |
| 8,348,129 B2 | 1/2013 | Bedi et al. |
| 8,479,969 B2 | 7/2013 | Shelton, IV |
| 8,523,041 B2 | 9/2013 | Ishitsuki et al. |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,789,740 B2 | 7/2014 | Baxter, III et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 9,155,537 B2 | 10/2015 | Katre et al. |
| 9,301,759 B2 | 4/2016 | Spivey et al. |
| 9,402,629 B2 | 8/2016 | Ehrenfels et al. |
| 9,539,007 B2 | 1/2017 | Dhakad et al. |
| 9,724,095 B2 | 8/2017 | Gupta et al. |
| 10,631,866 B2 | 4/2020 | Laurent et al. |
| 10,667,818 B2 | 6/2020 | McLain et al. |
| 10,687,819 B2 | 6/2020 | Stokes et al. |
| 10,874,398 B2 | 12/2020 | Baxter et al. |
| 10,898,187 B2 | 1/2021 | Deck et al. |
| 10,898,197 B2 | 1/2021 | Baxter et al. |
| 10,905,419 B2 | 2/2021 | Schings et al. |
| 10,932,781 B2 | 3/2021 | Jones et al. |
| 11,033,266 B2 | 6/2021 | Jones et al. |
| 11,045,193 B2 | 6/2021 | Schings et al. |
| 11,786,242 B2 * | 10/2023 | Deck ............... A61B 17/07207 227/175.4 |
| 2006/0219752 A1 | 10/2006 | Arad et al. |
| 2009/0173766 A1 | 7/2009 | Wenchell |
| 2009/0308907 A1 | 12/2009 | Nalagatla et al. |
| 2012/0143218 A1 | 6/2012 | Beardsley et al. |
| 2012/0286021 A1 | 11/2012 | Kostrzewski |
| 2012/0312858 A1 | 12/2012 | Patankar et al. |
| 2013/0172929 A1 | 7/2013 | Hess et al. |
| 2014/0353357 A1 | 12/2014 | Agarwal et al. |
| 2015/0018875 A1 | 1/2015 | Knodel |
| 2015/0034695 A1 | 2/2015 | Kapadia |
| 2015/0327855 A1 | 11/2015 | Katre |
| 2016/0135811 A1 | 5/2016 | Gupta et al. |
| 2016/0249920 A1 | 9/2016 | Gupta et al. |
| 2016/0262756 A1 | 9/2016 | Patankar et al. |
| 2016/0310136 A1 | 10/2016 | Gupta et al. |
| 2016/0338701 A1 | 11/2016 | Patankar et al. |
| 2016/0338702 A1 | 11/2016 | Ehrenfels et al. |
| 2017/0079652 A1 | 3/2017 | Dhakad et al. |
| 2017/0143335 A1 | 5/2017 | Gupta et al. |
| 2017/0143336 A1 | 5/2017 | Shah et al. |
| 2017/0325811 A1 | 11/2017 | Gupta et al. |
| 2020/0046353 A1 | 2/2020 | Deck et al. |
| 2021/0113207 A1 | 4/2021 | Deck et al. |

FOREIGN PATENT DOCUMENTS

| | | |
|---|---|---|
| EP | 0178941 B1 | 4/1986 |
| EP | 0677273 B1 | 10/1995 |
| EP | 1702567 B1 | 9/2006 |
| EP | 2018826 A2 | 1/2009 |
| EP | 2532312 B1 | 12/2012 |
| EP | 3065649 A1 | 9/2016 |
| EP | 2741685 B1 | 1/2017 |
| EP | 3155988 A1 | 4/2017 |
| EP | 2804541 B1 | 10/2017 |
| EP | 3289985 A1 | 3/2018 |
| EP | 3520710 A1 | 8/2019 |
| EP | 3520711 A1 | 8/2019 |
| JP | 2013-534159 A | 9/2013 |
| WO | WO 2015/174984 A1 | 11/2015 |
| WO | WO 2017/056028 A1 | 4/2017 |
| WO | WO 2018/044669 A1 | 3/2018 |
| WO | WO 2018/127745 A1 | 7/2018 |

OTHER PUBLICATIONS

European Search Report, Partial, and Provisional Written Opinion dated Jan. 3, 2020, for Application No. 19204124.2, 19 pages.
International Search Report and Written Opinion dated Jul. 7, 2020, for International Application No. PCT/IB2019/058696, 22 pages.
International Search Report and Written Opinion dated Nov. 29, 2019, for International Application No. PCT/IB2019/056697, 16 pages.
Japanese Notification of Reasons for Refusal dated Jun. 6, 2023, for Application No. 2021-507562, 5 pages.
Brazil Office Action dated Jun. 1, 2023, for Application No. BR112021002631-2, 4 pages.
Brazil Office Action dated Jun. 5, 2023, for Application No. BR112021006962-3, 4 pages.
Chinese First Office Action and Search Report dated Nov. 26, 2023, for Application No. 201980068411.5, 9 pages.
European Extended Search Report dated Apr. 6, 2020, for Application No. 19204124.2, 16 pages.
European Extended Search Report dated Jul. 29, 2022, for Application No. 22173560.8, 6 pages.
European Extended Search Report dated Jan. 30, 2024, for Application No. 23207744.6, 6 pages.
Indian Office Action dated Nov. 28, 2022, for Application No. 202117013495, 6 pages.
Japanese Notification of Reasons for Refusal dated Jun. 20, 2023, for Application No. 2021-521277, 5 pages.

* cited by examiner

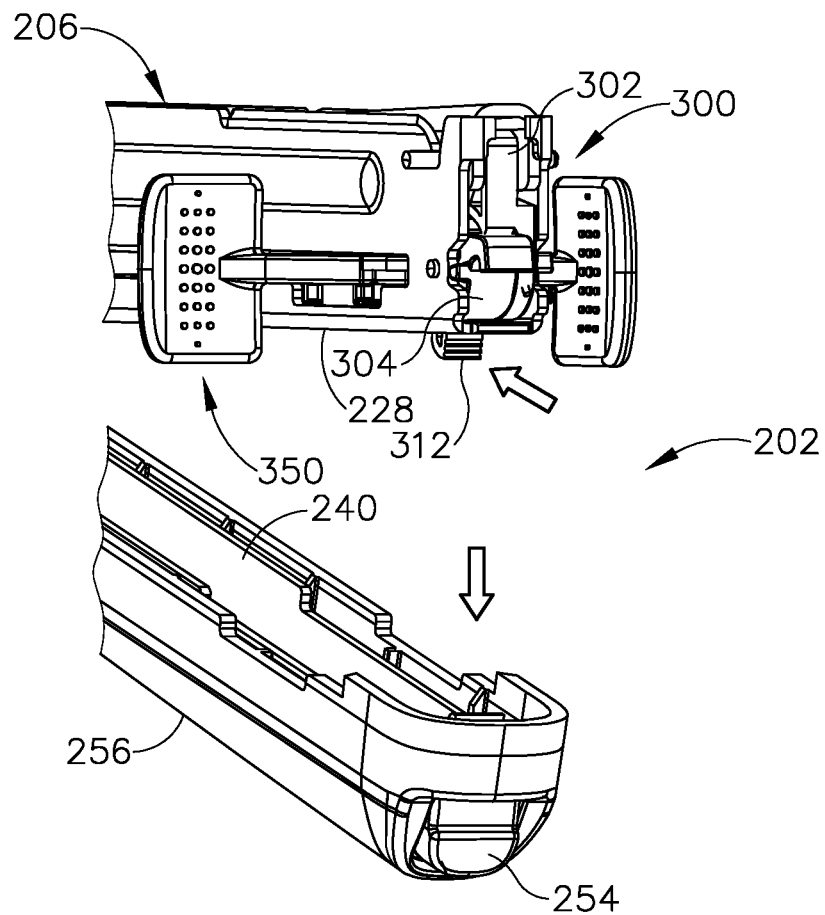
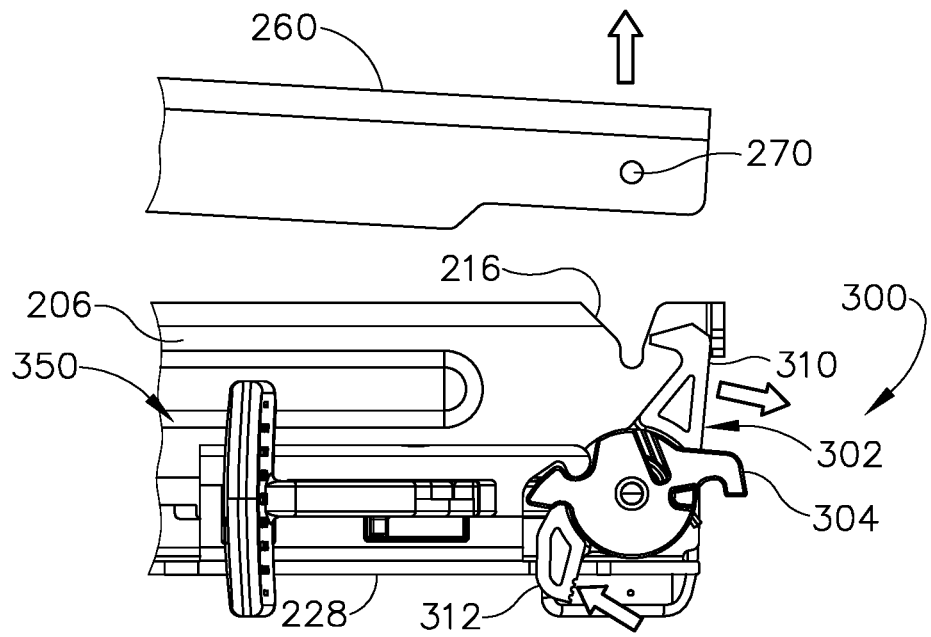
Fig.14A
Fig.14B

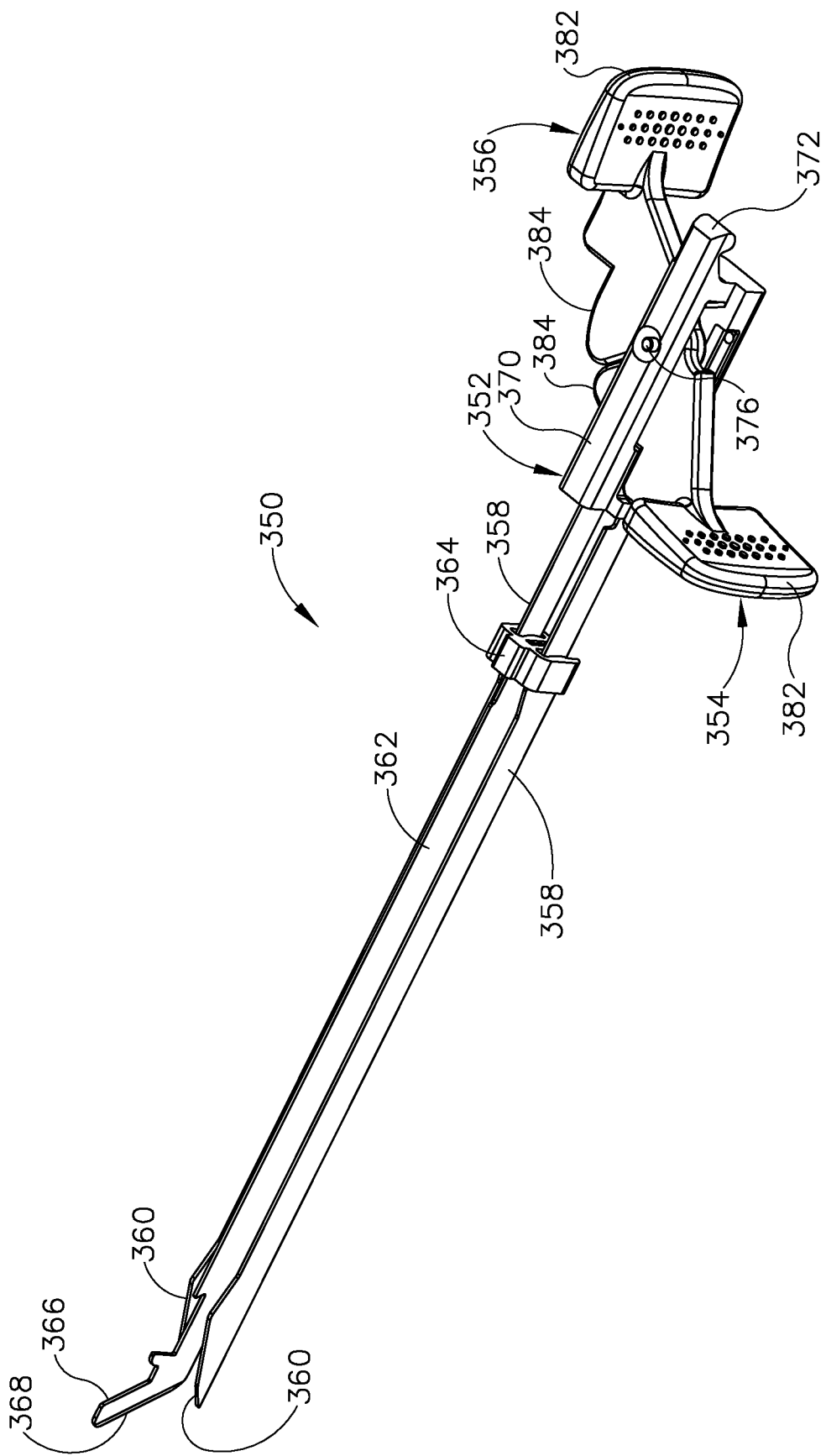

FIRING SYSTEM FOR LINEAR SURGICAL STAPLER

PRIORITY

This application is a continuation of U.S. patent application Ser. No. 17/090,382, entitled "Firing System for Linear Surgical Stapler," filed Nov. 5, 2020, issued as U.S. Pat. No. 11,786,242 on Oct. 17, 2023, which is a continuation of U.S. patent application Ser. No. 16/102,164, entitled "Firing System for Linear Surgical Stapler," filed on Aug. 13, 2018, issued as U.S. Pat. No. 10,898,187 on Jan. 26, 2021.

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 14A depicts a perspective view of a proximal portion of the cartridge half of the linear surgical stapler of FIG. 6, showing the clamp lever in the open position in which a release feature of the anvil latch member is exposed through an underside of the cartridge channel;

FIG. 14B depicts a side elevational view of proximal portions of the stapler halves of FIG. 6 with the anvil shroud omitted and a side portion of the cartridge channel cut away, showing actuation of the release feature to release the proximal anvil pin from the anvil latch member and thereby permit separation of the stapler halves;

FIG. 16 depicts a top perspective view of the firing assembly of the linear surgical stapler of FIG. 6, which includes a slider block and a pair of rotatable actuators;

Figure 1:
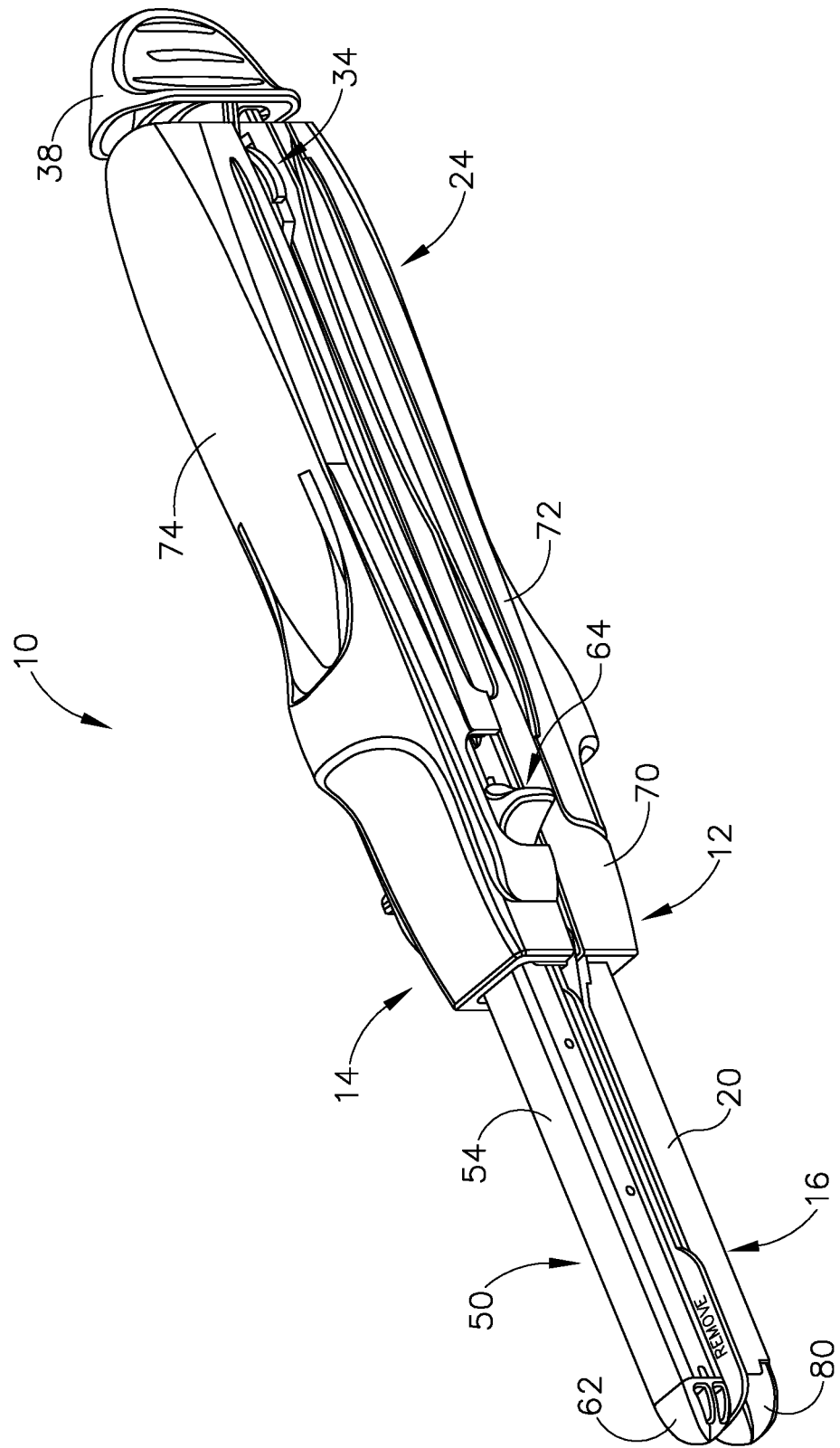
FIG. 1 depicts a distal perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
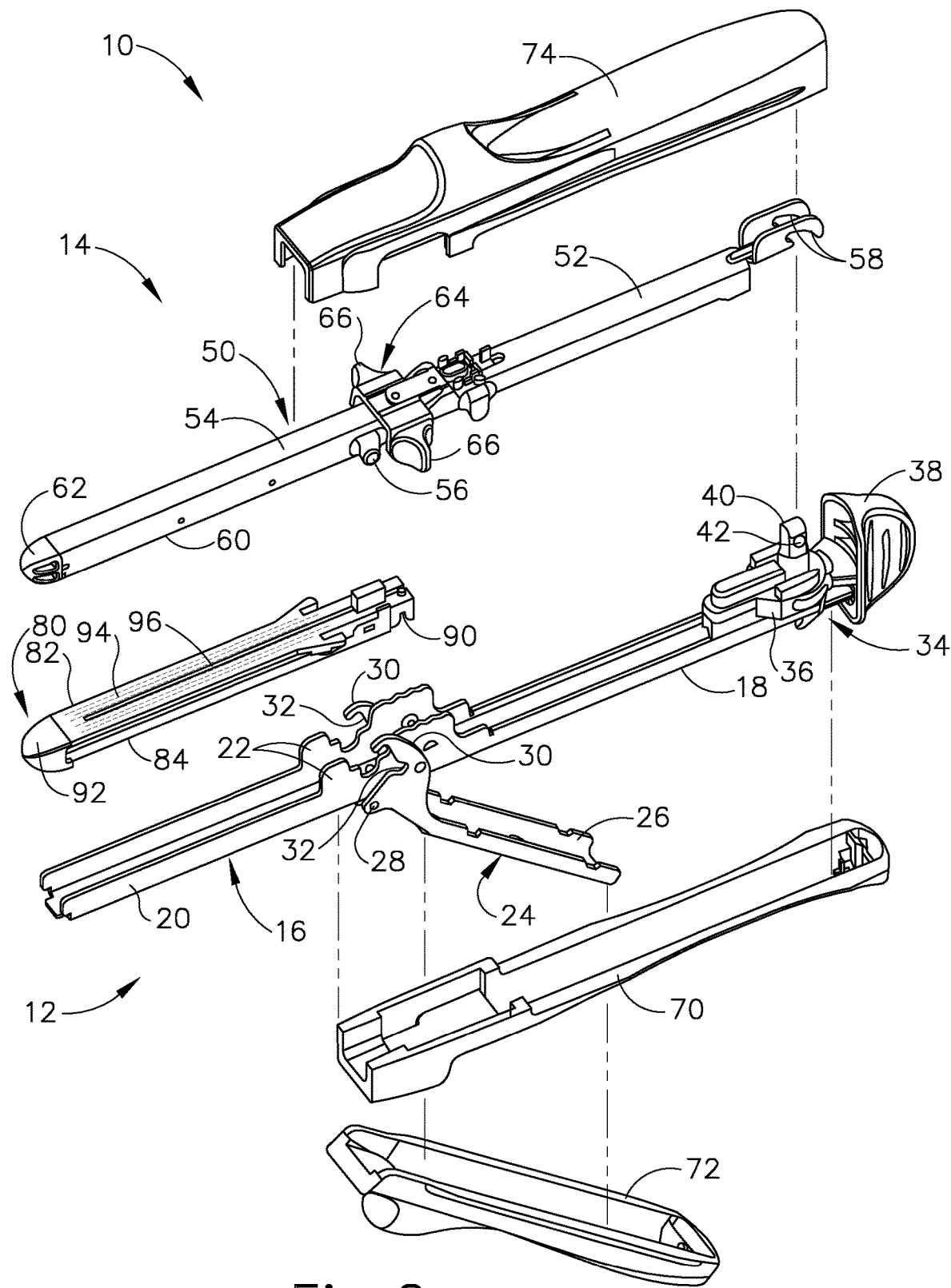
FIG. 2 depicts an exploded perspective view of the linear surgical stapler of FIG. 1.

FIGS. 1 and 2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween. Cartridge half (12) includes an elongate cartridge channel (16) having a proximal frame portion (18) that slidably retains a portion of a firing assembly (34), a distal jaw portion (20) that supports a staple cartridge (80) (or "reload"), and a pair of upright side flanges (22) arranged medially therebetween.

Cartridge half (12) further includes a clamp lever (24) pivotably coupled to an underside of cartridge channel (16) in approximate alignment with side flanges (22). Clamp lever (24) includes an elongate lever arm (26) having a free proximal end and a distal end that is pivotably coupled to cartridge channel (16) with a pivot pin (28). A pair of opposed jaws (30) extends distally from the distal end of lever arm (26) alongside flanges (22) of cartridge channel (16). Each jaw (30) includes a respective elongate slot (32) having a closed proximal end and an open distal end, and which defines upper and lower camming surfaces configured to engage a respective latch projection (56) of anvil half (14). As described below, clamp lever (24) is operable to pivot relative to cartridge channel (16) between open and closed positions to releasably clamp anvil half (14) against cartridge half (12) and thereby capture tissue layers therebetween.

As shown best in FIG. 2, firing assembly (34) of cartridge half (12) includes a slider block (36) slidably retained within proximal frame portion (18) of cartridge channel (16), an actuator (38) (or "firing knob") movably coupled with slider block (36), and an elongate actuating beam (not shown) extending distally from slider block (36) and configured to couple with a sled (100) (see FIG. 3) housed within staple cartridge (80). Actuator (38) of the present example is configured to pivot about the proximal end of cartridge half (12) to provide for "dual-sided firing" of stapler (10). Specifically, actuator (38) may be positioned along either lateral side of cartridge half (12) to perform a distal firing stroke, such that stapler (10) may be conveniently fired in a variety of orientations during a surgical procedure.

Figure 5A:
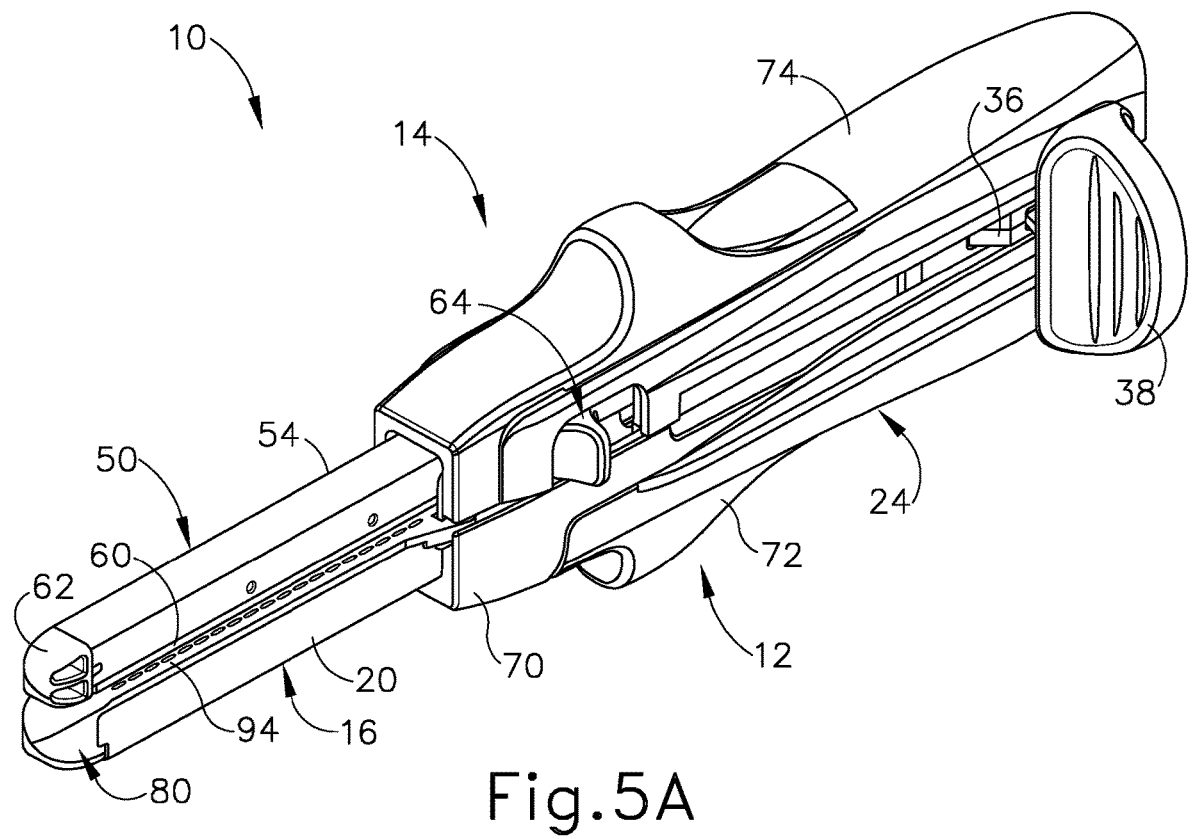
FIG. 5A depicts a distal perspective view of the linear surgical stapler of FIG. 1, showing an actuator of the stapler in a proximal, pre-fired position.
Figure 5B:
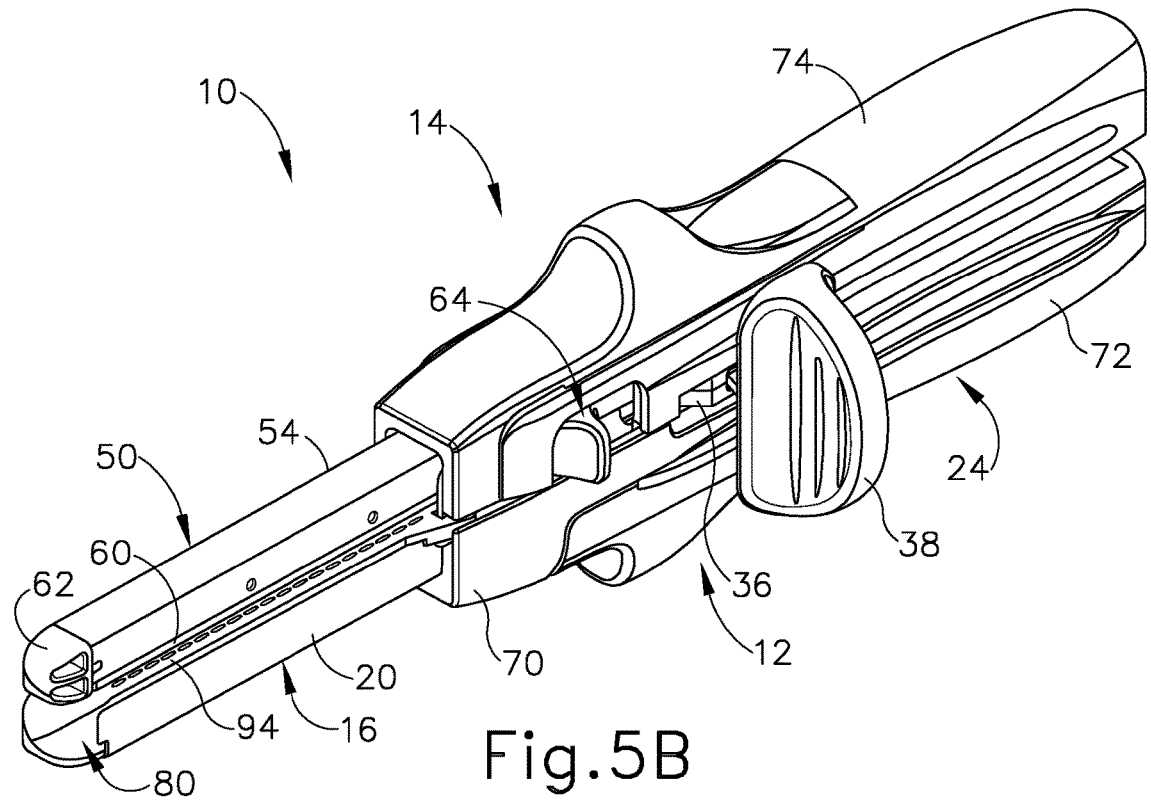
FIG. 5B depicts a distal perspective view of the linear surgical stapler of FIG. 1, showing the actuator in a distal, fired position.

Slider block (36) is configured to be translatably driven within proximal frame portion (18) by actuator (38) between a proximal home position shown in FIGS. 2 and 5A, and a distal fired position shown in FIG. 5B. In the proximal home position, slider block (36) abuts a post (40) fixed at a proximal end of cartridge channel (16). A free end of post (40) supports a laterally extending pivot pin (42). As described below, actuator (38) may be driven distally when stapler halves (12, 14) are fully coupled together and clamp lever (24) is closed. Distal advancement of actuator (38) along either lateral side of stapler (10) drives slider block (36) and the elongate actuating beam distally, which in turn drives sled (100) distally through staple cartridge (80). As described below, distal translation of sled (100) through staple cartridge (80) provides for simultaneous stapling and cutting of tissue clamped between stapler halves (12, 14).

As shown best in FIGS. 1 and 2, anvil half (14) of linear surgical stapler (10) includes an elongate anvil channel (50) having a proximal frame portion (52) and a distal jaw portion (54). Anvil channel (50) further includes a latch feature in the form of a pair of projections (56) that extend transversely from a medial portion of anvil channel (50) in a direction toward cartridge half (12). Each latch projection (56) may include a circular rotating cap configured to be captured within the slot (32) of a respective clamp lever jaw (30) when anvil half (14) is coupled with cartridge half (12) and clamp lever (24) is pivoted from the open position to the closed position, as described below. A pair of hooks (58) extend proximally from a proximal end of frame portion (52) and are configured to releasably capture opposed lateral ends of proximal pivot pin (42) of cartridge half (12). Distal jaw portion (54) supports an anvil surface in the form of an anvil plate (60) having a plurality of staple forming pockets (not shown), and additionally supports a distal tip member (62). In other versions of stapler (10), the anvil surface may be formed integrally with or otherwise be rigidly connected to distal jaw portion (54) of anvil channel (50).

Anvil half (14) of the present example further includes a staple height adjustment mechanism (64) mounted to a medial portion of anvil channel (50). Staple height adjustment mechanism (64) is operatively coupled with anvil plate (60), for example via one or more camming features (not shown), and includes a pair of user-engageable projections (66). Longitudinal adjustment of projections (66) between a plurality of predetermined positions causes anvil plate (60) to move transversely relative to distal jaw portion (54) of anvil channel (50). This enables adjustment of a transverse gap distance between anvil plate (60) and a deck (94) of staple cartridge (80) that defines the height of staples being formed. A larger gap distance, and thus a greater staple height, may be set when stapling tissues of greater thicknesses. Conversely, a smaller gap distance, and thus a smaller staple height, may be set when stapling tissues of lesser thicknesses. It will be appreciated that staple height adjustment mechanism (64) may be omitted in some versions, in which case the anvil surface may be fixed relative to anvil channel (50). For instance, the anvil surface may be formed integrally with or otherwise fixedly secured to distal jaw portion (54).

As shown best in in FIGS. 1 and 2, linear surgical stapler (10) further includes a plurality of shrouds (70, 72, 74) that cover select portions of stapler (10) and promote effective grip and manipulation of stapler (10) by an operator during use. In the present example, cartridge half (12) includes a first shroud (70) that covers an outwardly facing side of proximal frame portion (18) of cartridge channel (16). Cartridge half (12) further includes a second shroud (72) that covers an outwardly facing side of clamp lever (24) and is configured to pivot with clamp lever (24) relative to cartridge channel (16) and first shroud (70). Anvil half (14) includes a third shroud (74) that covers an outwardly facing side of proximal frame portion (52) of anvil channel (50), including proximal hooks (58). Each shroud (70, 72, 74) may be coupled with its respective components of stapler (10) by any suitable means apparent to those of ordinary skill in the art. Additionally, each shroud (70, 72, 74) may be formed of one or more materials and be provided with texturing suitable to promote effective gripping of the shroud (70, 72, 74) by an operator to enable safe and efficient use of stapler (10) during a surgical procedure.

Figure 3:
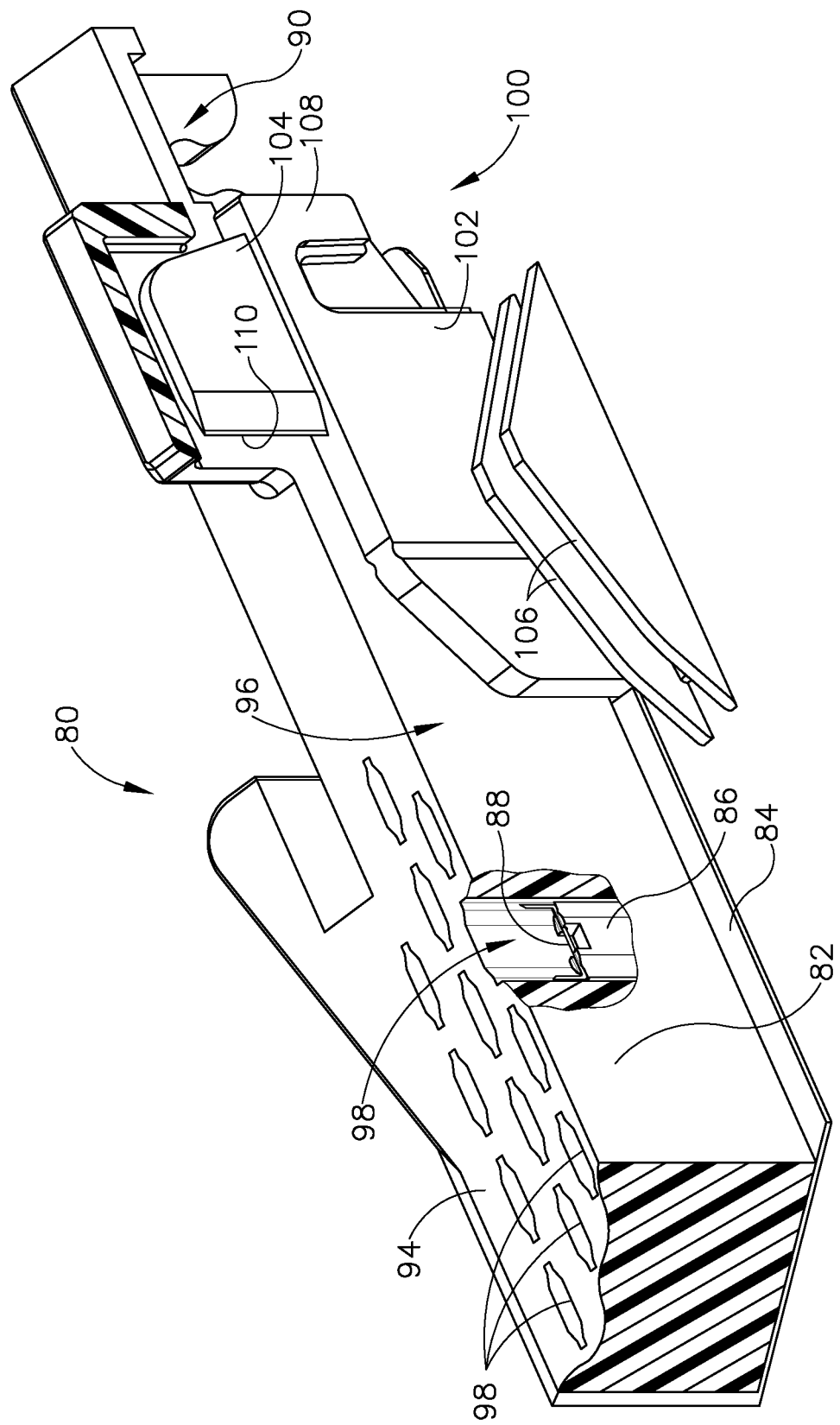
FIG. 3 depicts a cross-sectional perspective view of a staple cartridge assembly of the linear surgical stapler of FIG. 1.

As shown in FIGS. 2 and 3, staple cartridge (80) of the present example is an assembly that comprises a cartridge body (82), a pan (84) that covers an open lower side of cartridge body (82), and a plurality of staple drivers (86) housed within cartridge body (82) and each being configured to drive a respective staple (88). Cartridge body (82) includes a proximal end having coupling features (90) configured to releasably engage corresponding coupling features (not shown) of distal jaw portion (20) of cartridge channel (16), and a distal end defining a tapered nose (92). An upper side of cartridge body (82) defines a generally planar deck (94) through which a longitudinal slot (96) and a plurality of staple cavities (98) open. Each staple cavity (98) houses a respective staple driver (86) and a staple (88). As shown in FIG. 3, an interior of cartridge body (82) slidably houses a sled (100) that comprises a sled body (102) and knife member (104). Lateral sides of sled body (102) support a plurality of cam ramps (106) that taper distally. A proximal end of sled body (102) includes a downwardly extending tab (108) configured to lockingly engage a distal end of the elongate actuating beam (not shown) of firing assembly (34) when staple cartridge (80) is mounted to cartridge half (12) of stapler (10). Knife member (104) extends upwardly from an upper side of sled body (102) and presents a distally facing cutting edge (110) configured to cut tissue.

Sled (100) is configured to translate distally through cartridge body (82) in response to distal actuation of firing assembly (34), such that knife member (104) translates distally through longitudinal slot (96) to cut tissue clamped between stapler halves (12, 14). Simultaneously, cam ramps (106) translate distally through respective interior slots (not shown) of cartridge body (82) to actuate staple drivers (86) and staples (88) upwardly through staple cavities (98) so that free ends of staples (88) pierce through the clamped tissue and deform against staple forming pockets of anvil plate (60). In this manner, distal actuation of firing assembly (34) provides for simultaneous severing and stapling of tissue clamped between the distal end effector portions of stapler halves (12, 14).

Linear surgical stapler (10) and staple cartridge (80) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and/or U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Surgical Stapler

Figure 4A:
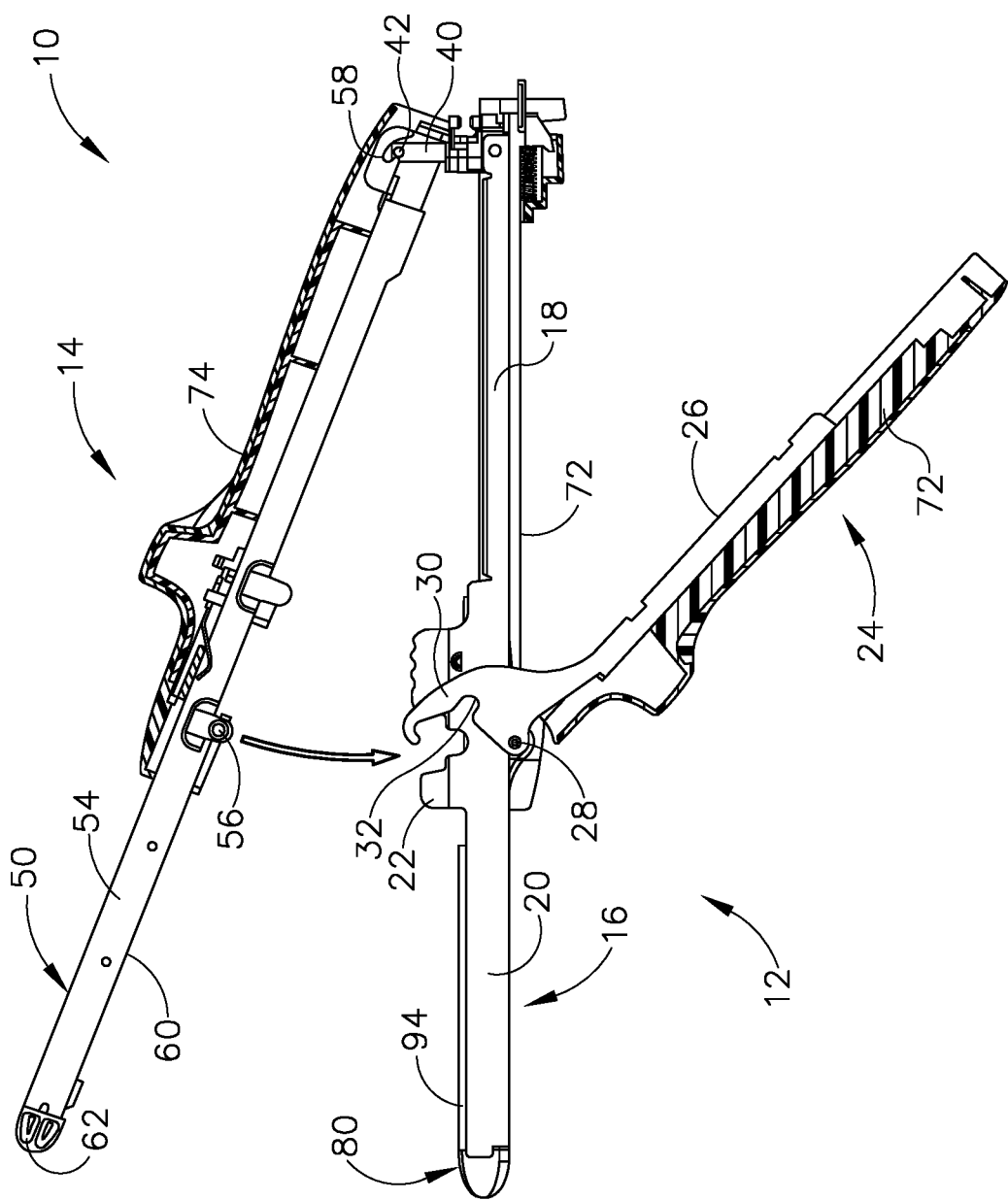
FIG. 4A depicts a cross-sectional side view of the linear surgical stapler of FIG. 1, showing the stapler halves coupled together at their proximal ends with the clamp lever in an open position.
Figure 4B:
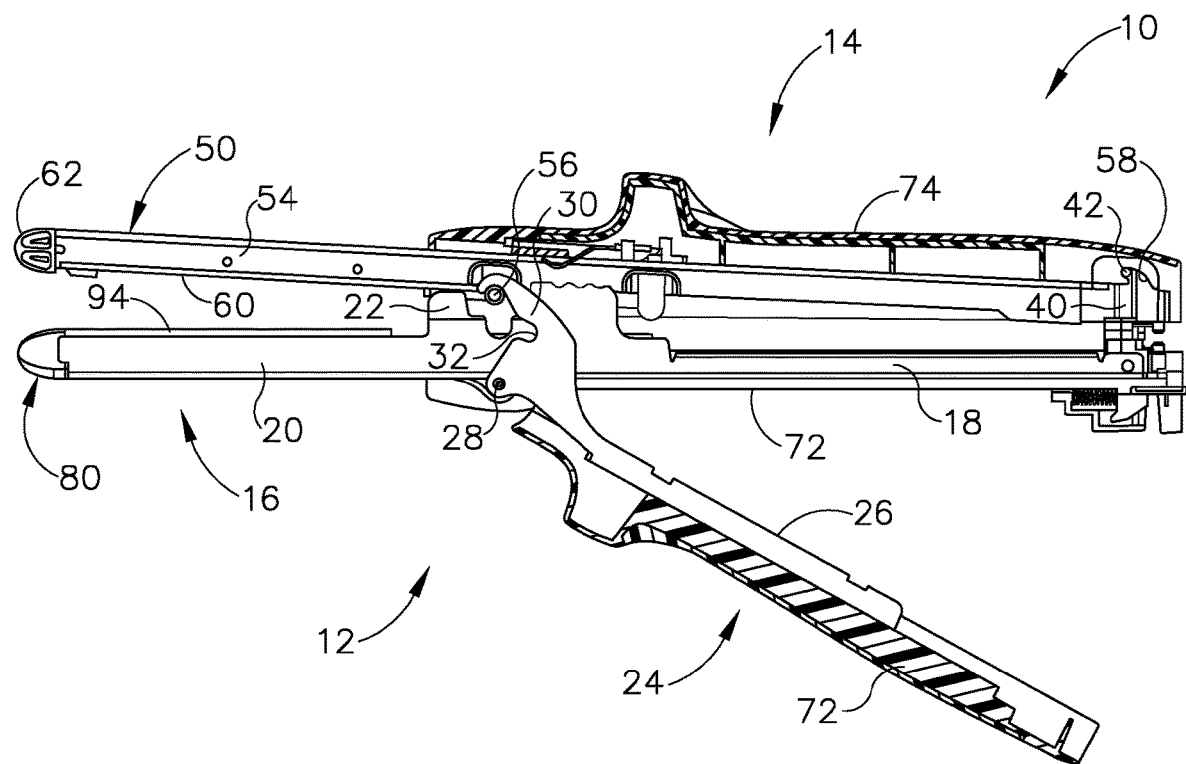
FIG. 4B depicts a cross-sectional side view of the linear surgical stapler of FIG. 1, showing the stapler halves coupled together with the clamp lever in a partially closed position.
Figure 4C:
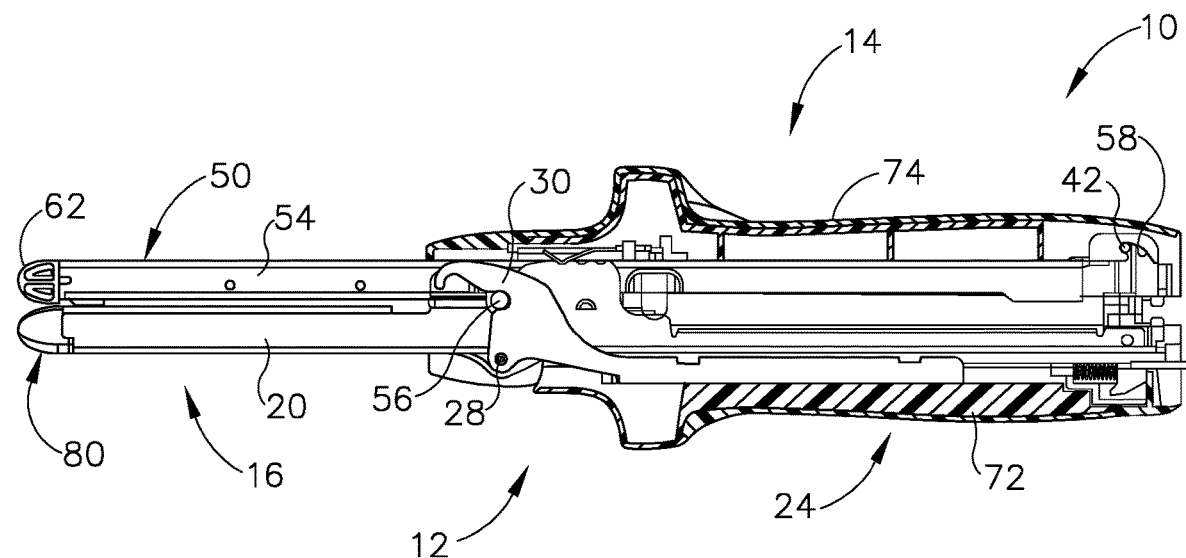
FIG. 4C depicts a cross-sectional side view of the linear surgical stapler of FIG. 1, showing the stapler halves coupled together with the clamp lever in a fully closed position.

FIGS. 4A-4C show exemplary coupling of stapler halves (12, 14) during a surgical procedure. As shown in FIG. 4A, the proximal end of anvil half (14) is aligned with the proximal end of cartridge half (12) such that proximal pivot pin (42) of cartridge half (12) is received by proximal hooks (58) of anvil half (14). With clamp lever (24) in the open position, anvil half (14) is then pivoted toward cartridge half (12), about proximal pivot pin (42), to direct latch projections of anvil half (14) into slots (32) of clamp lever jaws (30). Once latch projections (56) are received by clamp lever jaws (30), clamp lever (24) is pivoted toward the partially closed position shown in FIG. 4B. In this partially closed position of clamp lever (24), anvil half (14) is partially clamped with cartridge half (12) such that stapler (10) may now be held with a single hand without halves (12, 14) undesirably separating from one another. Additionally, in this state, the distal portions of stapler halves (12, 14) remain spaced apart from one another to permit positioning of tissue between the distal portions. It will be appreciated that tissue may be positioned between the distal portions of stapler halves (12, 14) before or upon achieving this partially clamped state.

As shown in FIG. 4C, clamp lever (24) is then pivoted further toward its fully closed position such that the camming surfaces of clamp lever jaws (30) draw latch projections of anvil half (14) proximally against the closed proximal ends of slots (32) of clamp lever jaws (30), thereby fully clamping stapler halves (12, 14) together with tissue positioned securely therebetween. Once halves (12, 14) of stapler (10) are in a fully clamped state, actuator (38) may be manipulated to fire staple cartridge (80). In particular, as shown in FIGS. 5A and 5B, actuator (38) is pivoted about the proximal end of stapler (10) to overlie one of the lateral sides of stapler (10). Actuator (38) is then driven distally to actuate firing assembly (34) in the manner described above and thereby simultaneously sever and staple the clamped tissue. Upon completing a distal firing stroke, actuator (38) may be returned to its proximal home position shown in FIG. 2, and clamp lever (24) may then be opened to separate stapler halves (12, 14) from one another and release the stapled and severed tissue.

II. Exemplary Linear Surgical Stapler Having Proximal Retaining Assembly

As described above in connection with FIGS. 4A-4C, clamp lever (24) must be actuated from its fully open position to at least a partially closed position in which lever jaws (30) initially capture latch projections (56) of anvil half (14) in order to prevent separation of anvil half (14) from cartridge half (12). However, this initial coupling process requires the use of both hands of an operator, thus preventing the operator from being able to mount tissue to stapler (10) when clamp lever (24) is fully opened. Because it is generally easier to mount tissue to stapler halves (12, 14) while clamp lever (24) is fully opened, thus allowing the distal portions of stapler halves (12, 14) to be spaced further apart from one another, the operator will often enlist the help of an assistant in a "4-hands" assembly approach.

In many instances, it may be desirable for an operator to be able to mount tissue to the separate halves of a linear surgical stapler with the clamp lever in a fully open position and without the aid of an assistant, such that the operator may use a first hand to hold the stapler and a second hand to position tissue relative to the stapler. The exemplary stapler (200) described below includes features that enable proximal ends of the first and second stapler halves to remain coupled together while the clamp lever is in a fully open position. This configuration enables the operator to suitably manipulate stapler (200) with a first hand, while leaving the other hand free to manipulate tissue relative to stapler (200).

A. Overview of Linear Surgical Stapler

Figure 6:
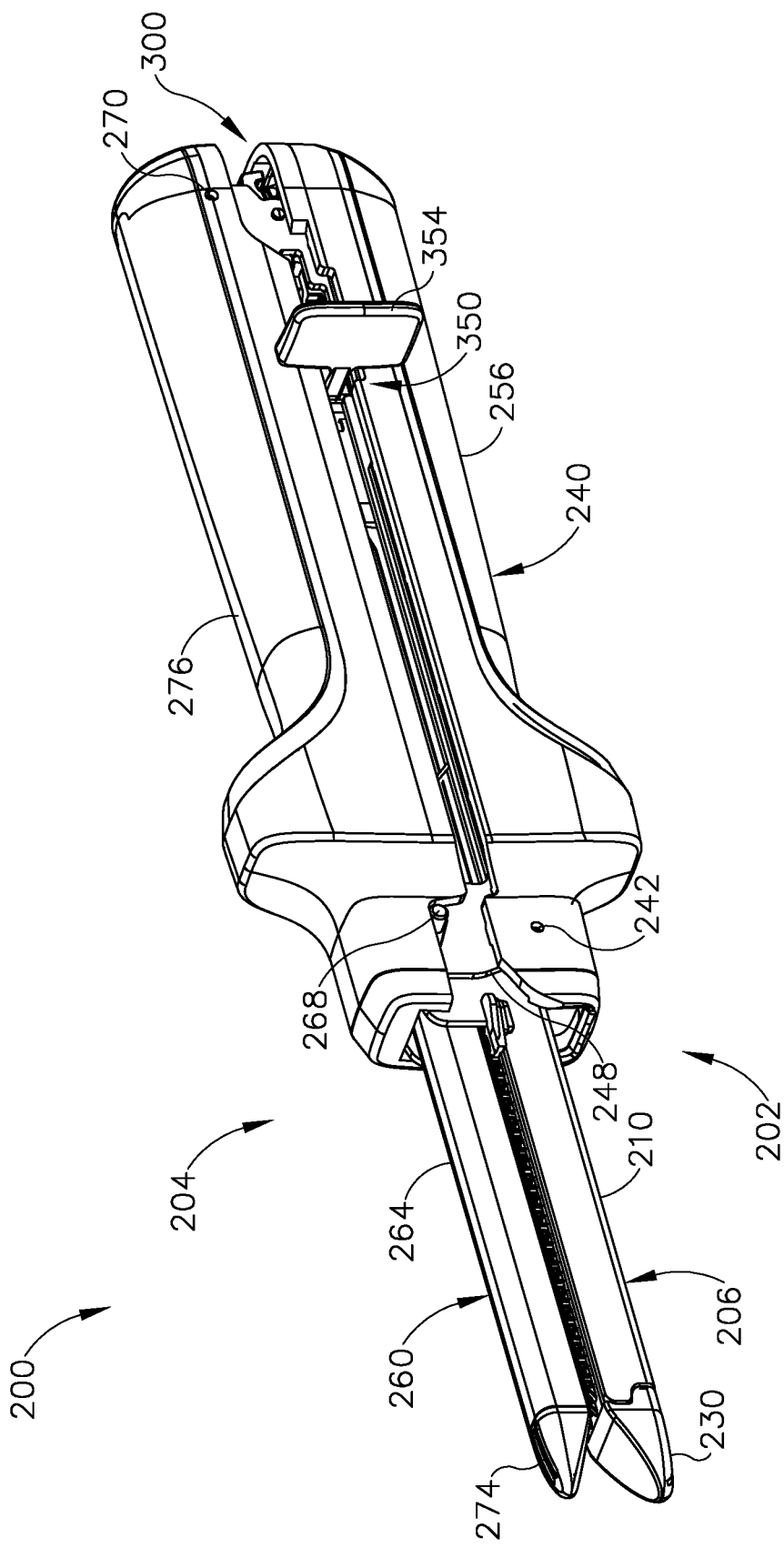
FIG. 6 depicts a distal perspective view of another exemplary linear surgical stapler, showing a cartridge half and an anvil half of the stapler coupled together with a clamp lever of the cartridge half in a fully closed position.
Figure 7:
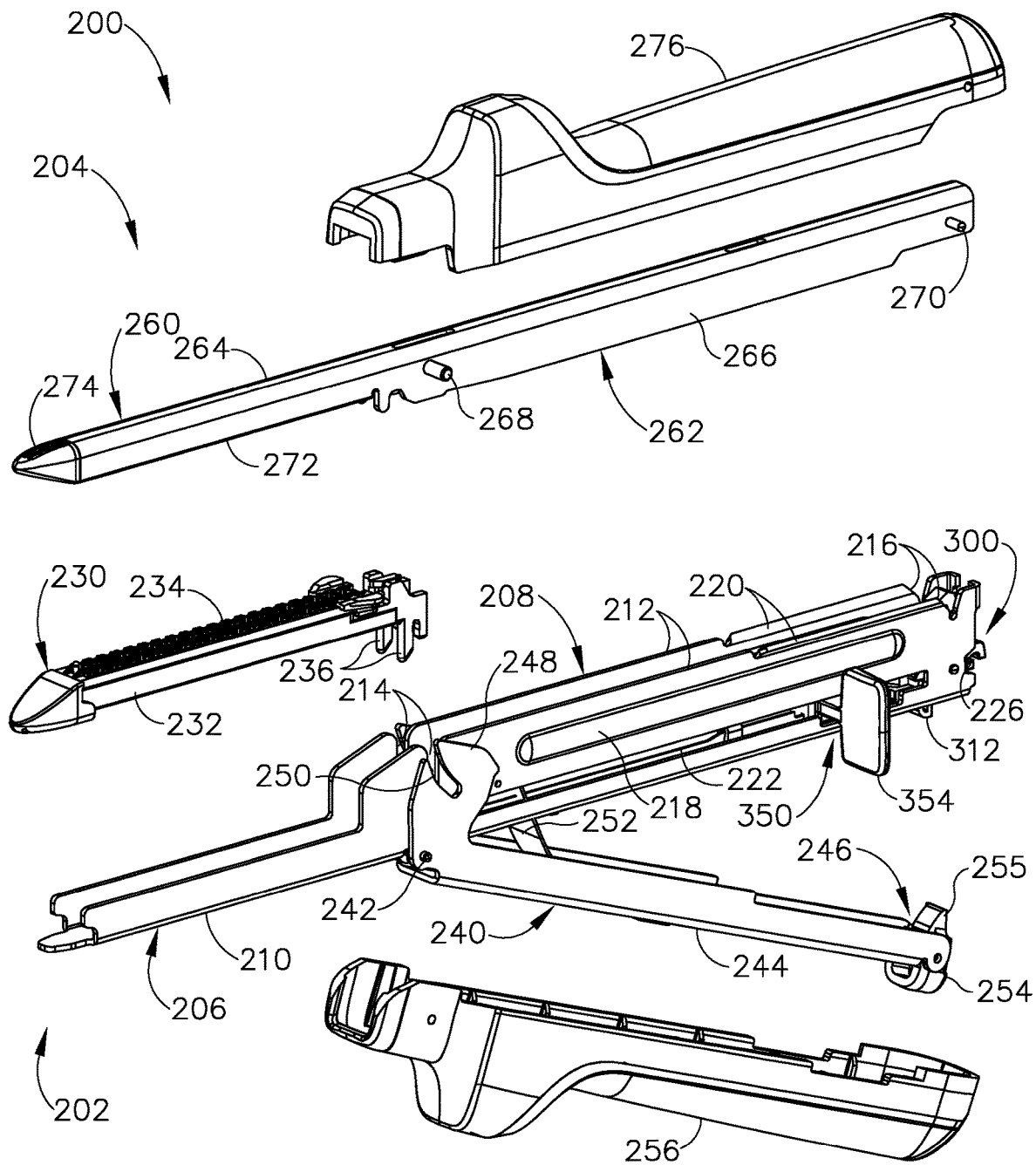
FIG. 7 depicts an exploded perspective view of the linear surgical stapler of FIG. 6.

FIGS. 6 and 7 show another exemplary linear surgical stapler (200) (or "linear cutter") that is generally similar to linear surgical stapler (10) described above except as otherwise described below. Linear surgical stapler (200) includes a cartridge half (202) (or "reload half") and an anvil half (204) configured to releasably couple together to clamp tissue therebetween for simultaneous cutting and stapling of the clamped tissue.

Cartridge half (202) includes an elongate cartridge channel (206) having a proximal frame portion (208) and distal jaw portion (210). Proximal frame portion (208) slidably retains a firing assembly (350) and includes a laterally opposed pair of upright side flanges (212). Each side flange (212) includes a vertical slot (214) arranged at a distal end thereof, and a tapered notch (216) arranged at a proximal end thereof. An outwardly projecting stiffening rib (218) extends longitudinally between distal slot (214) and the proximal notch (216) of each side flange (212) and is configured to provide the side flange (212) with enhanced stiffness. An outwardly flared upper segment (220) defines an upper edge of a proximal portion of each side flange (212) and is configured to facilitate receipt of anvil half (204) by cartridge half (202), as described in greater detail below. Each side flange (212) further includes an elongate firing slot (222) extending longitudinally between proximal notch (216) and distal slot (214) along a lower side of side flange (212). Elongate firing slots (222) are configured to guide firing assembly (350) between proximal and distal positions. Firing assembly (350) is described in greater detail below in connection with FIGS. 16-21.

Distal jaw portion (210) of cartridge channel (206) is configured to receive a staple cartridge (230) (or "reload"), which may be similar to staple cartridge (80) described above except as otherwise described below. Staple cartridge (230) includes a cartridge body (232) that houses a plurality of staple drivers and staples (not shown) similar to staple drivers (86) and staples (88). Cartridge body (232) further includes a longitudinal slot (234) configured to slidably receive a knife member (366) (see FIG. 16) of firing assembly (350), and a pair of interior slots (not shown) configured to slidably receive a pair of cam ramps (360) (see FIG. 16) of firing assembly (350). In other versions, staple cartridge (230) and firing assembly (350) may be alternatively configured such that knife member (366) and cam ramps (360) are housed within cartridge body (232), similar to staple cartridge (80). Staple cartridge (230) of the present version further includes a pair of proximal coupling legs (236) configured to be directed through an opening (not shown) in a lower wall of cartridge channel (206) and releasably couple to a clamp lever pivot pin (242) with a snap-fit engagement.

Cartridge half (202) further includes a clamp lever (240) pivotably coupled to cartridge channel (206) with clamp lever pivot pin (242), which is arranged in approximate alignment with distal slots (214) of cartridge channel side flanges (212). Clamp lever (240) includes an elongate lever arm (244) having a free proximal end (246) and a distal end that is pivotably coupled to a lower portion of cartridge channel (206) with pivot pin (242). A pair of opposed jaws (248) extend distally from the distal end of lever arm (244) alongside cartridge channel side flanges (212). Each jaw (248) includes a curved slot (250) having a closed proximal end and an open distal end configured to receive a latch projection of anvil half (204), as described below.

Clamp lever (240) is operable to pivot relative to cartridge channel (206) between an open position in which proximal end (246) of lever arm (244) is spaced from cartridge channel frame portion (208), and a closed position in which proximal end (246) confronts cartridge channel frame portion (208). Actuation of clamp lever (240) from the open position to the closed position operates to clamp anvil half (204) against cartridge half (202). In particular, the curvature of each jaw slot (250) defines respective upper and lower camming surfaces configured to engage and draw the respective latch projection of anvil half (204) toward cartridge channel (206) as clamp lever (240) is pivotably closed, as described below.

Cartridge half (202) of the present example further includes a resilient member shown in the form of a flat spring (252) that biases lever arm (244) toward the open position. Accordingly, flat spring (252) promotes disengagement of lever jaws (248) from anvil half (204) upon initial advancement of clamp lever (240) from the closed position toward the open position. Cartridge half (202) further includes a clamp lever latch member (254) arranged at proximal end (246) of lever arm (244). As described in greater detail below, clamp lever latch member (254) is resiliently biased to engage a proximal end of cartridge channel (206) and thereby releasably retain clamp lever (240) in the closed position, for instance while stapler (200) is being fired.

Anvil half (204) of linear surgical stapler (200) includes an elongate anvil channel (260) having a proximal frame portion (262) and a distal jaw portion (264). Proximal frame portion (262) includes a laterally opposed pair of upright side flanges (266) that are configured to be received between cartridge channel side flanges (212) when anvil half (204) is coupled with cartridge half (202). A distal latch projection in the form of a distal pin (268) extends laterally through the distal ends of anvil channel side flanges (266), and a proximal pivot projection in the form of a proximal pin (270) extends laterally through the proximal ends of anvil channel side flanges (266). Anvil pins (268, 270) are configured to facilitate coupling of anvil half (204) with cartridge half (202) as described below.

Distal jaw portion (264) of anvil half (204) supports an anvil surface (272) having a plurality of staple forming pockets (not shown) configured to deform the legs of staples ejected by staple cartridge (230) when stapler (200) is fired. In some versions, anvil surface (272) may be formed integrally with or otherwise be rigidly connected to distal jaw portion (264), for example as described below in connection with FIGS. 37A-39. In other versions, anvil surface (272) may be adjustable relative to distal jaw portion (264) in a manner similar to anvil plate (60) of stapler (10) described above. Distal jaw portion (264) of anvil half (204) additionally supports a tapered distal tip member (274).

Similar to linear surgical stapler (10), linear surgical stapler (200) includes a plurality of shrouds (256, 276) that cover select portions of stapler (200) and promote effective grip and manipulation of stapler (200) by an operator during use. In particular, a clamp lever shroud (256) is affixed to and covers an outwardly facing side of clamp lever (240) such that clamp lever shroud (256) is configured to pivot with clamp lever (240) relative to cartridge channel (206). Additionally, an anvil shroud (276) is affixed to and covers an outwardly facing side of anvil channel (260). In some versions, anvil shroud (276) may be coupled with anvil channel (260) in accordance with the teachings of U.S. patent application Ser. No. 16/102,170, entitled "Clamping Assembly for Linear Surgical Stapler," filed on Aug. 13, 2018, published as U.S. Pub. No. 2020/0046353 on Feb. 13, 2020, issued as U.S. Pat. No. 11,278,285 on Mar. 22, 2022, the disclosure of which is incorporated by reference herein. It will be appreciated that in other versions, shrouds (256, 276) may be coupled with clamp lever (240) and anvil channel (260) in a variety of other manners readily apparent to those of ordinary skill in the art.

During assembly of stapler halves (202, 204), proximal pin (270) of anvil half (204) is directed into proximal tapered notches (216) of cartridge channel (206). Meanwhile, clamp lever (240) is held in the open position by resilient member (252) such that the open distal ends of curved jaw slots (250) align with the open upper ends of cartridge channel distal slots (214). Anvil half (204) is then pivoted about proximal pin (270) to direct distal pin (268) of anvil half (204) into vertical distal slots (214) of cartridge channel (206) and curved jaw slots (250) of clamp lever (240). Clamp lever (240) is then pivoted from the open position to the closed position, which causes the upper and lower camming surfaces of curved jaw slots (250) to engage and draw distal pin (268) toward the closed proximal ends of curved jaw slots (250). This action draws distal jaw portion (264) of anvil channel (260) closer toward distal jaw portion (210) of cartridge channel (206), thereby clamping any tissue positioned between anvil surface (272) and staple cartridge (230). When clamp lever (240) reaches the fully closed position, clamp lever latch member (254) engages the proximal end of cartridge channel (206) to maintain clamp lever (240) in the closed position. Stapler (200) may then be fired by actuating firing assembly (350) distally similar to firing assembly (34). After firing, firing assembly (350) is returned to its proximal home position, and clamp lever latch member (254) is disengaged from cartridge channel (206) to enable opening of clamp lever (240) and subsequent separation of stapler halves (202, 204).

B. Proximal Retaining Assembly of Linear Surgical Stapler

FIGS. 8-11 show details of an exemplary retaining assembly (300) arranged at a proximal end of linear surgical stapler (200) and which is configured to releasably retain portions of anvil half (204) and firing assembly (350) as described below. Retaining assembly (300) of the present example includes an anvil latch member (302) and a detent member (304), both of which are rotatably coupled with a proximal end of cartridge channel (206) via a laterally extending pin (306) arranged proximally of firing slots (222).

Figure 10:
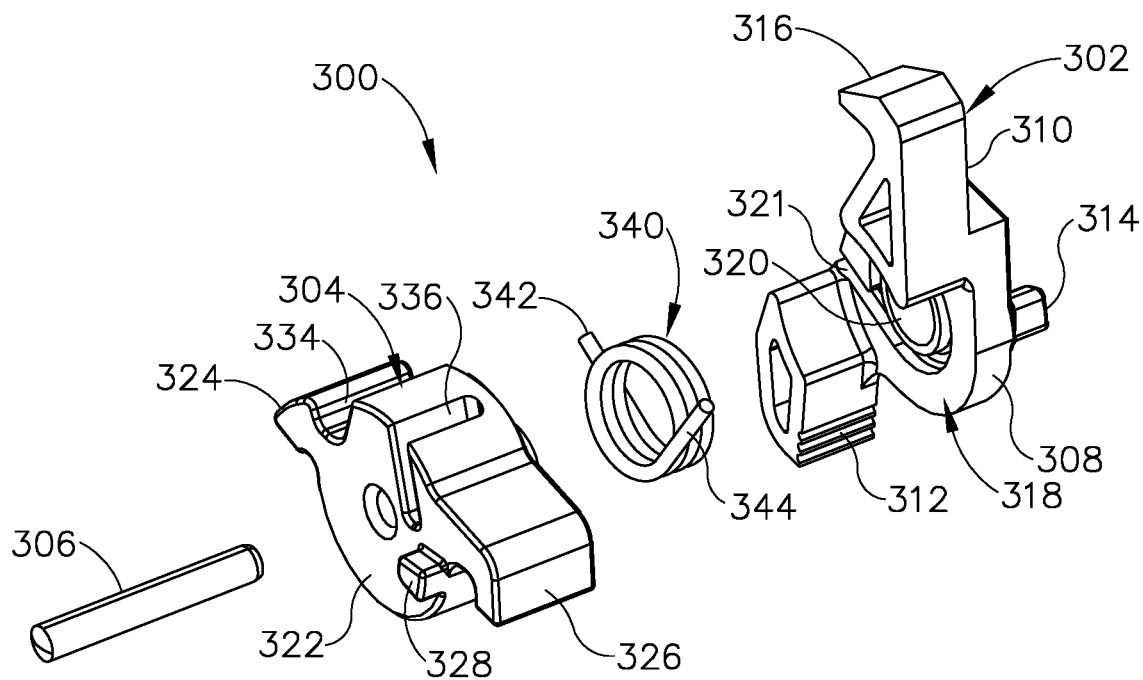
FIG. 10 depicts an exploded left perspective view of the proximal retaining assembly of FIG. 9.
Figure 11:
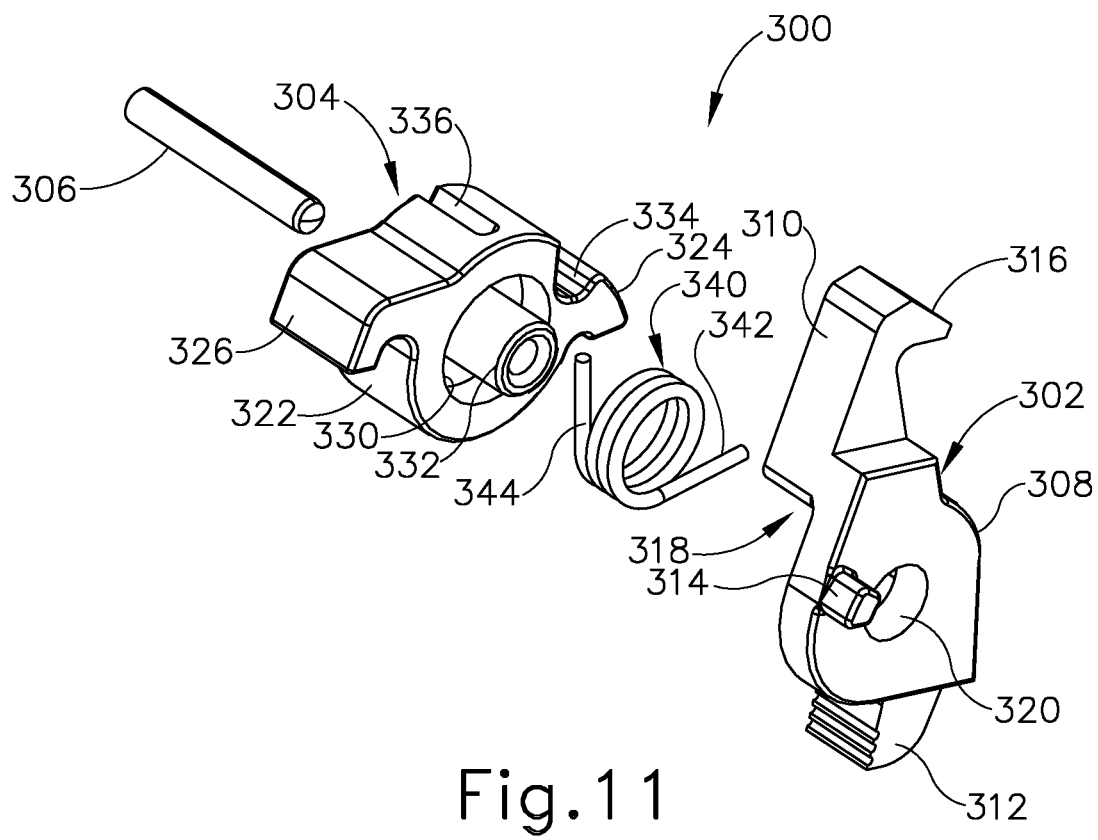
FIG. 11 depicts an exploded right perspective view of the proximal retaining assembly of FIG. 9.

As shown best in FIGS. 10 and 11, anvil latch member (302) includes a central body (308), a latch finger (310) extending upwardly from an upper side of central body (308), a release button (312) extending downwardly from a lower side central body (308), and a stop tab (314) arranged on an outwardly facing lateral side of central body (308) opposed from detent member (304). An upper end of latch finger (310) tapers distally and defines an upper cam ramp (316) configured to engage proximal pin (270) of anvil half (204) in the manner described below. Anvil latch member (302) further includes a central cutout feature (318) shaped to receive a portion of detent member (304) as described below, and an opening (320) extending laterally through central body (308).

Detent member (304) includes a generally cylindrical central body (322), a distal finger (324) extending distally from a distal side of central body (322), a hook element (326) extending proximally from a proximal side of central body (322), and a stop tab (328) arranged on an outwardly facing lateral side of central body (322) opposed from anvil latch member (302). As shown in FIG. 11, a lateral side of detent member (304) that confronts anvil latch member (302) includes an annular recess (330) and a shaft (332) extending laterally from annular recess (330) in a direction toward anvil latch member (302). Distal finger (324) of detent member (304) includes a proximal uppercut feature (334) that defines a proximal cam ramp of distal finger (324), and a sloped distal end that defines a distal cam ramp of distal finger (324). These proximal and distal cam ramps of distal finger (324) are configured to interact with firing assembly (350) as described in greater detail below.

Figure 8:
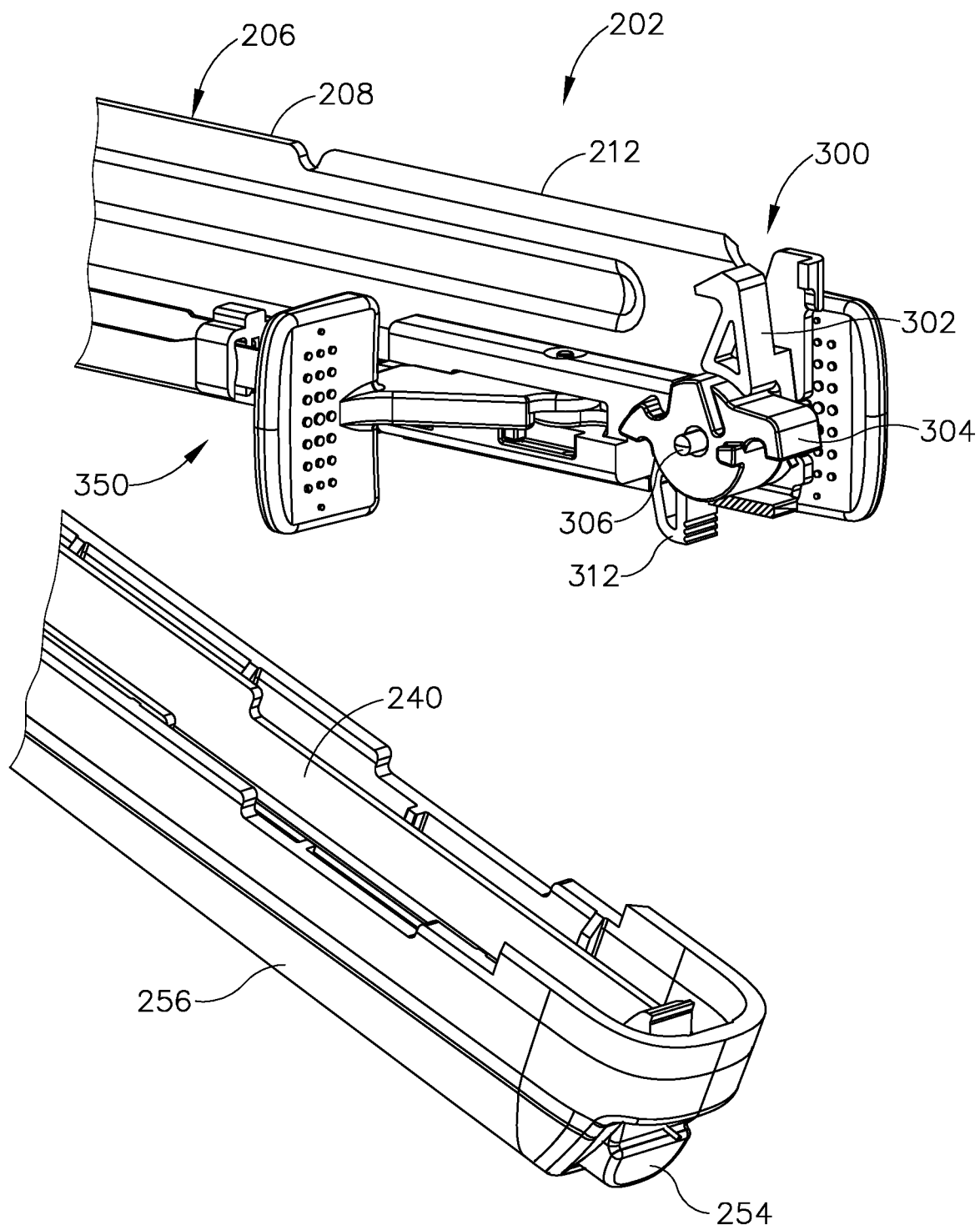
FIG. 8 depicts a perspective view of a proximal portion of the cartridge half of the linear surgical stapler of FIG. 6, showing the clamp lever in an open position and revealing internal features of the cartridge half.
Figure 9:
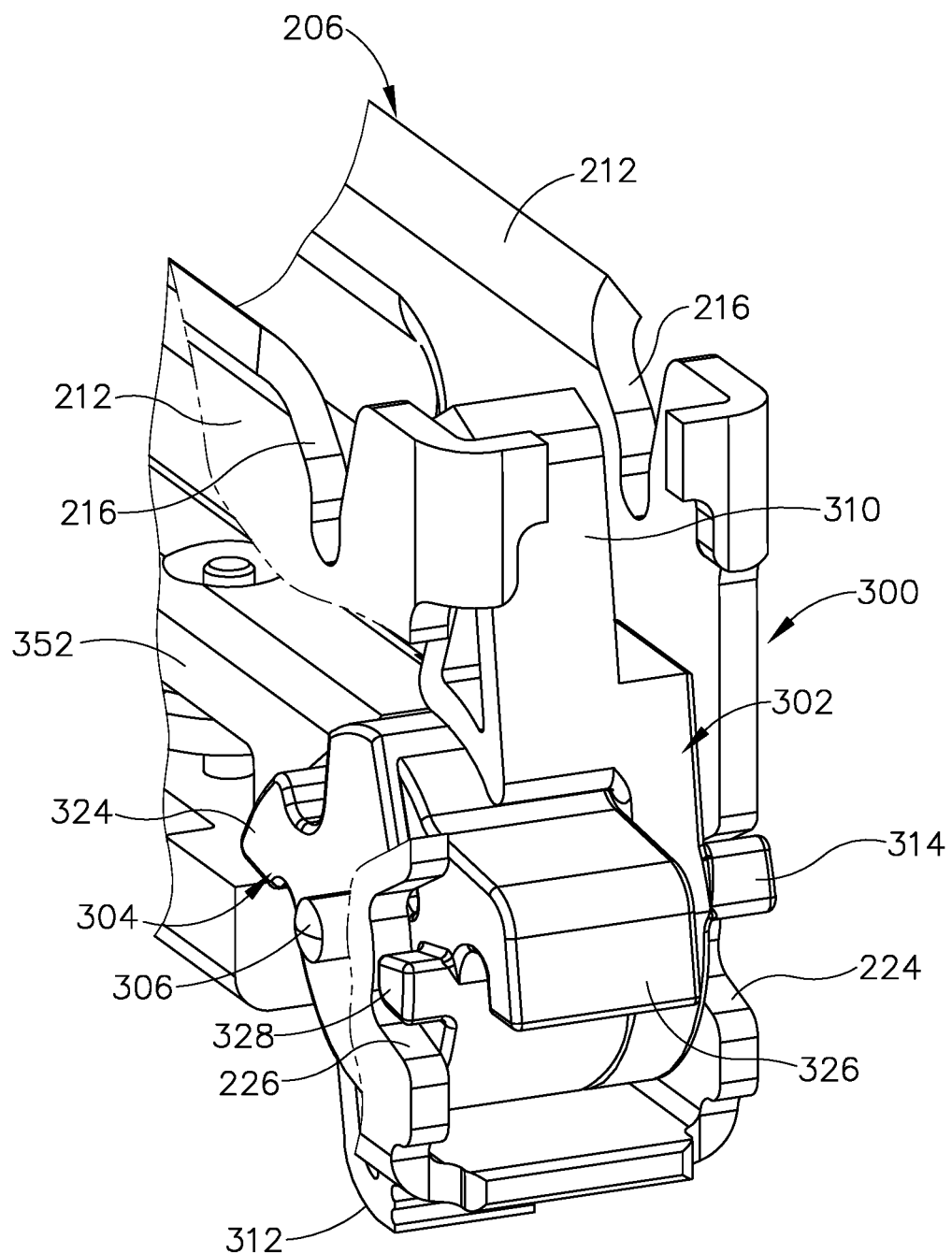
FIG. 9 depicts a perspective view of a proximal end of the cartridge half of FIG. 8, showing a side portion of a cartridge channel of the cartridge half partially cut away to reveal a proximal retaining assembly that includes an anvil latch member and a detent member.

Anvil latch member (302) and detent member (304) are configured to mate together such that their inwardly facing lateral sides confront one another along a plane that extends generally parallel to a longitudinal axis of linear surgical stapler (200). Central body (322) of detent member (304) is received within central cutout feature (318) of anvil latch member (302) such that latch finger (310) and release button (312) of anvil latch member (302) laterally overlie central body (322) of detent member (304). Additionally, lateral shaft (332) of detent member (304) is received through lateral opening (320) of anvil latch member (302), such that anvil latch member (302) may rotate about shaft (332). Pin (306) is then received through a central bore of lateral shaft (332) and is secured at its lateral ends to cartridge channel side flanges (212), as shown in FIGS. 8 and 9. Accordingly, anvil latch member (302) and detent member (304) are arranged coaxially about a lateral axis defined by pin (306) and shaft (332). As described below, anvil latch member (302) and detent member (304) are configured to rotate independently from and relative to one another about the shared axis.

Retaining assembly (300) further includes a resilient member shown in the form of a torsion spring (340) positioned between anvil latch member (302) and detent member (304). A first lateral side of torsion spring (340) and a corresponding first spring leg (342) is captured within a complementary shaped recess (321) formed in central body (308) of anvil latch member (302). A second lateral side of torsion spring (340) is received within annular recess (330) of detent member (304) such that a corresponding second spring leg (344) is captured within a radially extending slot (336) formed in central body (322) of detent member (304). Torsion spring (340) is configured to resiliently bias anvil latch member (302) and detent member in opposite rotational directions about the lateral axis defined by pin (306). In particular, in the views depicted in FIGS. 9 and 12A-12C, torsion spring (340) is configured to bias anvil latch member (302) in a counter-clockwise direction about pin (306) such that latch finger (310) is biased distally. Additionally, torsion spring (340) is configured to bias detent member (304) in a clockwise direction such that distal finger (324) is biased upwardly and proximal hook element (326) is biased downwardly.

As shown in FIG. 9, stop tab (314) of anvil latch member (302) is configured to abut the upper surface of an adjacent first stop notch (224) formed in the distal end of a corresponding first side flange (212) of cartridge channel (206). Additionally, stop tab (328) of detent member (304) is configured to abut the lower surface of an adjacent second stop notch (226) formed in the distal end of a corresponding second side flange (212) of cartridge channel (206). Anvil latch member stop tab (314) and its respective channel stop notch (224) are configured to interact such that anvil latch member (302) is biased toward a rotational orientation in which latch finger (310) extends generally vertically. Additionally, detent member stop tab (328) and its respective channel stop notch (226) are configured to interact such that detent member (304) is biased toward a rotational orientation in which distal finger (324) and proximal hook element (326) extend generally horizontally.

Figure 12A:
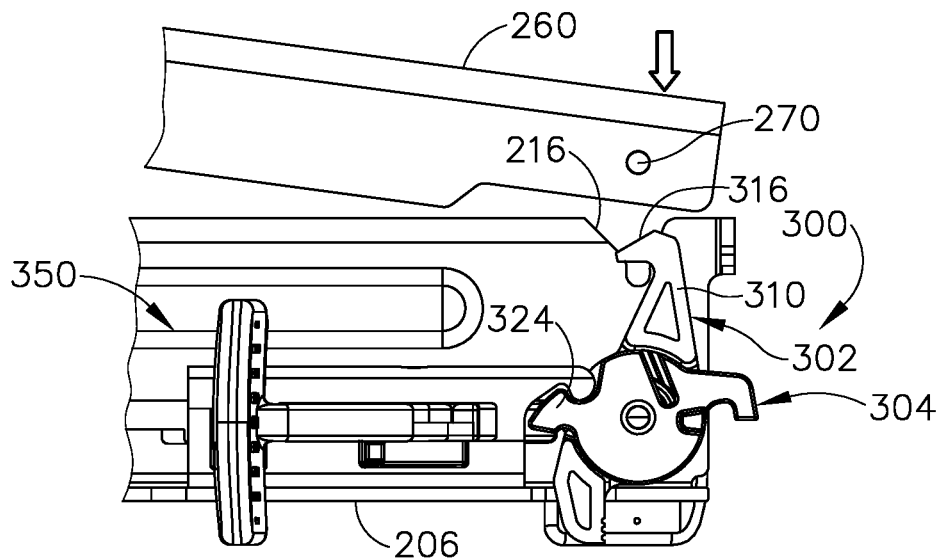
FIG. 12A depicts a side elevational view of the linear surgical stapler of FIG. 6 with an anvil shroud omitted and a side portion of the cartridge channel cut away, showing the anvil latch member in a first rotational position as a proximal end of the anvil half is aligned with a proximal end of the cartridge half.
Figure 12B:
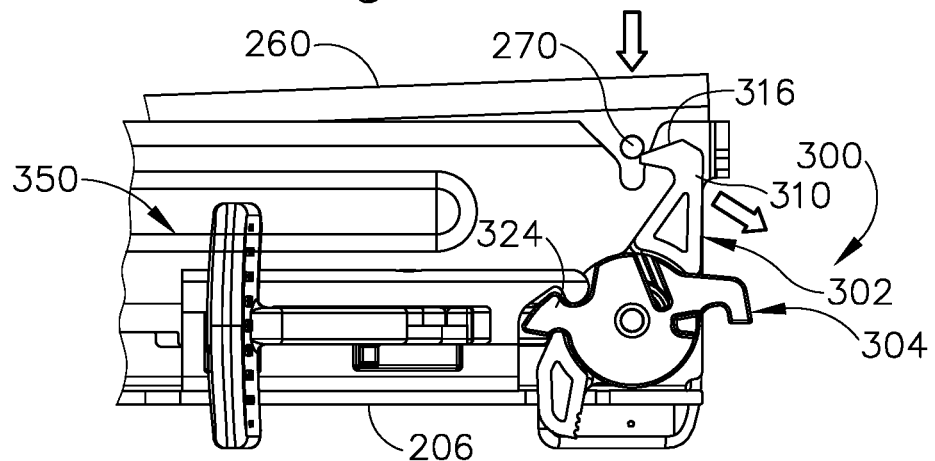
FIG. 12B depicts a side elevational view of the linear surgical stapler of FIG. 6 with the anvil shroud omitted and a side portion of the cartridge channel cut away, showing the anvil latch member in a second rotational position as a proximal pin of the anvil half engages an upper surface of the anvil latch member.
Figure 12C:
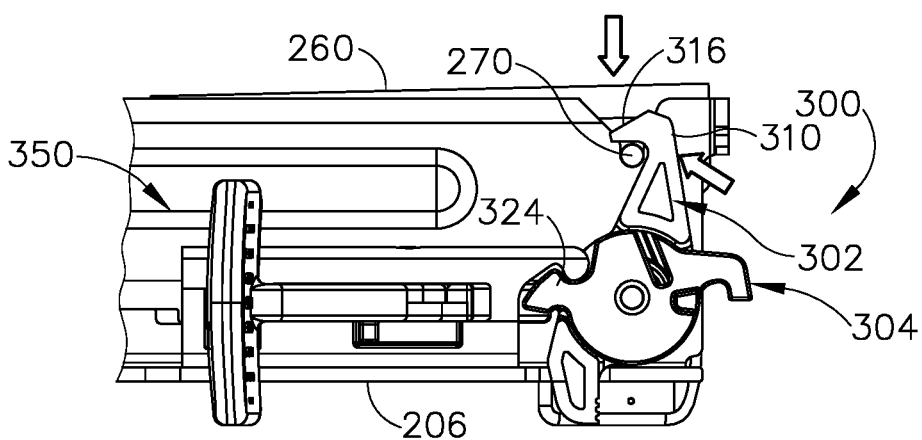
FIG. 12C depicts a side elevational view of the linear surgical stapler of FIG. 6 with the anvil shroud omitted and a side portion of the cartridge channel cut away, showing the anvil latch member after having returned to the first rotational position to releasably capture the proximal anvil pin and thereby couple the proximal ends of the stapler halves together.

FIGS. 12A-12C show engagement of anvil latch member (302) with proximal pin (270) of anvil half (204) to provide for releasable coupling of the proximal end of anvil half (204) with the proximal end of cartridge half (202). FIG. 12A shows cartridge half (202) and anvil half (204) in a pre-assembled state in which anvil half (204) is separated from cartridge half (202), clamp lever (240) (not depicted) is in a fully open position, and firing assembly (350) is held in a proximal home position by distal finger (324) of detent member (304), as described in greater detail below. As shown in FIGS. 12A and 12B, the proximal end of anvil half (204) is aligned with and brought toward the proximal end of cartridge half (202) such that proximal pin (270) is directed into proximal tapered notches (216) of cartridge channel (206) and contacts upper cam ramp (316) of anvil latch member (302). This engagement forces anvil latch member (302) to rotate clockwise such that latch finger (310) moves proximally, which allows proximal pin (270) to slip over the tapered distal tip of latch finger (310). As shown in FIG. 12C, anvil latch member (302) then snaps back counter-clockwise such that latch finger (310) hooks over and captures proximal pin (270), thereby coupling the proximal end of anvil half (204) with the proximal end of cartridge half (202). Because anvil latch member (302) is rotatable independently of detent member (304), detent member (304) remains rotationally stationary throughout the coupling steps shown in FIGS. 12A-12C.

Figure 13A:
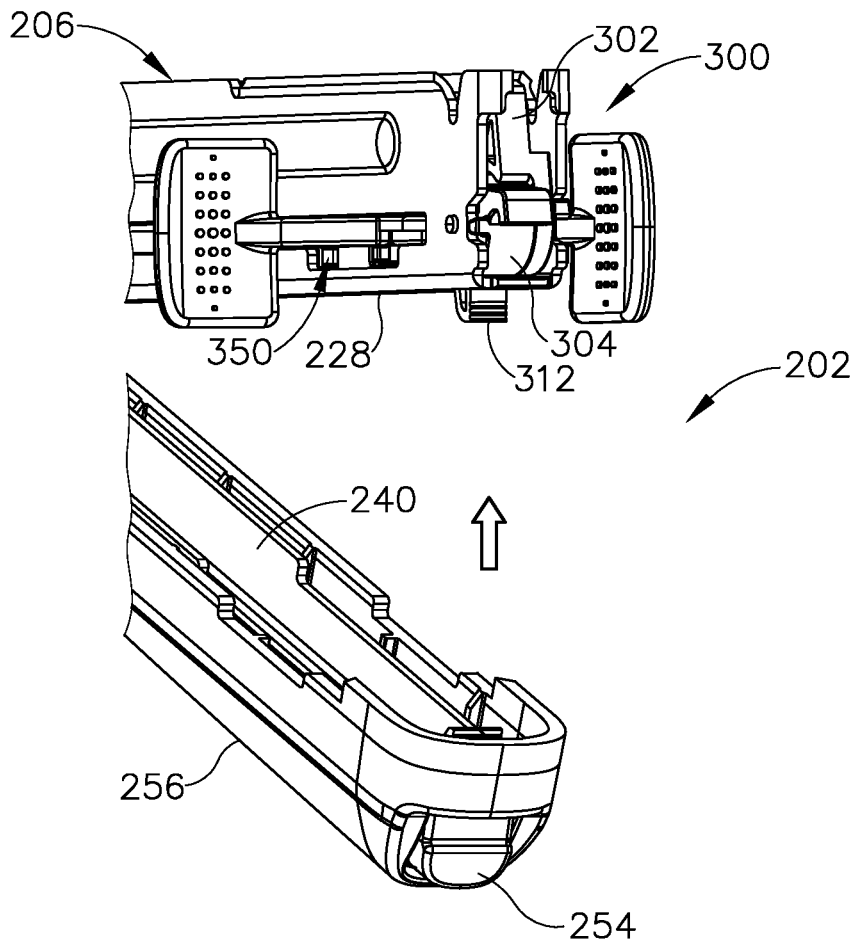
FIG. 13A depicts a perspective view of a proximal portion of the cartridge half of the linear surgical stapler of FIG. 6, showing the clamp lever in an open position.
Figure 13B:
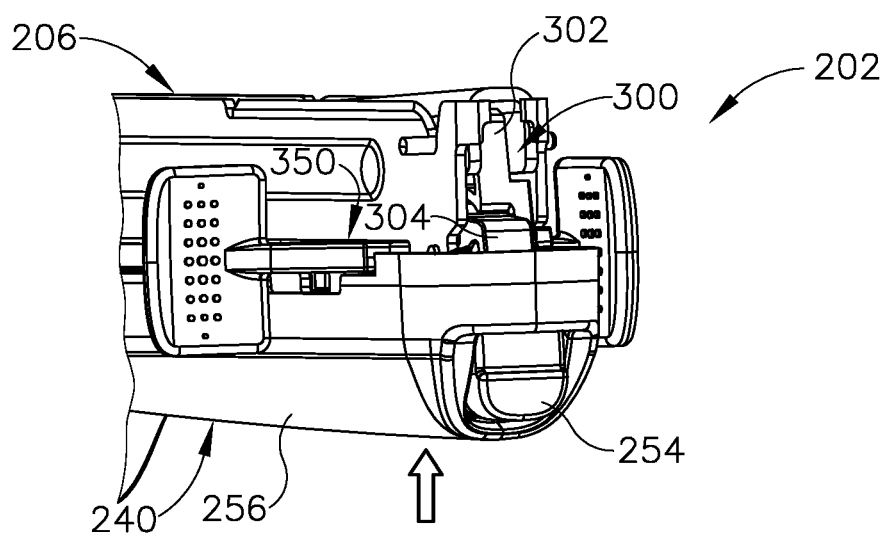
FIG. 13B depicts a perspective view of a proximal portion of the cartridge half of FIG. 13A, showing the clamp lever in a closed position in which a latch of the clamp lever engages a proximal end of the cartridge channel.

As shown in FIGS. 13A and 13B, release button (312) of anvil latch member (302) is exposed and accessible to an operator only when clamp lever (240) is in the open position. As shown in FIG. 13A, release button (312) extends through an opening formed in a bottom wall (228) of cartridge channel (206). As shown in FIG. 13B, clamp lever (240) in the closed position conceals and blocks access to release button (312), thereby preventing unintentional actuation of release button (312) and resulting separation of the proximal ends of stapler halves (202, 204) during or immediately before a firing stroke. As shown in FIGS. 14A and 14B, separation of the proximal ends of stapler halves (202, 204) is achieved by opening clamp lever (240) and actuating release button (312) distally. As shown in FIG. 14B, this causes anvil latch member (302) to rotate clockwise, thereby driving latch finger (310) proximally to release proximal pin (270) of anvil half (204) so anvil half (204) may be pulled away from cartridge half (202).

Figure 18:
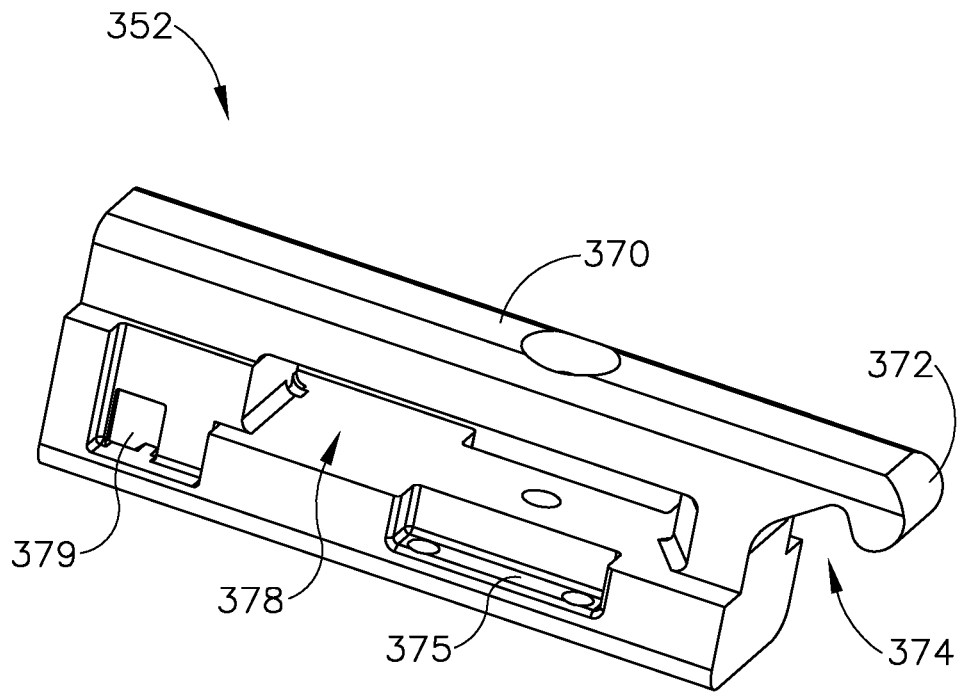
FIG. 18 depicts a top perspective view of the slider block of the firing assembly of FIG. 16.

As shown in FIGS. 15A-15E, a slider block (352) of firing assembly (350) is configured to releasably engage detent member (304) of retaining assembly (300) to provide an operator with a tactile indication of when firing assembly (350) is in a proximal home assembly, as described below. Referring briefly to FIG. 18, slider block (352) includes a block body (370) that is slidably housed between side flanges (212) of cartridge channel (206), and a finger (372) extending proximally from a proximal end of block body (370). Block finger (372) has a rounded proximal end that defines a proximal cam ramp of block finger (372), and an undercut feature (374) that defines a distal cam ramp of block finger (372).

Figure 15A:
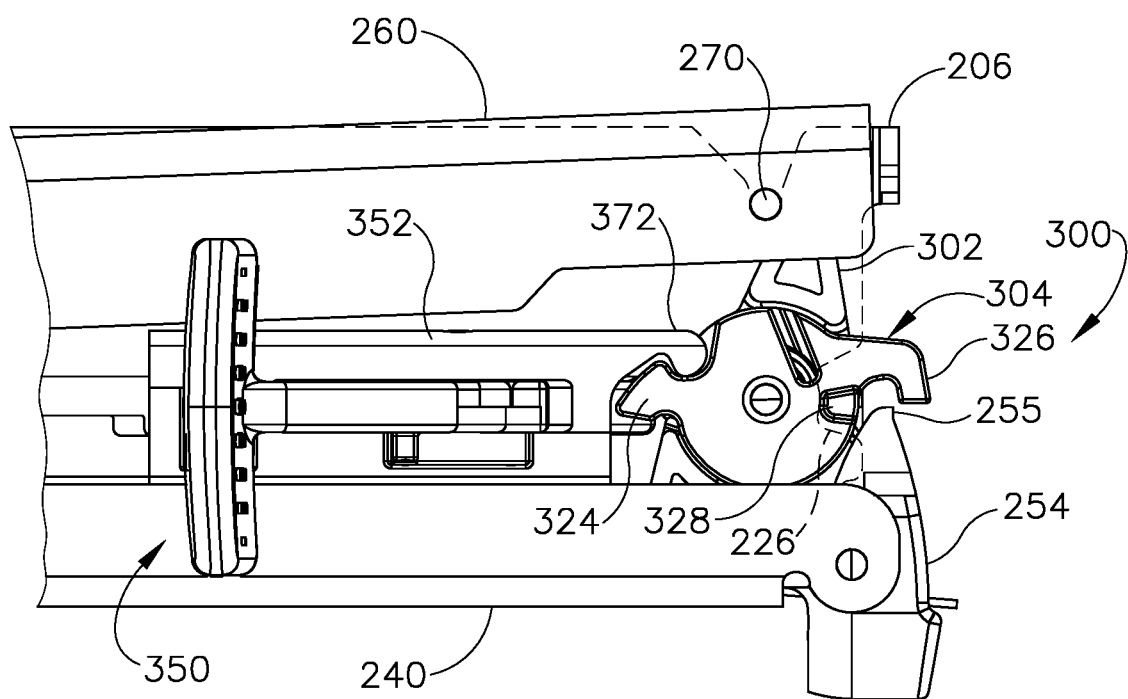
FIG. 15A depicts a side elevational view of a proximal portion of the linear surgical stapler of FIG. 6 with shrouds omitted and a proximal side portion of the cartridge channel outlined in phantom, showing a firing assembly of the linear surgical stapler in a proximal home position prior to firing.

FIG. 15A shows firing assembly (350) in a proximal home position in which slider block (352) is arranged proximally within cartridge channel (206). In this proximal position, block finger (372) hooks over and interlocks with detent finger (324) such that the proximal cam ramp of detent finger (324) contacts the distal cam ramp of block finger (372). This interaction between block finger (372) and detent finger (324) urges detent member (304) slightly in a counter-clockwise direction (in the view of FIG. 15A), against the bias of torsion spring (340), such that detent stop tab (328) is slightly spaced from the lower surface of the respective cartridge channel stop notch (226). In response, torsion spring (340) urges detent member (304) in a clockwise direction so that detent finger (324) exerts an upwardly directed force on block finger (372). This exertion of forces provides a detent engagement that releasably retains firing assembly (350), via slider block (352), in the proximal home position.

Figure 15B:
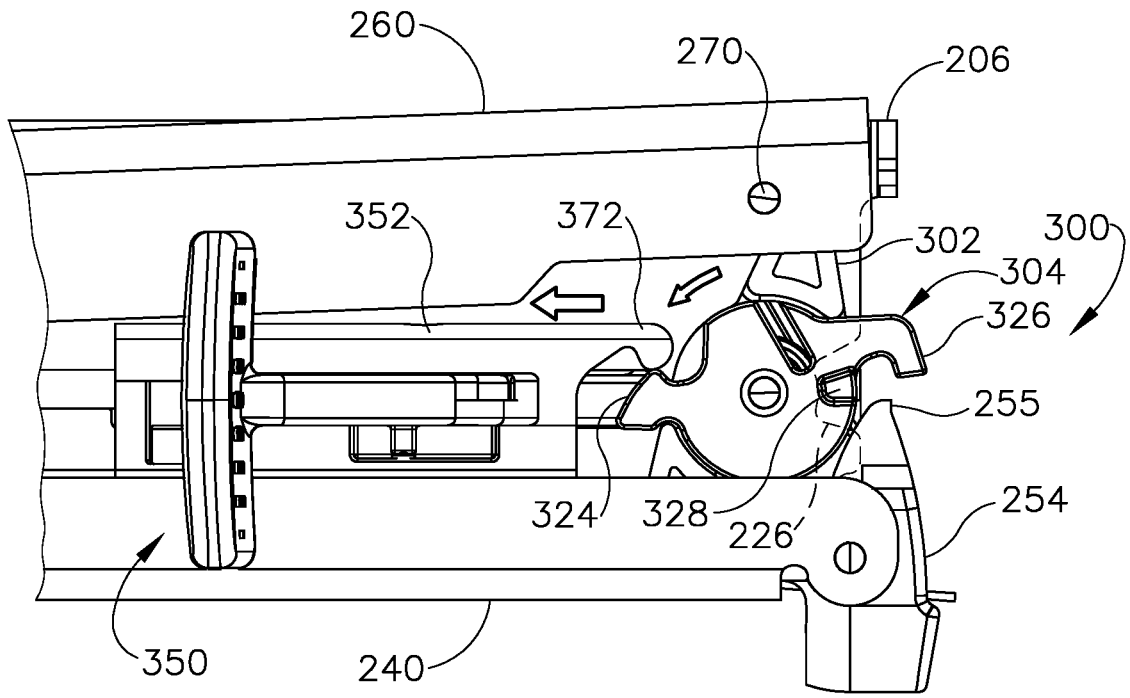
FIG. 15B depicts a side elevational view of the proximal portion of the linear surgical stapler of FIG. 15A, showing the firing assembly advancing distally during firing such that a proximal end of a slider block of the firing assembly rotates the detent member in a first direction.
Figure 15C:
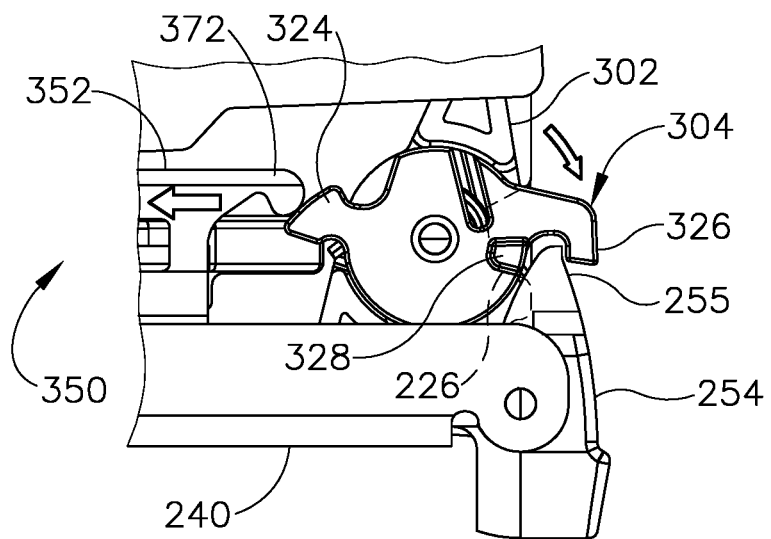
FIG. 15C depicts a side elevational view of the proximal portion of the linear surgical stapler of FIG. 15B, showing the firing assembly advancing further distally during firing such that the slider block disengages the detent member and enables the detent member to rotate in a second direction so that a clamp lever lockout feature of the detent member locks out the clamp lever latch.

As shown in FIG. 15B, when firing assembly (350) is actuated distally by an operator performing a firing stroke, block finger (372) drives detent finger (324) downwardly such that detent member (304) rotates in a counter-clockwise direction. As shown in FIG. 15C, as firing assembly (350) advances further distally, block finger (372) disengages detent finger (324) and the bias of torsion spring (340) rotates detent member (304) in a clockwise direction so that detent stop tab (328) abuts the lower surface of the respective cartridge channel stop notch (226). When detent member (304) assumes this rotational position, proximal hook element (326) of detent member (304) hooks over an upper tip (255) of clamp lever latch member (254), thereby preventing clamp lever latch member (254) from being actuated to release clamp lever (240) from cartridge channel (206). Accordingly, hook element (326) functions as a safety lockout feature that prevents clamp lever (240) from be opened unless firing assembly (350) is in the proximal home position. Advantageously, this feature ensures that stapler halves (202, 204) cannot be separated from one another while a knife member (366) (see FIG. 16) of stapler (200) is exposed through an upper deck of staple cartridge (230) during a firing stroke.

Figure 15D:
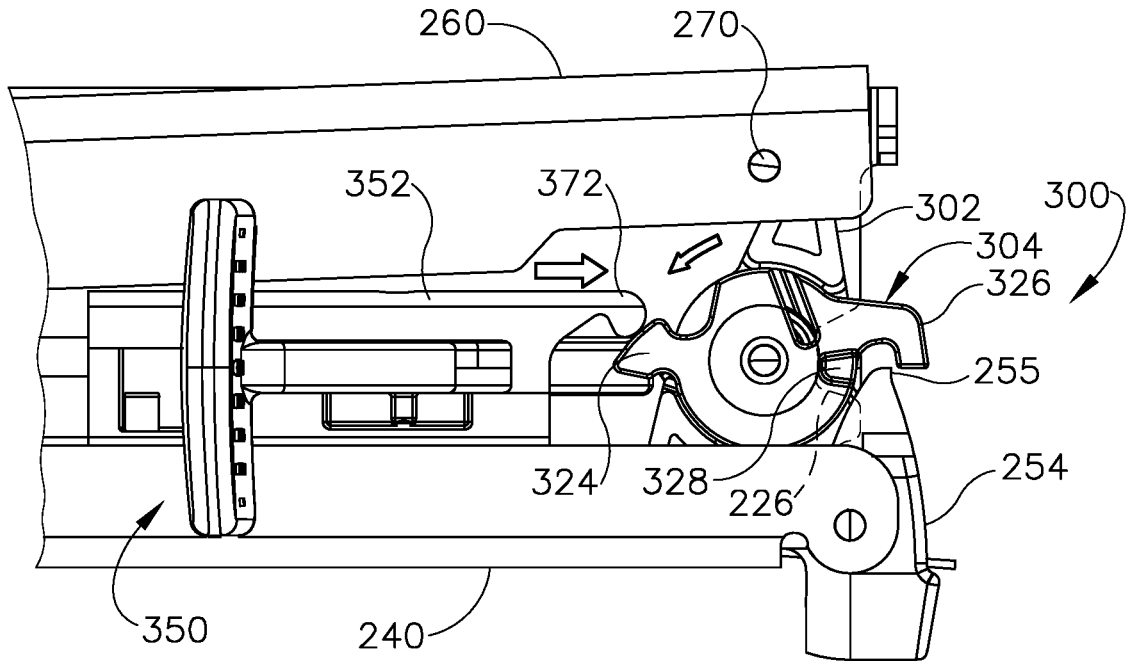
FIG. 15D depicts a side elevational view of the proximal portion of the linear surgical stapler of FIG. 15C, showing the firing assembly advancing proximally after firing such that the slider block reengages and rotates the dent member in the first direction.
Figure 15E:
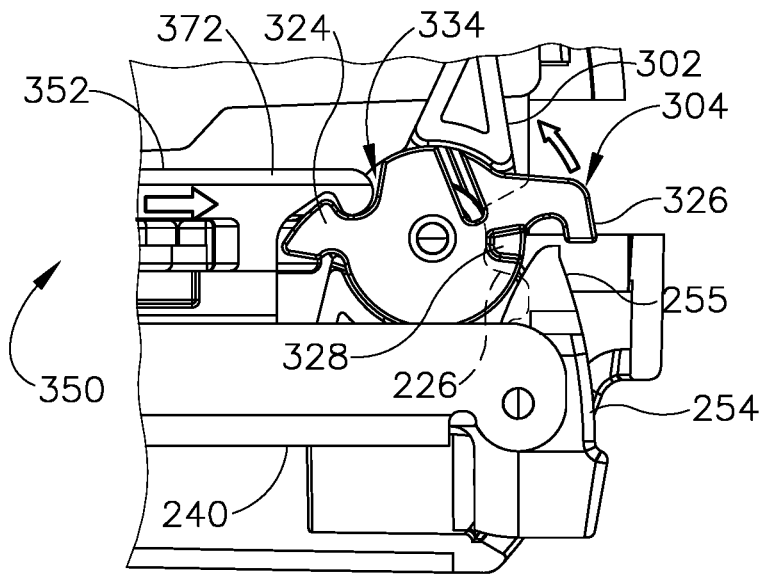
FIG. 15E depicts a side elevational view of the proximal portion of the linear surgical stapler of FIG. 15D, showing the firing assembly returned to the proximal home position in which the detent member is held in a rotational position in which the clamp lever lockout feature is disengaged from the clamp lever latch.

As shown in FIGS. 15D and 15E, after stapler (200) has been fired, firing assembly (350) is returned to its proximal home position within cartridge channel (206). As firing assembly (350) is advanced proximally, the proximal cam ramp of block finger (372) engages the distal cam ramp of detent finger (324), thereby driving detent finger (324) downwardly and rotating detent member (304) in the counter-clockwise direction against the bias of torsion spring (340). As firing assembly (350) reaches the proximal home position shown in FIG. 15E, block finger (372) settles within uppercut feature (334) of detent finger (324) and block finger (372) holds detent member (304) in a slightly counter-clockwise position such that proximal hook element (326) no longer obstructs upper tip (255) of clamp lever latch member (254). Accordingly, clamp lever latch member (254) may be actuated to disengage cartridge channel (206) and permit opening of clamp lever (240) for separation of stapler halves (202, 204). It will be appreciated that the detent interaction between detent member (304) and slider block (352) as described above provides an operator with a tactile indication of when firing assembly (350) is separated from and returned to its proximal home position, thereby signaling to the operator when it is safe to open clamp lever (240) and separate stapler halves (202, 204).

C. Firing Assembly of Linear Surgical Stapler

FIGS. 16-21 show additional details of firing assembly (350) of linear surgical stapler (200). As shown best in FIG. 16, firing assembly (350) of the present example includes a slider block (352), a pair of actuators (354, 356) (or "firing knobs") pivotably coupled to slider block (352), and a plurality of elongate beams (358, 360) extending distally from slider block (352). A pair of side beams (358) are coupled at their proximal ends to a distal end of slider block (352) and terminate distally in a pair of cam ramps (360). Cam ramps (360) are configured to actuate staple drivers (not shown) housed within staple cartridge (230) to fire staples (not shown) from cartridge (230), in a manner similar to cam ramps (106) of sled (100) described above. A center beam (362) is coupled with side beams (358) via a bridge element (364) spaced distally from slider block (352). Center beam (362) terminates distally in an angled knife member (366) having a distal cutting edge (368) configured to cut tissue clamped between the distal portions of stapler halves (202, 204). Firing assembly (350) is operable to be driven distally through cartridge channel (206) to simultaneously cut and staple tissue clamped between stapler halves (202, 204), in response to an operator pushing distally on an exposed one of actuators (354, 356) as described below.

Figure 17:
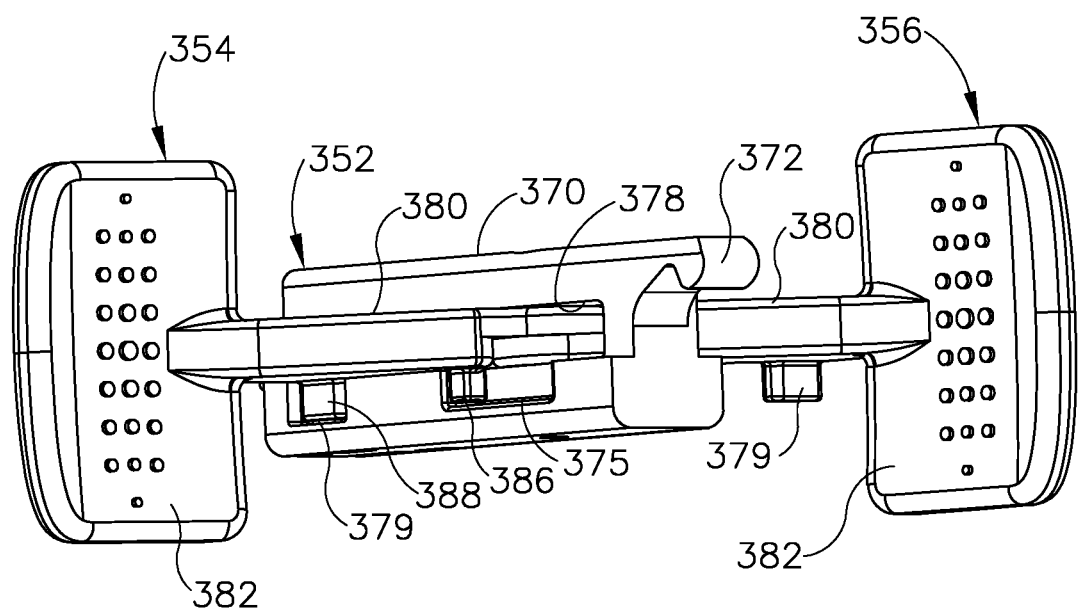
FIG. 17 depicts a proximal perspective view of the slider block and the rotatable actuators of the firing assembly of FIG. 16.
Figure 19:
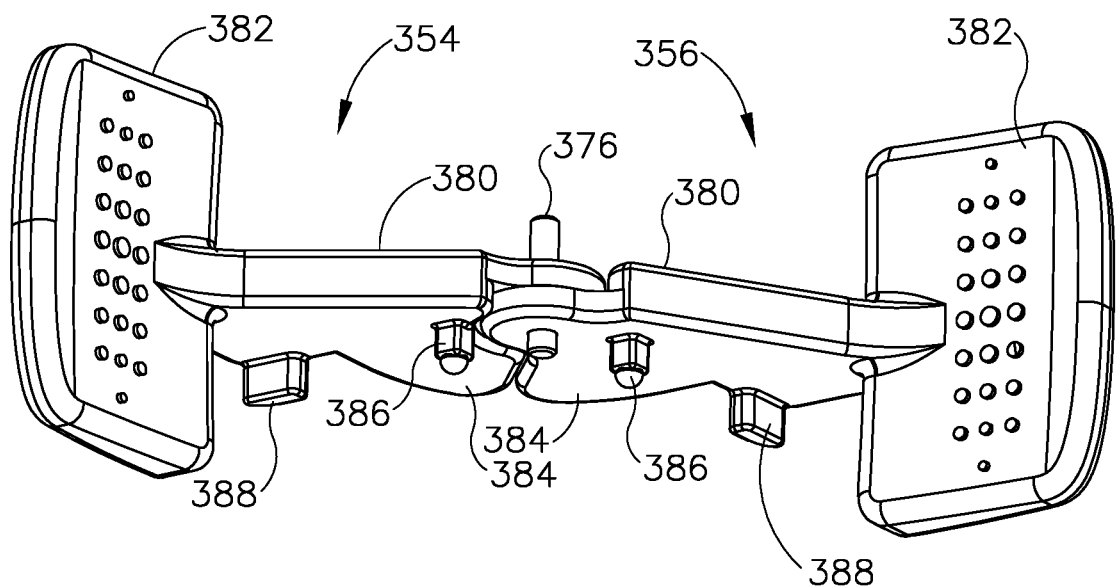
FIG. 19 depicts a bottom perspective view of the rotatable actuators of the firing assembly of FIG. 16.

As shown best in FIGS. 17-19, actuators (354, 356) are rotationally coupled to slider block body (370) with a pivot pin (376) such that each actuator (354, 356) extends outwardly from a respective lateral side of block body (370) and is configured to rotate through a lateral opening (378) formed in block body (370). Each actuator (354, 356) includes an actuator body (380) and a paddle (382) extending transversely from an outer end of actuator body (380), such that actuator bodies (380) are generally horizontal and paddles (382) are generally vertical in the orientations depicted herein. As shown in FIG. 19, each actuator body (380) includes a wedge feature (384) at its inner end that is configured to move through lateral opening (378) of block body (370). Wedge features (384) are configured to abut one another such that each actuator (354, 356) is configured automatically, rotationally retract relative to slider block (352) when the opposing actuator (354, 356) is rotationally exposed by an operator, as described in greater detail below in connection with FIGS. 20A and 20B.

As seen best in FIGS. 17 and 19, each actuator body (380) further includes a detent projection (386) and a stop tab (388) projecting downwardly from a lower surface of actuator body (380). Each detent projection (386) is configured to slidably engage a respective detent groove (375) formed in the proximal portion of a respective lateral side of slider block body (370). Each stop tab (388) is configured to be received within a recess (379) formed in the distal portion of a respective lateral side of slider block body (370). As each actuator (354, 356) rotates between a retracted rotational positional and an exposed rotational position, its detent projection (386) slides longitudinally within the respective detent groove (375). Additionally, as an actuator (354, 356) is rotated from its exposed rotational position to its retracted rotational position, its stop tab (388) is received within and abuts an inner side wall of the respective recess (379).

Actuators (354, 356) of linear surgical stapler (200) are configured to enable dual-sided firing of stapler (200) such that stapler (200) may be fired by driving an actuator (354, 356) distally along either lateral side of stapler (200).

Actuators (354, 356) are further configured such that at least one actuator (354, 356) remains retracted at all times to prevent an unused actuator (354, 356) from interfering with an operator's ability to securely grip stapler (200) with a supporting hand while firing stapler (200) with a firing hand. As described below, each actuator (354, 356) of the present version is rotatable relative to slider block (352) by approximately 90 degrees between a retracted rotational position and an exposed rotational position.

Figure 20A:
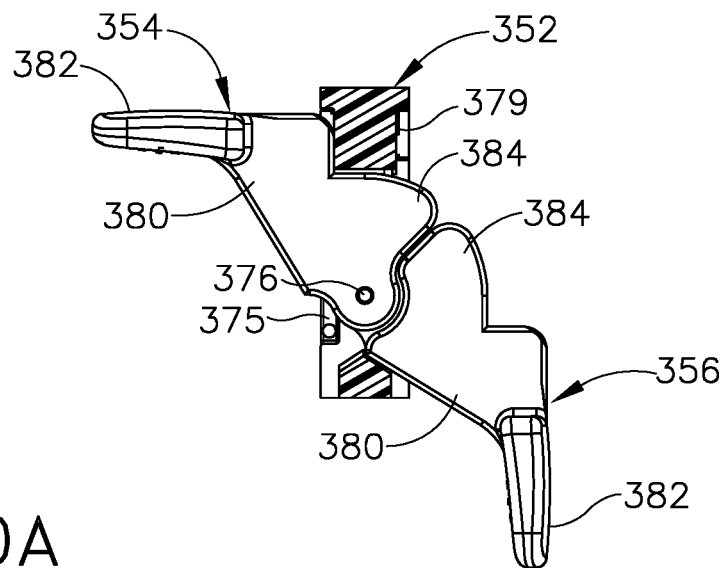
FIG. 20A depicts a top cross-sectional view of the slider block and rotatable actuators of the firing assembly of FIG. 16, showing the actuators in a first configuration in which the first actuator is in an extended rotational position and the second actuator is in a retracted rotational position.

FIG. 20A shows first actuator (354) in an exposed rotational position in which its paddle (382) is oriented distally and extends transversely to a longitudinal axis of firing assembly (350), and second actuator (356) in a retracted rotational position in which its paddle (382) is oriented proximally and extends parallel to the longitudinal axis. In this configuration, an operator may grip, with a first hand, the second lateral side of stapler (200) along which paddle (382) of second actuator (356) is retracted, and simultaneously drive with a second hand the exposed paddle (382) of first actuator (354) distally to perform a firing stroke.

Figure 20B:
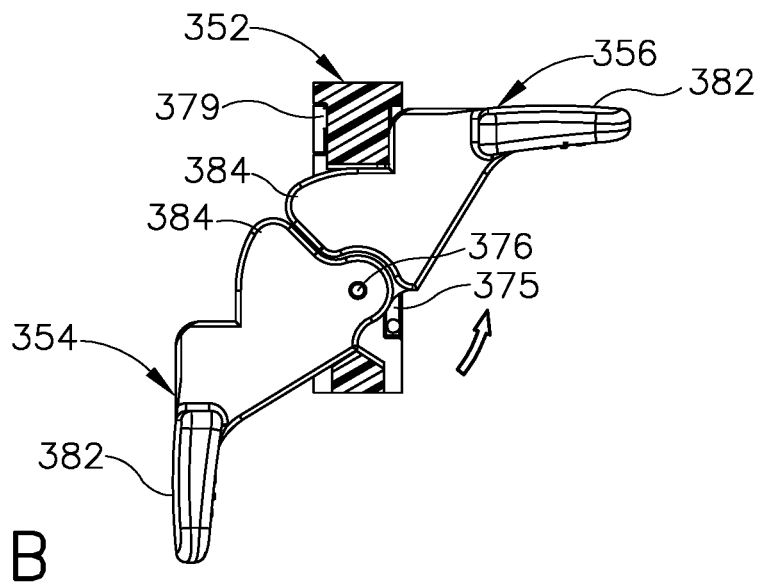
FIG. 20B depicts a top cross-sectional view of the slider block and actuators of the firing assembly of FIG. 16, showing the actuators in a second configuration in which the first actuator is retracted and the second actuator is extended.

FIG. 20B shows actuators (354, 356) in an opposite orientation achieved by driving paddle (382) of retracted second actuator (356) distally to rotate second actuator body (380) about pin (376) such that wedge feature (384) of second actuator (356) drives against wedge feature (384) of first actuator (354). This interaction causes first actuator (354) to automatically rotate from an exposed rotational position to a retracted rotational position, shown in FIG. 20B. In this configuration, an operator grips, with a first hand, the first lateral side of stapler (200) along which paddle (382) of first actuator (354) is retracted, and simultaneously drive with a second hand the exposed paddle (382) of second actuator (356) distally to perform a firing stroke. It will be appreciated that second actuator (356) may also automatically rotate from its exposed rotational position to its retracted rotational position in response to rotation of first actuator (354).

Figure 20C:
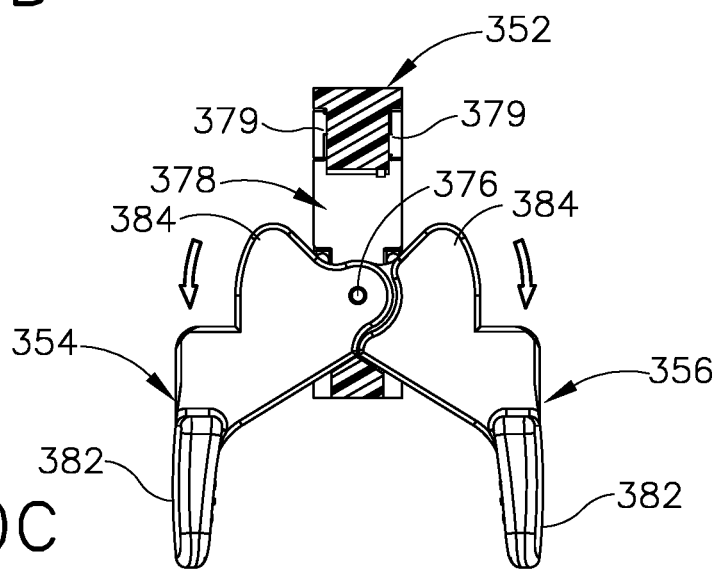
FIG. 20C depicts a top cross-sectional view of the slider block and actuators of the firing assembly of FIG. 16, showing the actuators in a third configuration in which both actuators are retracted.

FIG. 20C shows both actuators (354, 356) in retracted rotational positions in which both paddles (382) are oriented proximally such that they extend generally parallel to the longitudinal axis of firing assembly (350). Such a configuration may provide surgical stapler (200) with a compact profile suitable for device packaging and other storage or transportation purposes, for example.

Figure 21:
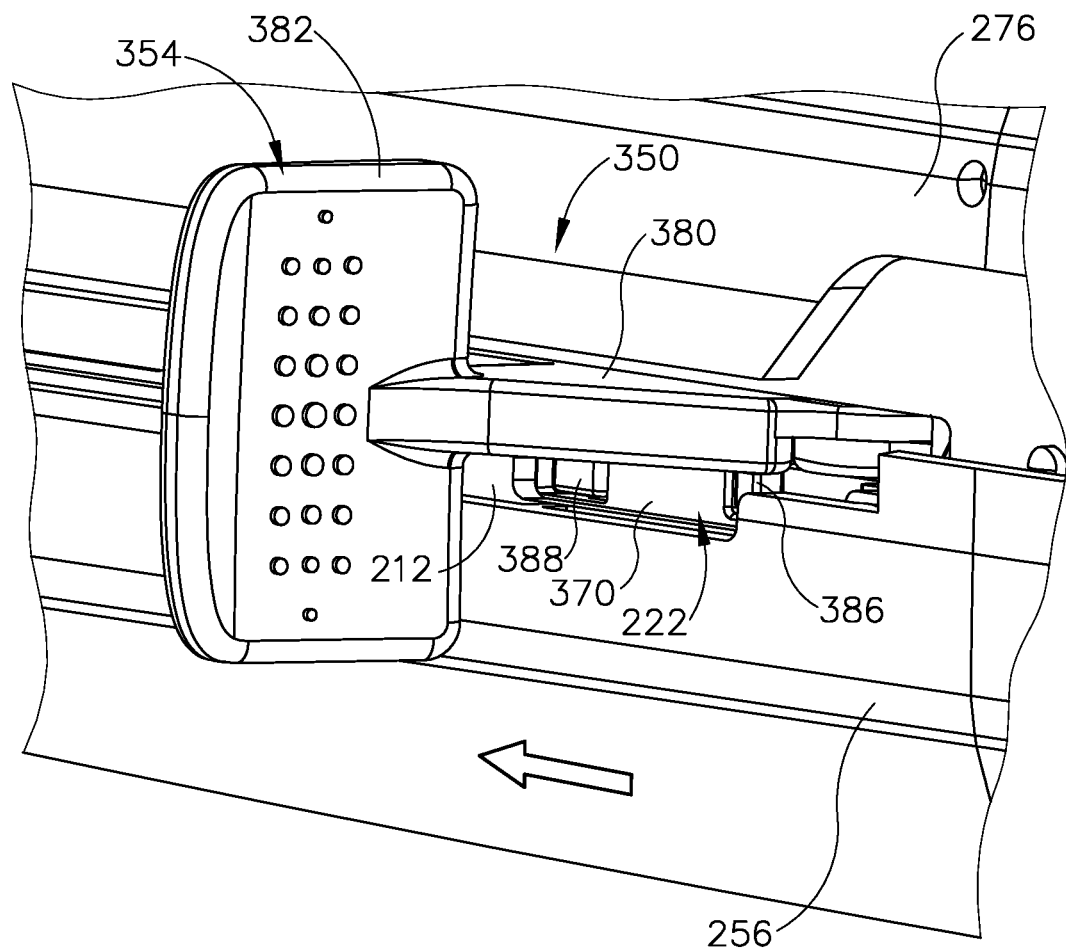
FIG. 21 depicts an enlarged perspective view of a proximal portion of the linear surgical stapler of FIG. 6, showing a lower tab of an actuator of the firing assembly of FIG. 16 being constrained against an inner surface of the cartridge channel as the firing assembly is advanced distally.

As shown in FIGS. 7 and 21, the proximal portion of each longitudinal firing slot (222) of cartridge channel (206) is suitably shaped to permit the respective actuator (354, 356) to rotate between its retracted and exposed positions while firing assembly (350) is in its proximal home position. Once firing assembly (350) is actuated distally during a firing stroke, firing slots (222) prevent actuators (354, 356) from rotating until firing assembly (350) is returned to its proximal home position following completion of the firing stroke. For instance, FIG. 21 shows first actuator (354) in an exposed position and being driven distally through a respective longitudinal firing slot (222) such that its stop tab (388), and subsequently its detent projection (386), are captured between slider block body (370) and a confronting inner surface of the respective side flange (212) of cartridge channel (206). Accordingly, stop tab (388) and detent projection (386) of first actuator (354) become constrained to prevent unintentional rotation of first actuator (354) from its exposed position to its retracted position while stapler (200) is being fired. It will be understood that second actuator (356) is constrained in a similar manner by slider block body (370) and the adjacent cartridge channel side flange (212) when second actuator (356) is in the exposed position and is being driven distally to fire stapler (200).

III. Exemplary Alternative Slider Block and Actuator Assemblies

In some instances, it may be desirable to provide linear surgical stapler (200) with rotatable actuators that are configured to be oriented in exposed rotational positions simultaneously, unlike actuators (354, 356) described above. The exemplary alternative actuators (402, 404, 432, 434) described below exhibit such functionality.

Figure 22:
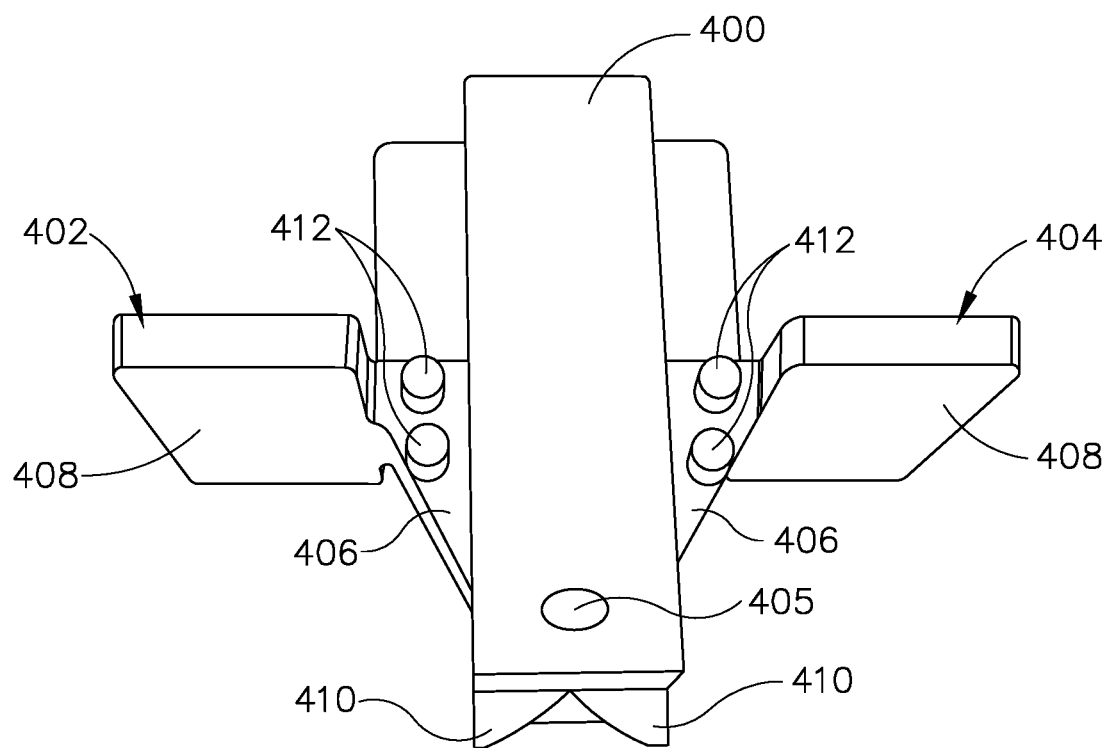
FIG. 22 depicts a top perspective view of another exemplary slider block and a pair of rotatable actuators, showing both of the actuators in extended rotational positions.
Figure 23:
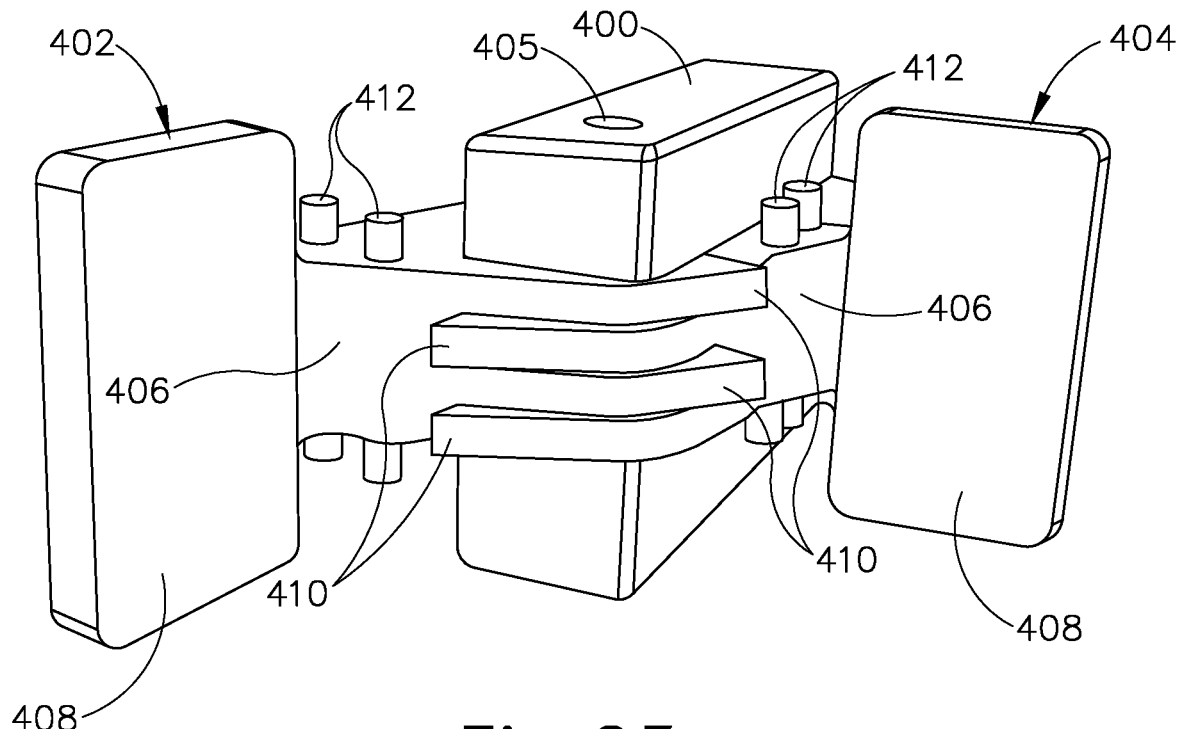
FIG. 23 depicts a proximal perspective view of the firing assembly of FIG. 22, showing the first actuator in a retracted position and the second actuator in an extended position.

FIGS. 22 and 23 show another exemplary slider block (400) and a pair of actuators (402, 404) (or "firing knobs") suitable for use with linear surgical stapler (200). Slider block (400) and actuators (402, 404) are similar to slider block (352) and actuators (354, 356) described above in that actuators (402, 404) are rotatably coupled with slider block (400) about a shared vertical pivot axis defined by a pivot pin (405). Additionally, each actuator (402, 404) is rotatable by approximately 90 degrees between an exposed rotational position and a retracted rotational position to provide dual-sided firing. Each actuator (402, 404) includes a generally triangular actuator body (406) having an inner end that is rotatably coupled with slider block (400) and outer end from which a paddle (408) extends transversely. Though not shown, slider block (400) and actuators (402, 404) may include detent features that provide an operator with a tactile indication of the rotational position of each actuator (402, 404). In some versions, such detent features may be similar to those of slider block (352) and actuators (354, 356) described above. In some versions, such detent features may be supplemented or substituted with other suitable friction-inducing elements, such as o-rings, to enhance tactile feel for an operator.

As shown best in FIGS. 22 and 23, the inner end of each actuator body (406) includes a plurality of laterally extending, pointed arms (410) configured to overlap and mesh with similar pointed arms (410) of the opposing actuator body (406). Pointed arms (410) of each actuator (402, 404) are configured such that when a given actuator (402, 404) is rotated from an exposed rotational position to a retracted rotational position, its pointed arms (410) engage the outer end of the opposing actuator body (406) and automatically rotate the opposing actuator (402, 404) from a retracted position to an extended position. In other words, in the present example, each actuator (402, 404) is configured to rotatably drive the opposing actuator (402, 404) when actuators (402, 404) are rotationally offset from one another by 90 degrees.

Figure 24A:
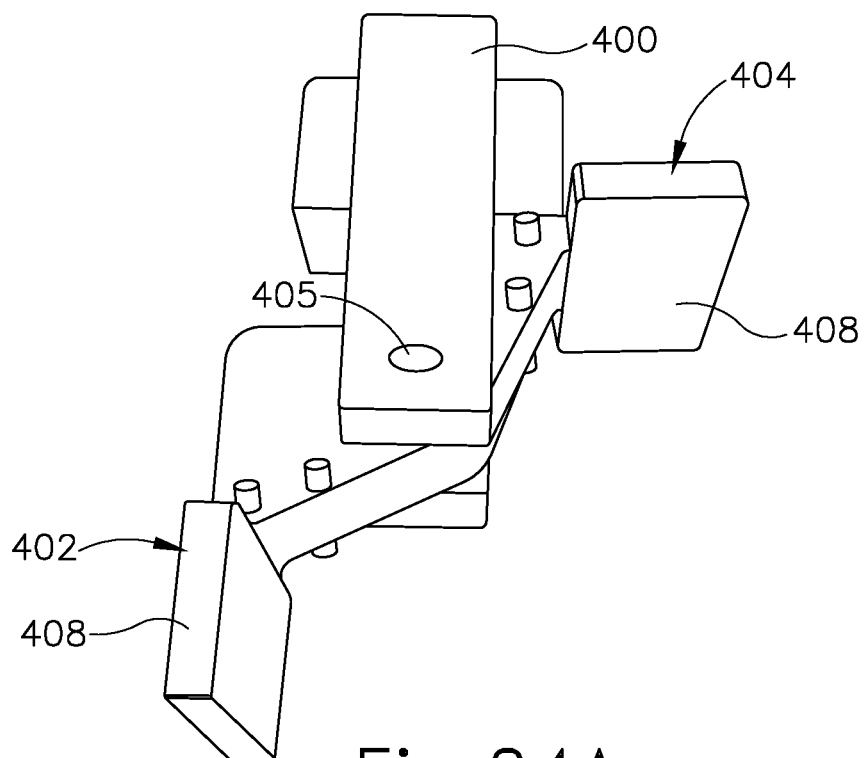
FIG. 24A depicts a top perspective view of the slider block and actuators of FIG. 22, showing the first actuator in a retracted position and the second actuator in an extended position.
Figure 24B:
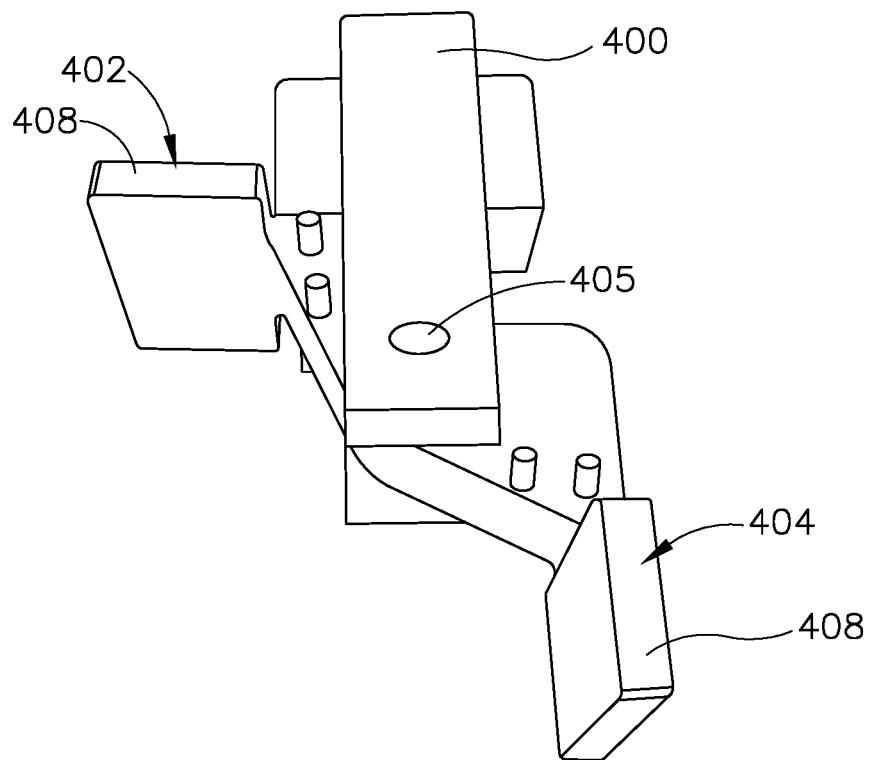
FIG. 24B depicts a top perspective view of the firing assembly of FIG. 22, showing the first actuator in an extended position and the second actuator in a retracted position.
Figure 25A:
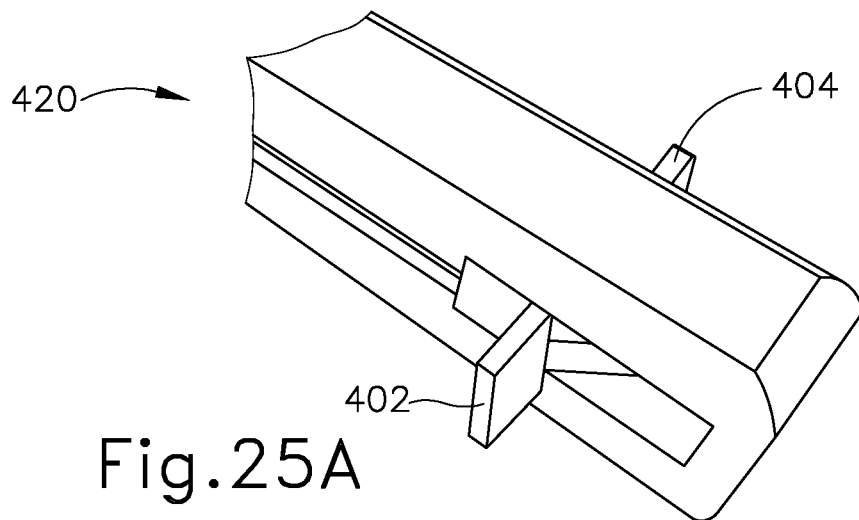
FIG. 25A depicts a top perspective view of a proximal portion of an exemplary linear surgical stapler that incorporates the slider block and actuators of FIG. 22, showing the actuators in the configuration of FIG. 22 in which both actuators are extended.
Figure 25B:
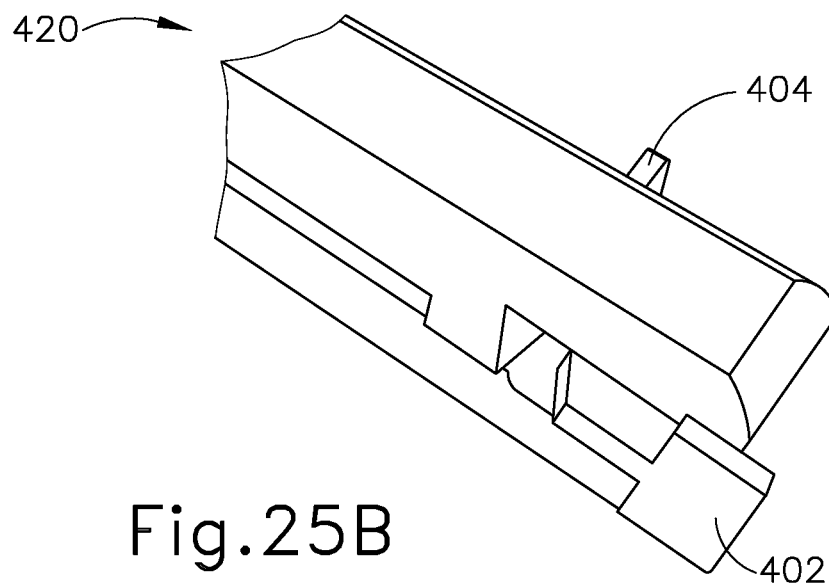
FIG. 25B depicts a top perspective view of the proximal portion of the linear surgical stapler of FIG. 25A, showing the actuators in the configuration of FIG. 24A in which the first actuator is retracted and the second actuator is extended.
Figure 25C:
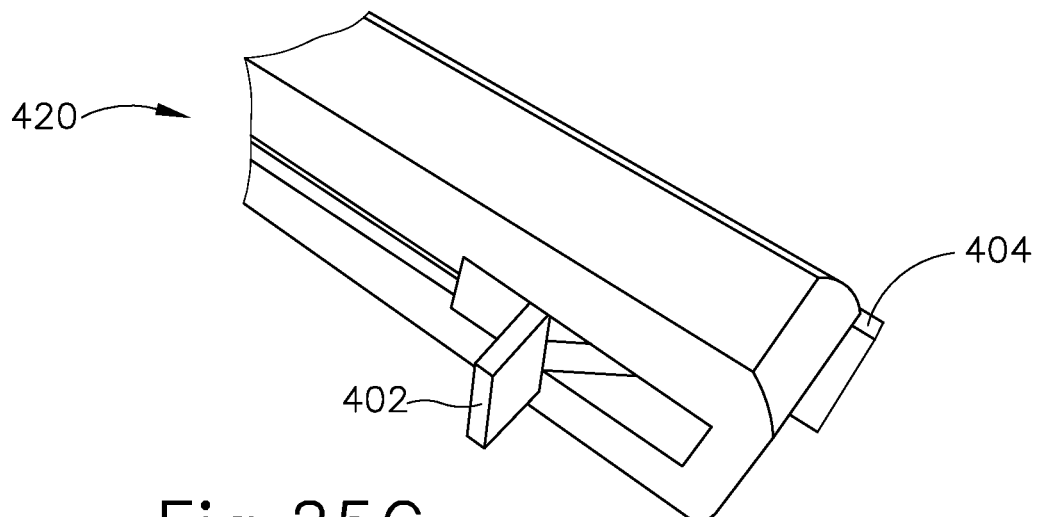
FIG. 25C depicts a top perspective view of the proximal portion of the linear surgical stapler of FIG. 25A, showing the actuators in the configuration of FIG. 24B in which the first actuator is extended and the second actuator is retracted.

FIG. 24A shows actuators (402, 404) in an exemplary configuration in which first actuator (402) is retracted and second actuator (404) is extended. FIG. 24B shows actuators (402, 404) in an opposite configuration in which first actuator (402) is extended and second actuator (404) is retracted, which may be achieved from the configuration shown in FIG. 24A simply by rotating second actuator (404) from its extended position to its retracted position. FIG. 25A shows the proximal end of an exemplary linear surgical stapler (420) that incorporates slider block (400) and actuators (402, 404), showing the slider block (400) in a proximal home position with both actuators (402, 404) extended, similar to FIG. 22. FIG. 25B shows the proximal end of stapler (420) with slider block (400) in the proximal home position with first actuator (402) retracted and second actuator (404) extended, similar to FIG. 24A. FIG. 25C shows the proximal end of stapler (420) with slider block (400) in the proximal home position with first actuator (402) extended and second actuator (404) retracted, similar to FIG. 24B.

Figure 26:
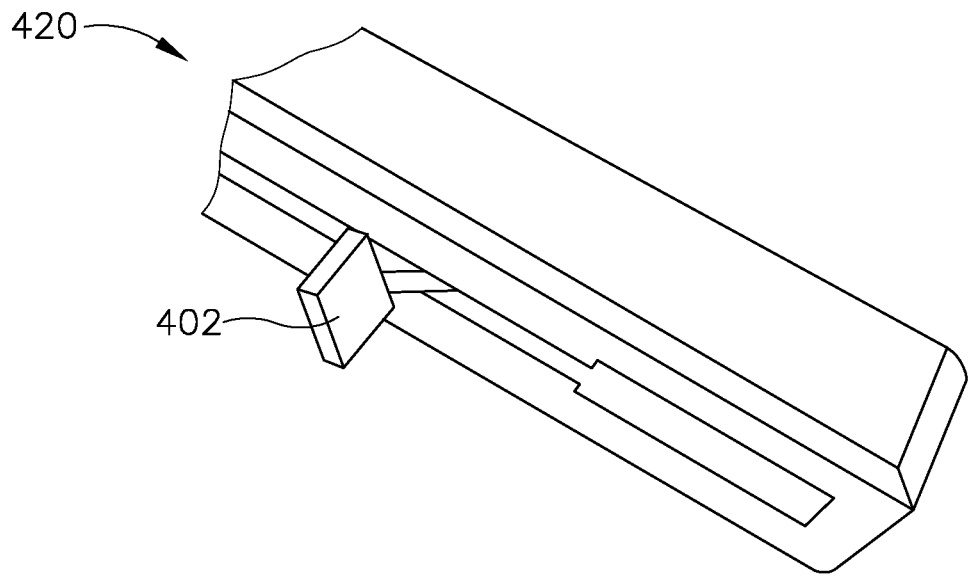
FIG. 26 depicts a top perspective view of the proximal portion of the linear surgical stapler of FIG. 22, showing the firing assembly advanced distally for firing with the first actuator extended and the second actuator retracted.
Figure 27:
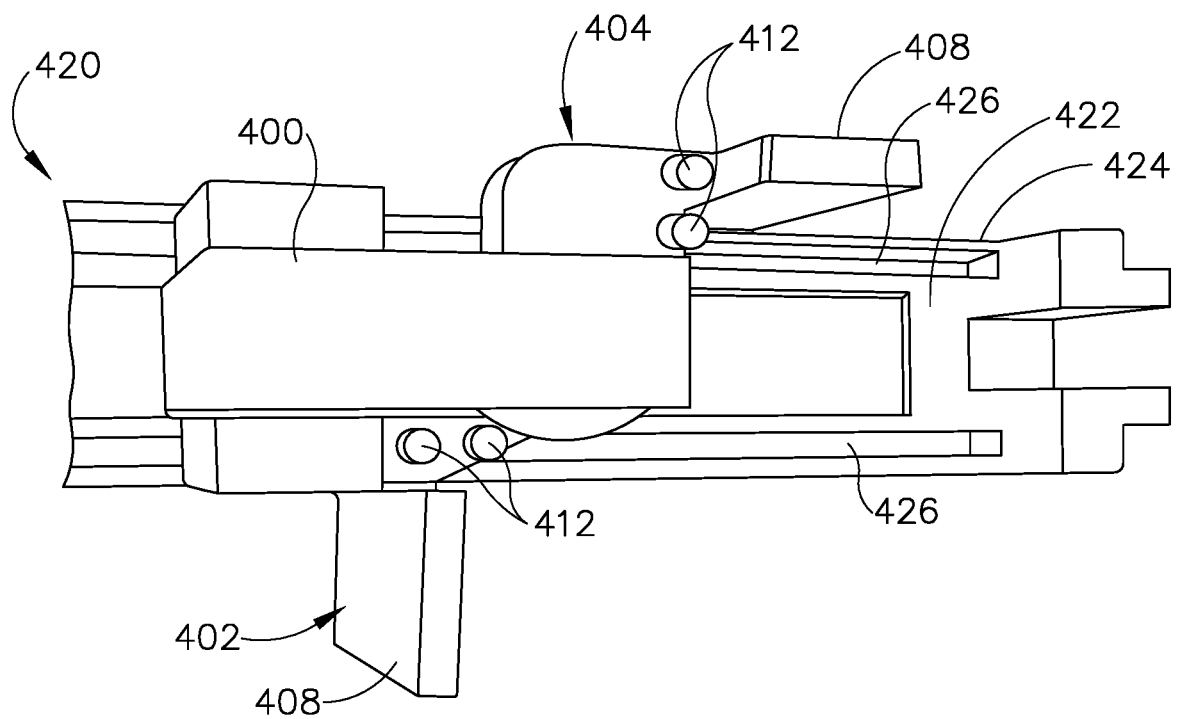
FIG. 27 depicts a top perspective view of the firing assembly and a cartridge channel of the linear surgical stapler of FIG. 26, showing the firing assembly advanced to a distal position.

FIG. 26 shows first actuator (402) in the extended rotational position and in a distal longitudinal position after having been translated distally with slider block (400) to fire stapler (420). As shown best in FIGS. 22, 23, and 27, each actuator (402, 404) includes a pair of vertically extending projections (414) arranged at an outer end of actuator body (406). Vertical projections (412) of each actuator (402, 404) are configured to track longitudinally within a respective guide channel (426) defined between confronting lateral sides of a cartridge channel (422) and a cartridge half shroud (424) when slider block (400) and actuators (402, 404) are driven distally. This tracking of vertical projections (412) within guide channels (426) prevents unintentional rotation of actuators (402, 404) during a firing stroke. As demonstrated by projections (412) of first actuator (402) in FIG. 27, projections (412) are aligned parallel to the longitudinal axis of cartridge channel (422) when the respective actuator (402, 404) is in the exposed rotational position, such that both projections (412) are captured and track within the guide channel (426). As demonstrated by projections (412) of second actuator (404) in FIG. 27, only one of the projections (412) of an actuator (402, 404) tracks within the respective guide channel (426) when an actuator (402, 404) is in the retracted rotational position.

Figure 28:
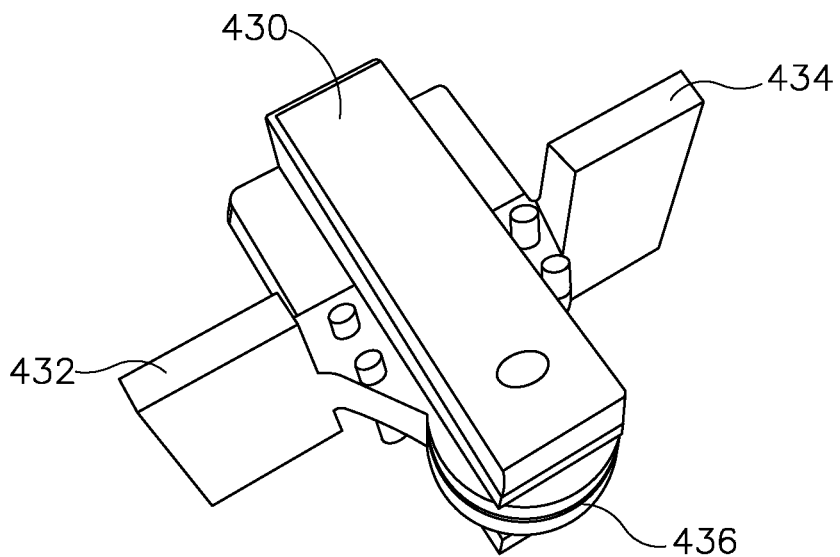
FIG. 28 depicts a top perspective view of another exemplary firing assembly having a slider block and a pair of rotatable actuators, showing both of the actuators in extended rotational positions.
Figure 29:
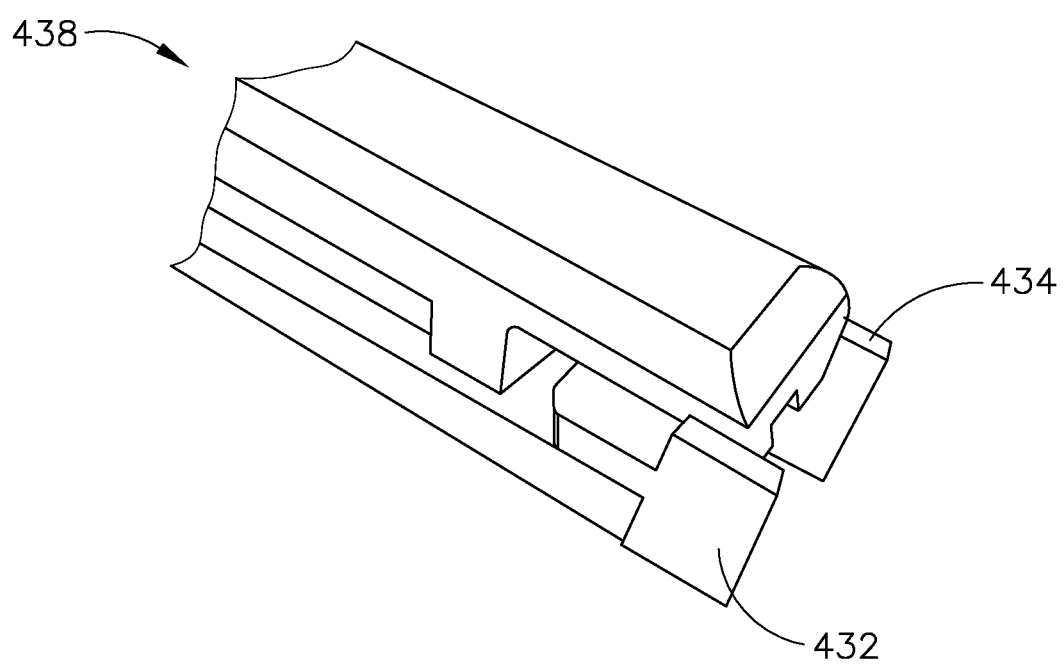
FIG. 29 depicts a top perspective view of a proximal portion of an exemplary linear surgical stapler that incorporates the slider block and rotatable actuators of FIG. 28, showing the actuators in a configuration in which both actuators are retracted.

FIG. 28 shows another exemplary slider block (430) and a corresponding pair of rotatable actuators (432, 434) suitable for use with linear surgical stapler (200). Slider block (430) and actuators (432, 434) are similar to slider block (400) and actuators (402, 404) described above, except that each actuator (432, 434) has a rounded inner end (436) that omits pointed arms (410). Consequently, rotation of an actuator (432, 434) from its extended rotational position to its retracted rotational position while the opposing actuator (432, 434) is retracted does not operate to automatically extend the opposing actuator (432, 434). Accordingly, unlike actuators (402, 404), actuators (432, 434) are configured to both assume a retracted rotational position simultaneously, as exemplified by linear surgical stapler (438) shown in FIG. 29.

IV. Exemplary Alternative Detent Member and Slider Block Assembly

In some instances, it may be desirable to configure the firing assembly of a linear surgical stapler such that it includes a slider block that omits proximally extending projections, unlike slider block (352) of firing assembly (350) described above. The exemplary alternative linear surgical stapler (440) described below includes a firing assembly that is configured in such a manner.

FIGS. 30 and 31A-31E show the proximal portion of another exemplary linear surgical stapler (440) having a cartridge half (442) and an anvil half (444) configured to be releasably coupled together to clamp tissue therebetween and simultaneously cut and staple the clamped tissue. Stapler (440) may be generally similar to stapler (200) described above, except as otherwise described below. Cartridge half (442) includes an elongate cartridge channel (446) and a clamp lever (448) coupled with cartridge channel (446) and configured to pivot between open and closed positions to clamp stapler halves (442, 444) together. Cartridge half (442) further includes, among other features, a firing assembly (450) and a proximal retaining assembly (452) supported by a proximal frame portion of cartridge channel (446). Anvil half (444) includes, among other features, an elongate anvil channel (454) and a proximal pin (456) coupled to a proximal end of anvil channel (454) and configured to be engaged by proximal retaining assembly (452) of cartridge half (442), as described below.

Figure 30:
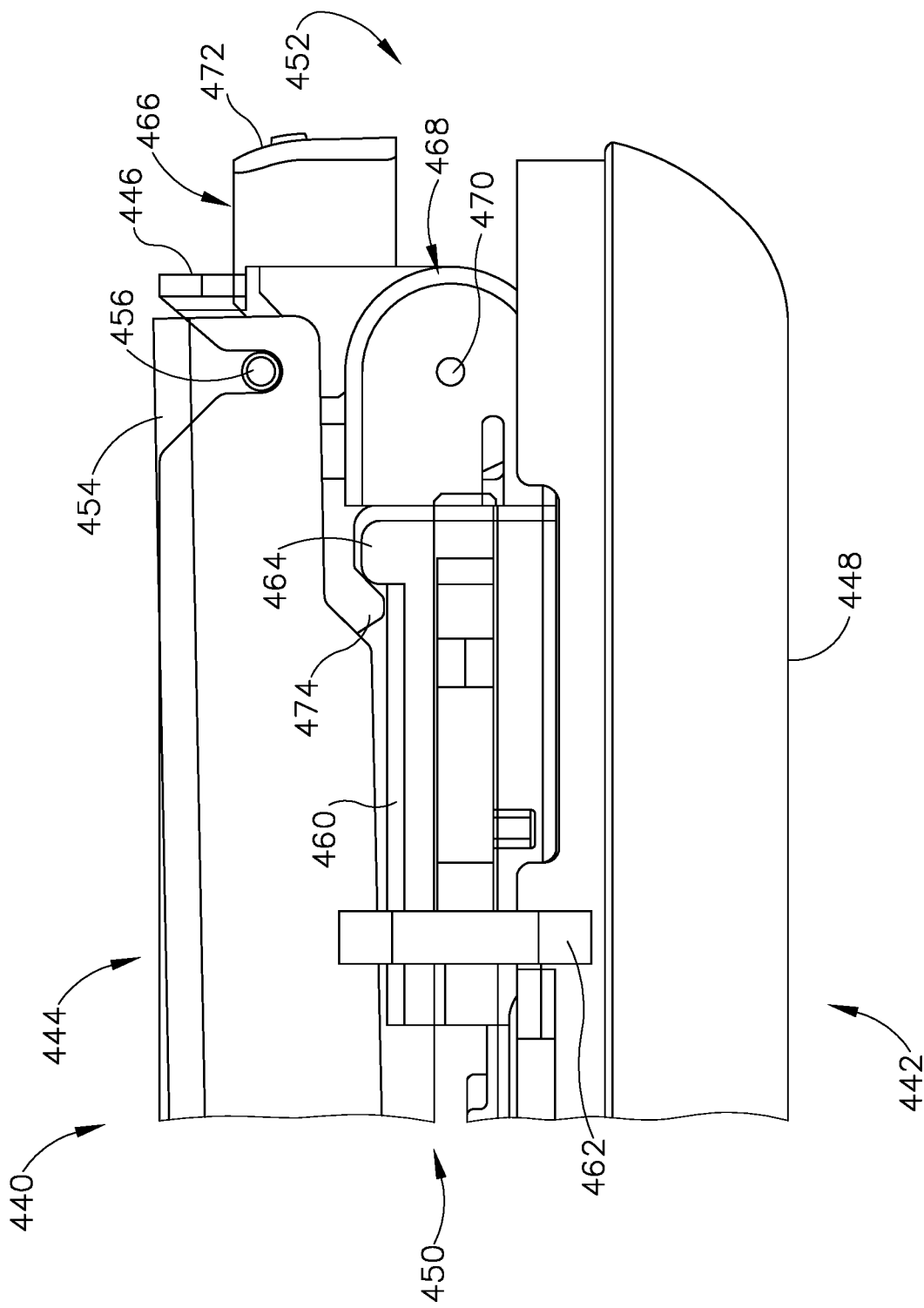
FIG. 30 depicts a side elevational view of a proximal portion of another exemplary linear surgical stapler having a cartridge half and an anvil half, with an anvil shroud and a side portion of a cartridge channel being omitted.

Firing assembly (450) of linear surgical stapler (440) is similar to firing assembly (350) of stapler (200) in that firing assembly (450) includes a slider block (460) and a pair of rotatable actuators (462) coupled with slider block (460), with only one actuator (462) being shown in FIG. 30. Similar to actuators (354, 356), each actuator (462) is rotatable relative to slider block (460) between a retracted rotational position and an exposed rotational position. A proximal end of slider block (460) includes an upwardly extending finger (464) having rounded proximal and distal ends defining respective proximal and distal cam ramps configured to releasably engage proximal retaining assembly (452), as described below.

Retaining assembly (452) of linear surgical stapler (440) is similar to retaining assembly (300) of stapler (200) in that retaining assembly (452) includes an anvil latch member (466) configured to releasably couple a proximal end of cartridge half (442) with a proximal end of anvil half (444), and a detent member (468) configured to releasably retain firing assembly (450) in a proximal home position. Anvil latch member (466) and detent member (468) are rotatably coupled with a proximal end of cartridge channel (446) about a shared rotational axis defined by a laterally extending pivot pin (470). Additionally, anvil latch member (466) and detent member (468) are resiliently biased in opposite rotational directions by a resilient member (not shown) similar to torsion spring (340). In particular, in the view shown in FIG. 30, detent member (468) is biased in a counter-clockwise direction and anvil latch member (466) is biased in a clockwise direction. Anvil latch member (466) includes a latch feature (not shown), which may be similar to latch finger (310) of anvil latch member (302), configured to releasably capture proximal pin (456) of anvil half (444) to couple anvil half (444) with cartridge half (442). Anvil latch member (466) further includes a proximally extending release button (472) configured to selectively disengage the latch feature from proximal pin (456) to permit separation of stapler halves (442, 444). Detent member (468) includes a distally extending finger (474) having a distal tip that tapers downwardly so as to define opposed proximal and distal cam ramps configured to engage slider block finger (464), as described below.

Figure 31A:
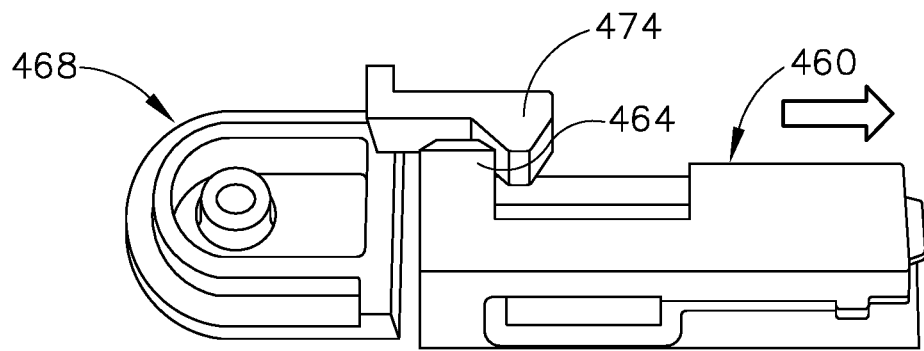
FIG. 31A depicts a side perspective view of a slider block and a detent member of the linear surgical stapler of FIG. 30, showing the slider block in a proximal home position in which the slider block engages the detent member.
Figure 31B:
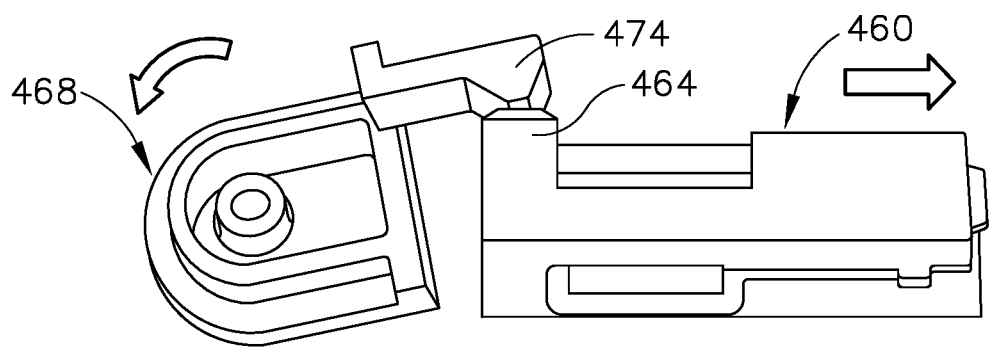
FIG. 31B depicts a side perspective view of the slider block and the detent member of FIG. 31A, showing the slider block being advanced distally and causing the detent member to rotate in a first direction.
Figure 31C:
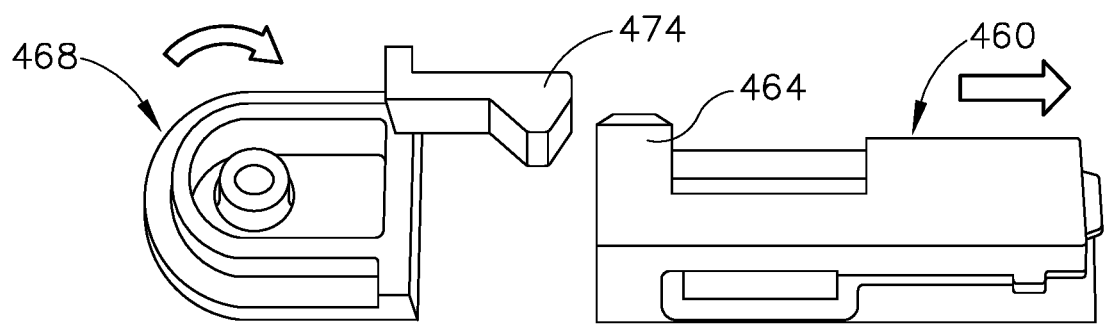
FIG. 31C depicts a side perspective view of the slider block and the detent member of FIG. 31B, showing the slider block being advanced further distally to the point of disengaging and allowing the detent member to rotate in a second direction.
Figure 31D:
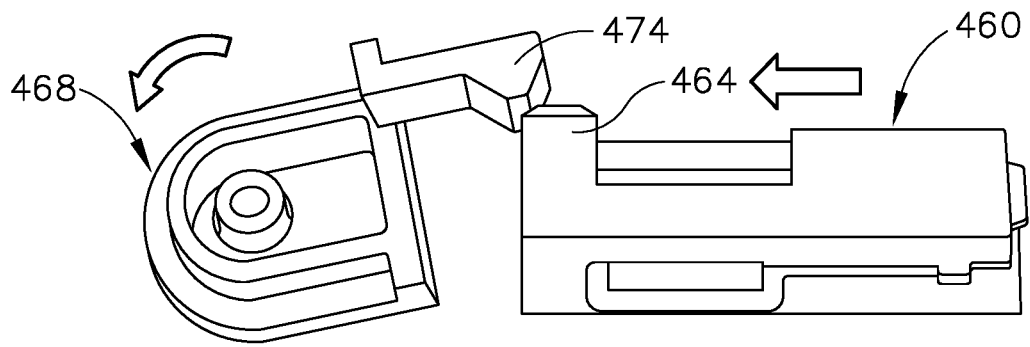
FIG. 31D depicts a side perspective view of the slider block and the detent member of FIG. 31C, showing the slider block being advanced proximally to reengage the detent member and cause the detent member to rotate in the first direction.
Figure 31E:
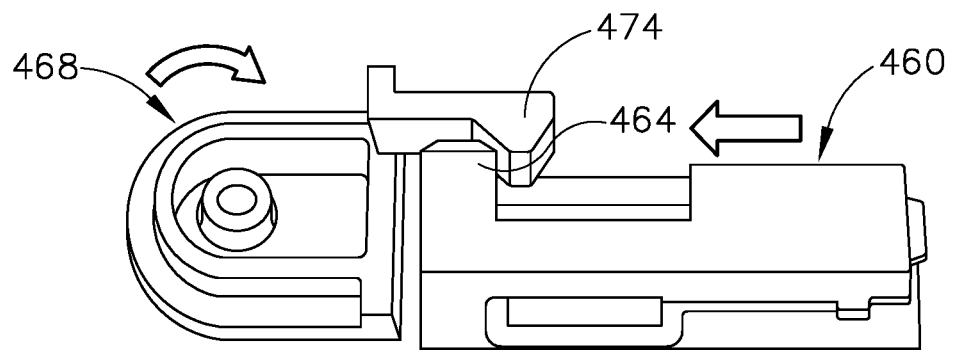
FIG. 31E depicts a side perspective view of the slider block and the detent member of FIG. 31D, showing the slider block returned to the proximal home position and the detent member after having rotated in the second direction to releasably capture the slider block.

FIGS. 31A-31E show interactions between slider block (460) and detent member (468) during firing of linear surgical stapler (440). FIG. 31A shows slider block (460) in a proximal home position in which detent finger (474) overlies an upper end of slider block finger (464). As slider block (460) is driven distally during a firing stroke, the proximal rounded end of slider block finger (464) pushes distally on the proximal cam ramp of detent finger (474), thereby causing detent member (468) to rotate such that detent finger (474) moves upwardly, as shown in FIG. 31B. As slider block (460) advances further distally, detent finger (474) disengages slider block finger (464) and detent member (468) returns to its original rotational position, as shown in FIG. 31C. As shown in FIGS. 31D and 31E, when slider block (460) is retracted proximally after stapler (440) is fired, the rounded proximal end of slider block finger (464) engages the distal cam surface of detent finger (474). This causes detent member (468) to rotate such that detent finger (474) moves upwardly and receives slider block finger (464) once again as slider block (460) returns to the proximal home position shown in FIG. 31E. Advantageously, the above described detent interaction between detent finger (474) and slider block finger (464) provides the operator with a tactile indication of when firing assembly (450) is advanced distally from and returned proximally to its proximal home position.

V. Exemplary Linear Surgical Staplers Having Concealable Anvil Release Features As described above, linear surgical stapler (200) includes a first releasable latching feature in the form of anvil latch member (302) that releasably couples the proximal end of anvil half (204) with the proximal end of cartridge half (202). Stapler (200) further includes a second releasable latching feature in the form of clamp lever latch member (254) that releasably maintains clamp lever (240) in the closed position. Cartridge half (202) is configured such that release button (312) of anvil latch member (302) is concealed by clamp lever (240) while clamp lever (240) is in the closed position, thereby preventing unwanted confusion for an operator between anvil release button (312) and clam lever latch member (254) during a surgical procedure. The exemplary linear surgical staplers (480, 500) described below present alternative configurations that conceal an anvil half release feature when the clamp lever is closed to prevent unwanted confusion between an anvil half release feature and a clamp lever release feature.

Figure 32A:
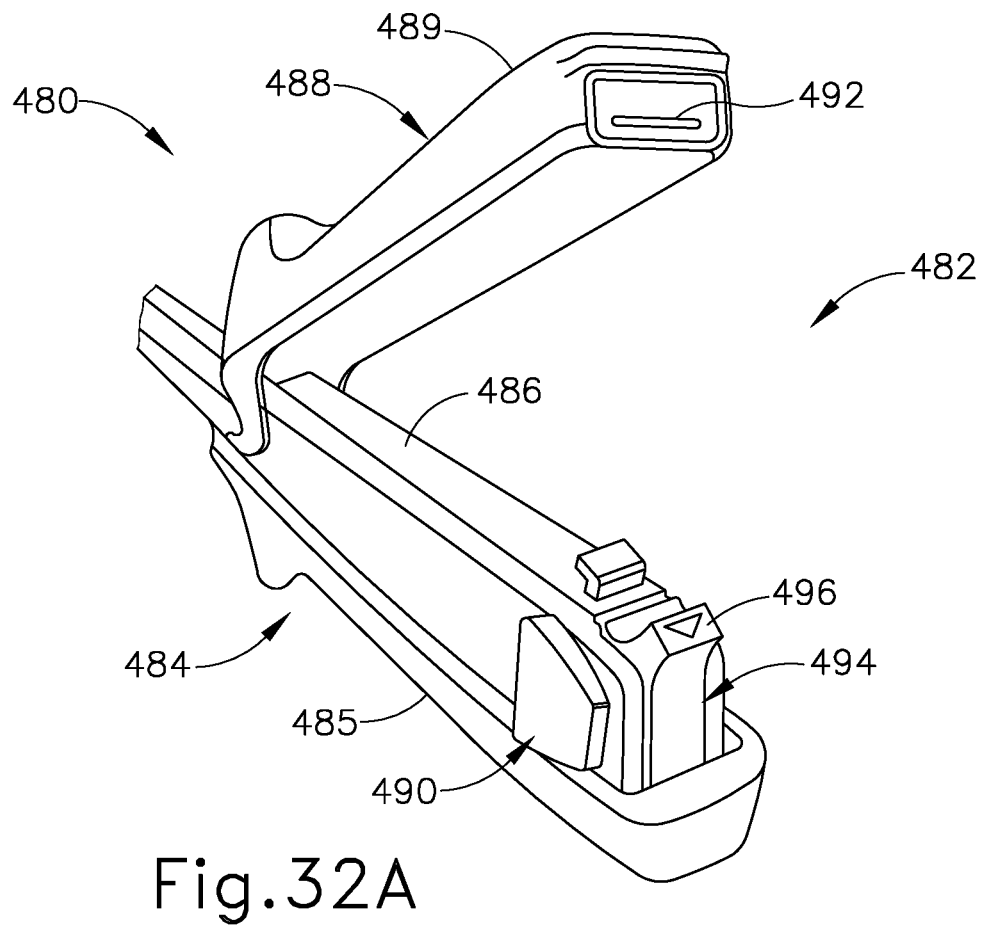
FIG. 32A depicts a proximal perspective view of another exemplary linear surgical stapler having a cartridge half and an anvil half, showing the clamp lever in an open position in which an anvil half release feature of the cartridge half is exposed for actuation to separate the stapler halves.
Figure 32B:
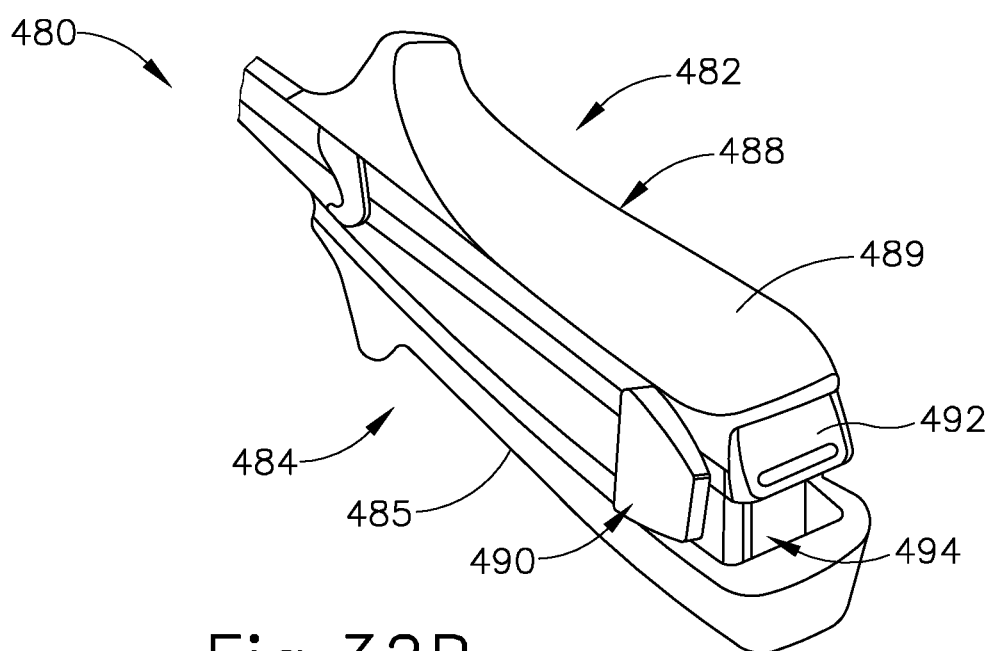
FIG. 32B depicts a proximal perspective view of the linear surgical stapler of FIG. 32, showing the clamp lever in a closed position in which a proximal end of the clamp lever covers the anvil half release feature to prevent its actuation.

A. Linear Surgical Stapler Having Anvil Release Feature Concealable Within Clamp Lever Shroud FIGS. 32A and 32B show an exemplary linear surgical stapler (480) that is similar to stapler (200) described above except as otherwise described below. Stapler (480) includes a cartridge half (482) and an anvil half (484) configured to releasably couple together to clamp tissue therebetween and simultaneously cut and staple the clamped tissue. Cartridge half (482) includes an elongate cartridge channel (486), a clamp lever (488) pivotably coupled to cartridge channel (486), and a firing assembly (490) slidably supported by cartridge channel (486). Clamp lever (488) includes a clamp lever latch member (492) configured to releasably maintain clamp lever (488) in the closed position. Clamp lever (488) includes a clamp lever shroud (489), and anvil half (484) includes an anvil shroud (485).

Cartridge half (482) further includes, among other features, an anvil latch member (494) configured to releasably couple a proximal end of cartridge half (482) with a proximal end of anvil half (484), similar to anvil latch member (302) described above. Anvil latch member (494) includes an anvil release button (496) exposed through a base wall of cartridge channel (486). Anvil release button (496) is actuatable by an operator to disengage anvil latch member (494) from anvil half (484) and thereby permit separation of stapler halves (482, 484). As shown, a proximal end of clamp lever shroud (489) is suitably shaped to conceal anvil release button (496) within an interior of shroud (489) when clamp lever (488) is in the closed position. Accordingly, an operator is prevented from unintentionally actuating anvil release button (496) before first actuating clamp lever latch member (492) to open clamp lever (488).

Figure 33A:
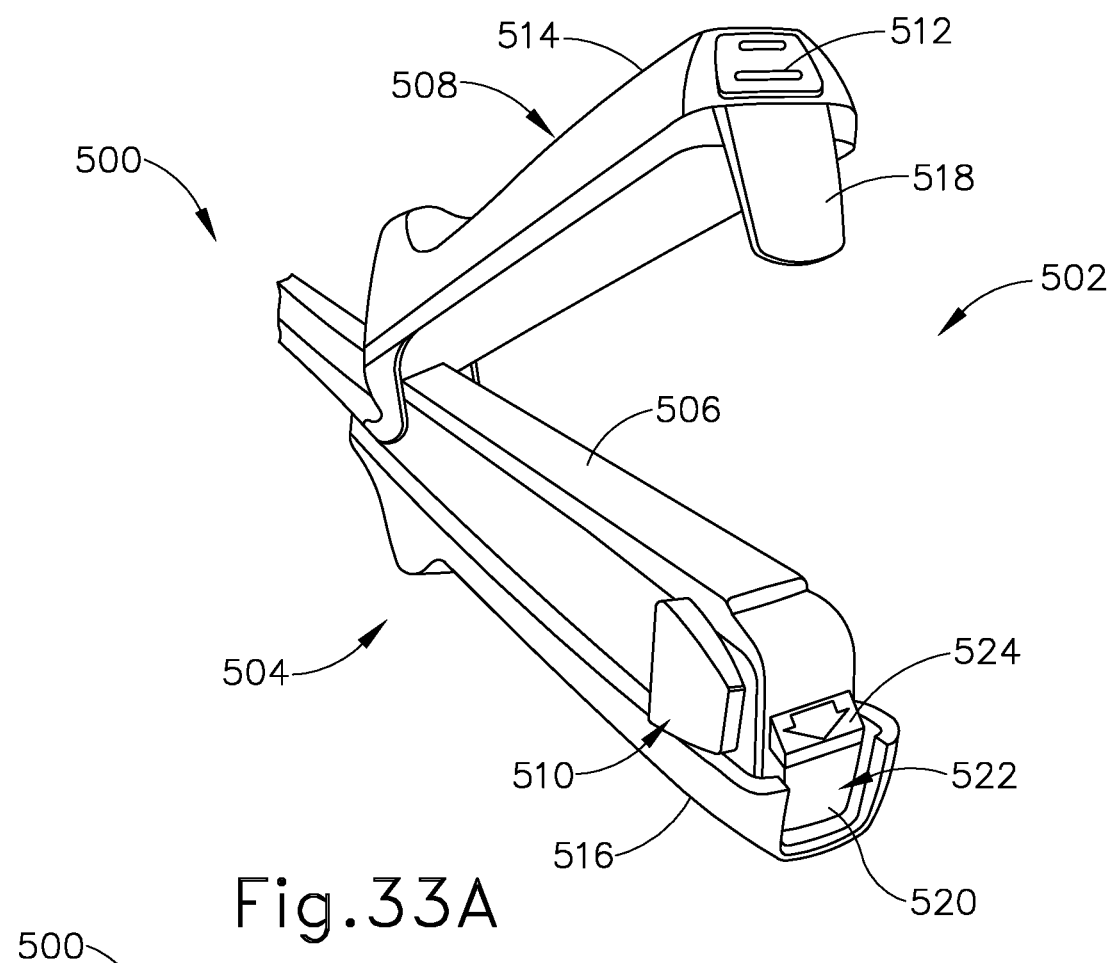
FIG. 33A depicts a proximal perspective view of another exemplary linear surgical stapler having a cartridge half and an anvil half, showing the clamp lever in an open position in which an anvil half release feature of the cartridge half is exposed for actuation to separate the stapler halves.
Figure 33B:
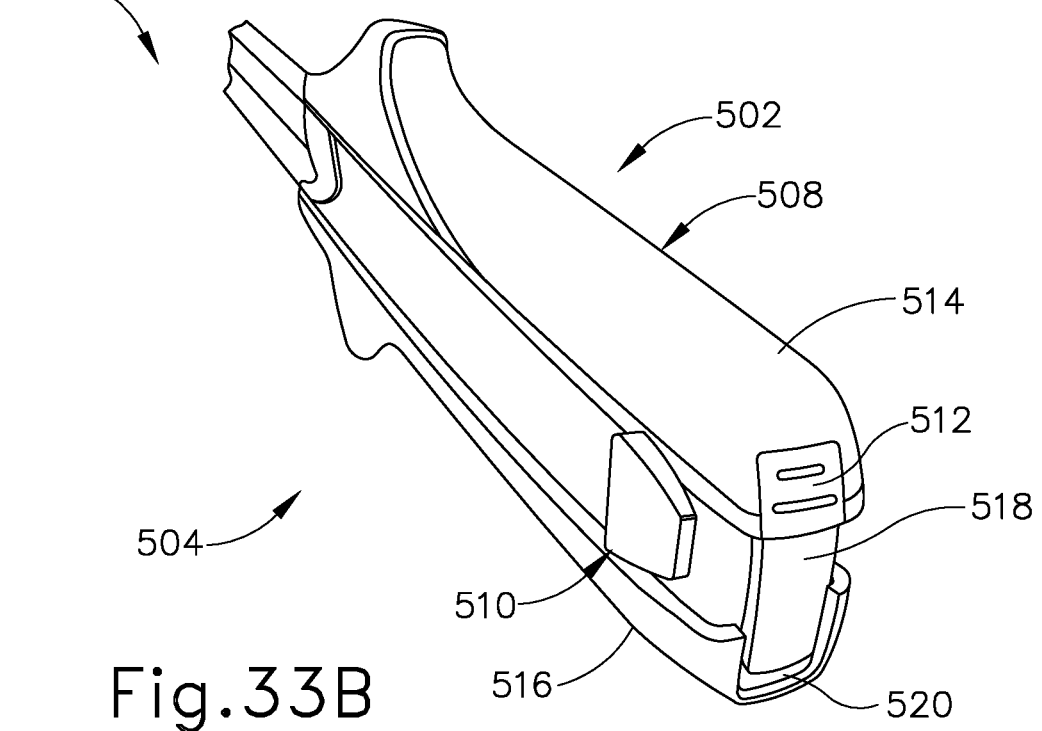
FIG. 33B depicts a proximal perspective view of the linear surgical stapler of FIG. 31, showing the clamp lever in a closed position in which a proximal end of the clamp lever covers the anvil half release feature to prevent its actuation.

B. Linear Surgical Stapler Having Anvil Release Feature Concealable by Tab of Clamp Lever Shroud FIGS. 33A and 33B show another exemplary linear surgical stapler (500) that is similar to stapler (480) described above except as otherwise described below. Stapler (500) includes a cartridge half (502) and an anvil half (504) configured to releasably couple together to clamp tissue therebetween and simultaneously cut and staple the clamped tissue. Cartridge half (502) includes an elongate cartridge channel (506), a clamp lever (508) pivotably coupled to cartridge channel (506), and a firing assembly (510) slidably supported by cartridge channel (506). Clamp lever (508) includes a clamp lever latch member (512) configured to releasably maintain clamp lever (508) in the closed position. Clamp lever (508) includes a clamp lever shroud (514), and anvil half (504) includes an anvil shroud (516). Clamp lever shroud (514) includes an elongate tab (518) arranged at a proximal end thereof and extending transversely toward a proximal end of anvil shroud (516). The proximal end of anvil shroud (516) includes a cutout (520) configured to receive a free end of tab (518) when clamp lever (508) is closed, as shown in FIG. 33B.

Cartridge half (502) further includes, among other features, an anvil latch member (522) configured to releasably couple a proximal end of cartridge half (502) with a proximal end of anvil half (504), similar to anvil latch member (494). Anvil latch member (522) includes an anvil release button (524) exposed through a proximal end of cartridge channel (506). Anvil release button (524) is actuatable by an operator to disengage anvil latch member (522) from anvil half (504) and thereby permit separation of stapler halves (502, 504). As shown, proximal tab (518) of clamp lever shroud (514) is configured to extend proximally about and thereby conceal anvil release button (524) when clamp lever (508) is in the closed position in which tab (518) is received within anvil shroud cutout (520). Accordingly, an operator is prevented from unintentionally actuating anvil release button (524) before first actuating clamp lever latch member (512) to open clamp lever (508).

In some versions, staplers (480, 500) may further include a clamp lever lockout feature (not shown) that prevents release of clamp lever latch member (492, 512) from cartridge channel (486, 506) until firing assembly (490, 510) has been returned to its proximal home position. In some versions, such a lockout feature may be configured similar to proximal hook (326) of detent member (304) described above.

VI. Exemplary Linear Surgical Stapler Having Pull-To-Fire Firing Assembly

Figure 34:
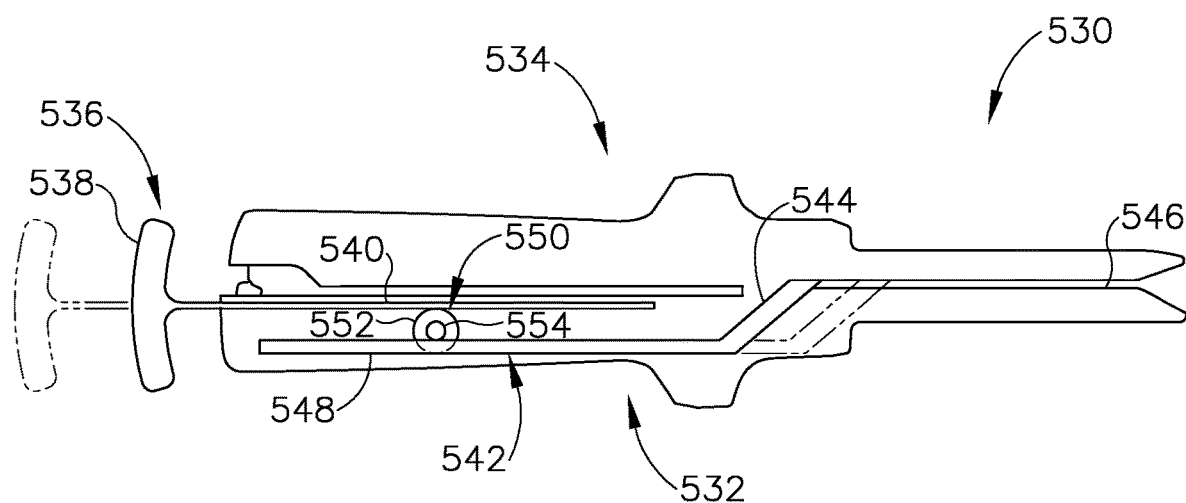
FIG. 34 depicts a schematic side view of another exemplary linear surgical stapler having an actuator configured to be pulled proximally to fire the stapler.
Figure 35:
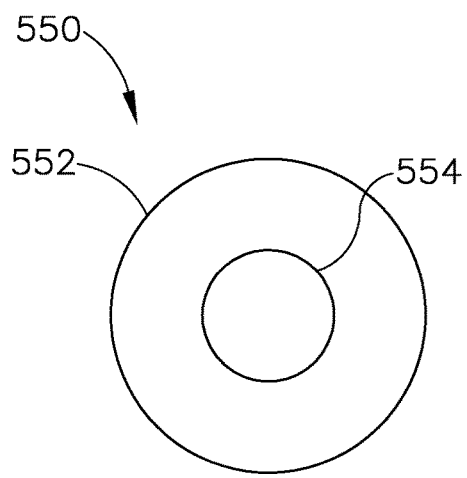
FIG. 35 depicts a schematic side view of a compound pinion gear of the linear surgical stapler of FIG. 34.
Figure 36:
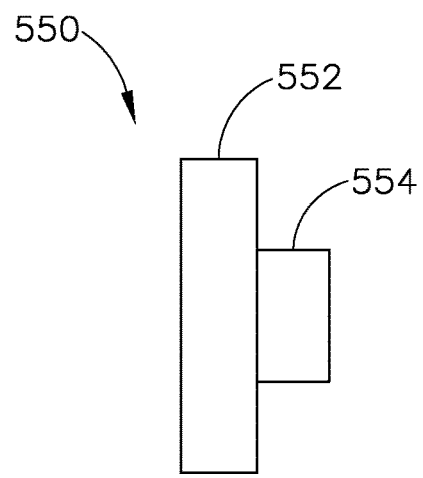
FIG. 36 depicts a schematic distal end view of the compound pinion gear of FIG. 35.

In many instances, it is desirable to configure a linear surgical stapler to minimize the input force required by an operator to fire the stapler. The exemplary linear surgical stapler (530) shown in FIG. 34 includes a firing assembly (536) that is fired by pulling an actuator (538) with a tension force rather than pushing actuator (538) with a compression force. As described in greater detail below, this "pull-to-fire" configuration provides enhanced mechanical advantage while maintaining dual-sided firing capability.

Linear surgical stapler (530) is similar to stapler (200) in that stapler (530) includes a cartridge half (532) and an anvil half (534) configured to releasably couple together to clamp tissue therebetween and simultaneously cut and staple the clamped tissue. Cartridge half (532) includes a firing assembly (536) having an actuator (538) (or "firing knob") arranged at the proximal end of stapler (530) and secured to the proximal end of an elongate drive beam (540). Drive beam (540) extends distally into cartridge half (532) and is in the form of a rack having a plurality of gear teeth (not shown) arranged on an underside thereof. Firing assembly (536) further includes an elongate firing beam (542) extending distally through cartridge half (532) and terminating at a distal knife member (544) configured to translate through a staple cartridge (546) to cut tissue. A proximal portion of firing beam (542) comprises a rack (548) having a plurality of gear teeth (not shown) arranged on an upper side thereof. Though not shown, firing beam (542) may further include one or more additional structures that provide cam ramps configured to actuate staple pushers (not shown) of staple cartridge (546), similar to side beams (358) and cam ramps (360) of stapler (200), for example.

Drive rack (540) and knife rack (548) are operatively coupled with one another via a compound pinion gear (550) rotatably mounted within cartridge half (532). Compound pinion gear (550) includes an outer gear portion (552) having a first diameter, and an inner gear portion (554) provided concentrically on a lateral face of outer gear portion (552) and having a smaller second diameter. Compound pinion gear (550) is mounted within cartridge half (532) such that outer gear portion engages drive rack (540) and inner gear portion (554) simultaneously engages knife rack (548), and such that pinion gear (550) is configured to rotate about an axis that extends transversely to a longitudinal axis of stapler (530).

To fire stapler (530), actuator (538) is pulled proximally by an operator from a distal home position to thereby translate drive rack (540) proximally. This causes compound pinion gear (550) to rotate in a first direction (e.g., counterclockwise in the view of FIG. 34), which drives firing beam (542) distally such that knife member (544) and cam ramps (not shown) are driven distally through staple cartridge (546) to thereby simultaneously cut and staple tissue clamped between stapler halves (532, 534). After reaching its fully proximal position, actuator (538) is then pushed distally to rotate compound pinion gear (550) in an opposite second direction (e.g., clockwise in the view of FIG. 34) and thereby retract firing beam (542) proximally to its home position.

The power transmission between racks (540, 548) and compound pinion gear (550) described above yields an output force at knife member (544) that is greater than the input force exerted on actuator (538) by the operator, thereby providing firing assembly (536) with mechanical advantage. It will be appreciated that outer and inner gear portions (552, 554) of compound pinion gear (550) may be suitably sized to provide firing assembly (536) with any desired degree of mechanical advantage during operation.

VII. Exemplary Attachment of Anvil Plate to Anvil Channel

As described above in connection linear surgical stapler (200), distal jaw portion (264) of anvil channel (260) supports an anvil surface (272) that provides a plurality of staple forming pockets. In some instances, it may be desirable to form anvil surface (272) separately from anvil channel (260) in the form of an anvil plate, and then rigidly attach the anvil plate to distal jaw portion (264). FIGS. 37A-39 show exemplary variations of such a process.

Figure 37A:
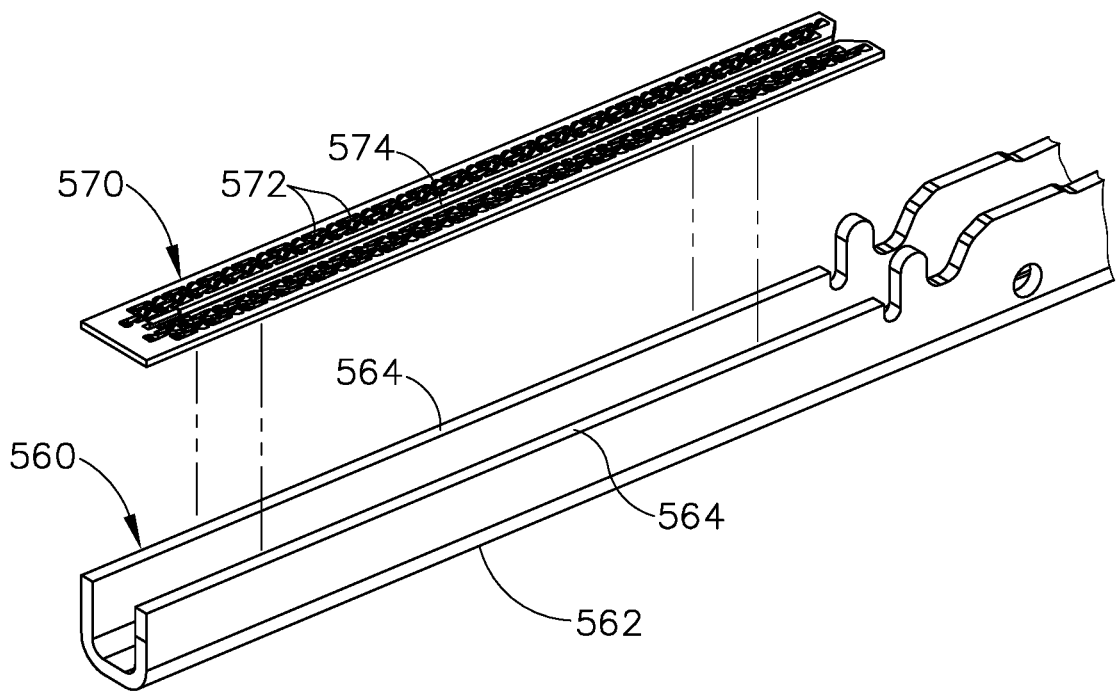
FIG. 37A depicts top perspective view of another exemplary anvil channel and a corresponding anvil plate, showing the anvil plate being aligned with a distal portion of the anvil channel during manufacturing.
Figure 37B:
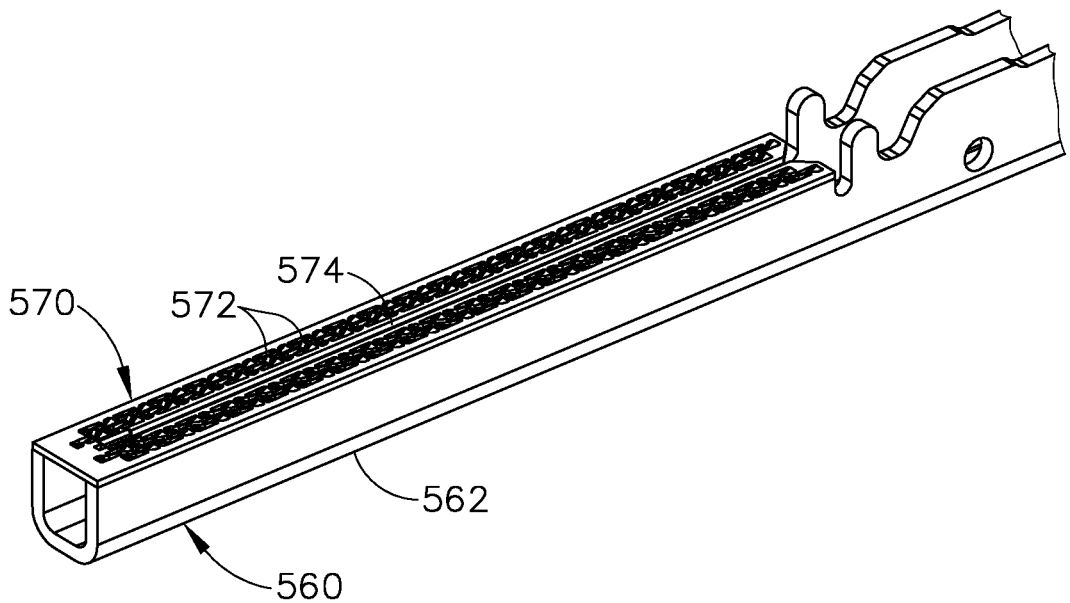
FIG. 37B depicts a top perspective view of the anvil channel and the anvil plate of FIG. 37A, showing the anvil plate mounted to the distal portion of the anvil channel.

FIGS. 37A and 37B show an anvil channel (560) having a distal jaw portion (562), and an anvil surface in the form of an anvil plate (570) formed separately from anvil channel (560). Anvil channel (560) may be similar to anvil channel (260) described above, and anvil channel (560) and anvil plate (570) are suitable for use with linear surgical stapler (200). Anvil plate (570) includes a plurality of staple forming pockets (572) and a longitudinal knife slot (574) configured to slidably receive a knife member (not shown) therethrough, which may be similar to knife member (366) described above. The features of anvil plate (570), including staple forming pockets (572) and longitudinal knife slot (574) may be formed via any one or more suitable machining processes, such as electrochemical machining (ECM) and/or coining, for example.

As shown in FIGS. 37A and 37B, after at least staple forming pockets (572) have been formed in anvil plate (570), a bottom surface of anvil plate (570) is aligned with and lowered onto side rails (564) of distal jaw portion (562) of anvil channel (560). Anvil plate (570) may be provided with one or more fiducial features during its machining process that aid in alignment of anvil plate (570) with anvil channel side rails (564). Such fiducial features may be in the form of, or alternatively may be provided in addition to, existing features of anvil plate (570). For instance, in some versions such fiducial features may comprise one or more of the bottom surface of anvil plate (570), longitudinal knife slot (574) or a select portion(s) of knife slot (574), or a proximal edge of anvil plate (570).

Figure 38:
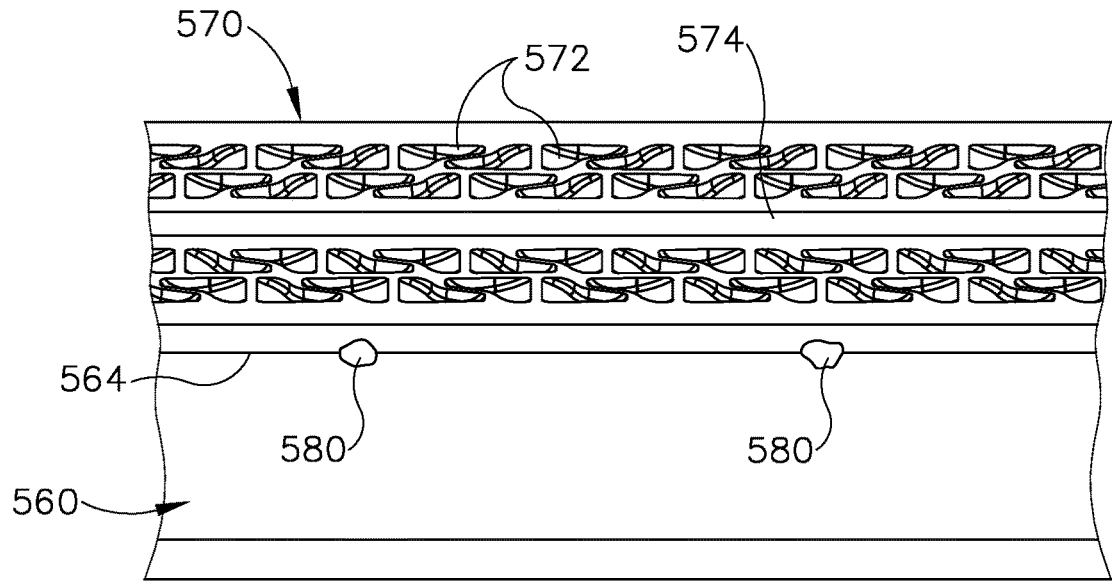
FIG. 38 depicts a side perspective view of the anvil channel and the anvil plate of FIG. 37A, showing the anvil plate affixed to the anvil channel in a first exemplary manner using spot welds.
Figure 39:
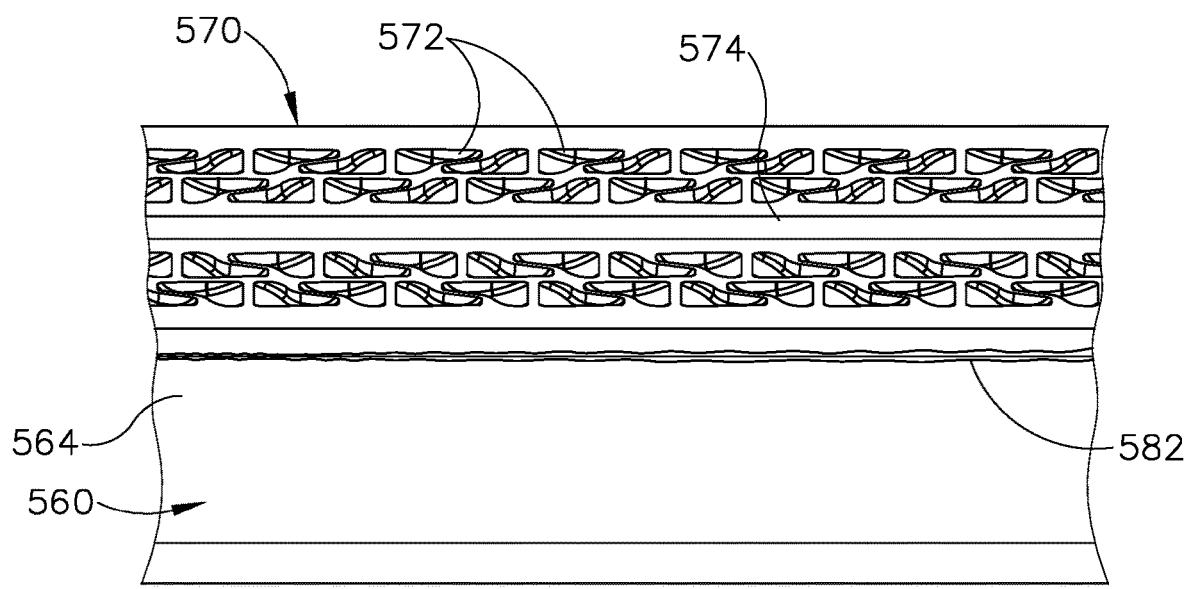
FIG. 39 depicts a side perspective view of the anvil channel and the anvil plate of FIG. 37A, showing the anvil plate affixed to the anvil channel in a second exemplary manner using seam welds.

Once anvil plate (570) is mounted to distal side rails (564) of anvil channel (560), anvil plate (570) is securely attached to side rails (564). FIG. 38 shows a first exemplary attachment method in which each lateral edge of anvil plate (570) is secured to the respective anvil channel side rail (564) with a plurality of spot welds (580) spaced longitudinally from one another. FIG. 39 shows a second exemplary attachment method in which each lateral edge of anvil plate (570) is secured to the respective anvil channel side rail (564) with a seam weld (582) that extends longitudinally for substantially a full length of anvil plate (570). In other versions, a plurality of shorter seam welds (582) may be provided along each lateral edge of anvil plate (570), or a combination of spot welds (580) and seam welds (582) may be provided. Furthermore, longitudinal knife slot (574) may be formed in anvil plate (570) before or after attachment of anvil plate (570) to anvil channel (560). It will be appreciated that forming pockets (572) in anvil plate (570) before anvil plate (570) is attached to anvil channel (560) advantageously reduces the size of the component being handled during the pocket formation process, thereby simplifying and reducing costs for manufacturing of the anvil half of a respective linear surgical stapler.

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a clamp member operable to releasably clamp the first elongate member against the second elongate member; (c) a firing assembly, wherein the firing assembly is translatable from a first longitudinal position to a second longitudinal position to fire the staple cartridge when the first elongate member is clamped against the second elongate member; and (d) a retaining assembly, wherein the retaining assembly comprises: (i) a first retaining member configured to releasably couple a proximal end of the first elongate member with a proximal end of the second elongate member, and (ii) a second retaining member configured to releasably retain the firing assembly in the first longitudinal position.

Example 2

The surgical stapler of Example 1, wherein the retaining assembly is arranged at a proximal end of the second elongate member.

Example 3

The surgical stapler of any of the preceding Examples, wherein the first retaining member is moveable relative to the second retaining member.

Example 4

The surgical stapler of any of the preceding Examples, wherein the first retaining member is configured to rotate in a first direction to release the proximal end of the first elongate member from the proximal end of the second elongate member, wherein the second retaining member is configured to rotate in a second direction to release the firing assembly from the first longitudinal position.

Example 5

The surgical stapler of Example 4, wherein the retaining assembly further comprises a resilient member configured to bias the first retaining member in the second direction and simultaneously bias the second retaining member in the first direction.

Example 6

The surgical stapler of any of the preceding Examples, wherein the first retaining member and the second retaining member are configured to rotate relative to the second elongate member channel about the same rotational axis.

Example 7

The surgical stapler of Example 6, wherein the rotational axis extends transversely to a longitudinal axis of the surgical stapler.

Example 8

The surgical stapler of any of the preceding Examples, wherein the first retaining member comprises a latch member, wherein the second retaining member comprises a detent member.

Example 9

The surgical stapler of Example 8, further comprising a projection arranged at a proximal end of the first elongate member, wherein the latch member is configured to releasably capture the projection to thereby couple the proximal end of the first elongate member with the proximal end of the second elongate member.

Example 10

The surgical stapler of Example 9, wherein the first elongate member is configured to pivot relative to the second elongate member about the projection when the proximal end of the first elongate member is coupled with the proximal end of the second elongate member.

Example 11

The surgical stapler of any of Examples 8 through 10, wherein the clamp member is moveable from an unclamped position to a clamped position to clamp the first elongate member against the second elongate member, wherein the retaining assembly further comprises a release feature operable to actuate the latch member to release the proximal end of the first elongate member from the proximal end of the second elongate member, wherein the release feature is exposed when the clamp member is in the unclamped position, wherein the release feature is concealed when the clamp member is in the clamped position.

Example 12

The surgical stapler of any of Examples 8 through 11, wherein the detent member includes a distally extending projection configured to releasably engage a proximal end of the firing assembly.

Example 13

The surgical stapler of any of Examples 8 through 12, wherein the clamp member is moveable from an unclamped position to a clamped position to clamp the first elongate member against the second elongate member, wherein the detent member is configured to prevent the clamp member from returning to the unclamped position from the clamped position when the firing assembly is advanced longitudinally away from its first longitudinal position.

Example 14

The surgical stapler of Example 13, wherein the detent member includes a lockout feature configured to engage a proximal feature of the clamp member to prevent the clamp member from returning to the unclamped position from the clamped position when the firing assembly is advanced longitudinally away from its first longitudinal position.

Example 15

The surgical stapler of Example 14, wherein the proximal feature of the clamp member comprises a second latch member, wherein the second latch member is operable to releasably couple a proximal end of the clamp member with the second elongate member when the clamp member is in the clamped position, wherein the lockout feature is operable to prevent the second latch member from disengaging the second elongate member when the firing assembly is advanced longitudinally away from its first longitudinal position.

Example 16

A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a clamp member operable to releasably clamp the first elongate member against the second elongate member; (d) a firing assembly, wherein the firing assembly is translatable from a first longitudinal position to a second longitudinal position to fire the staple cartridge when the first elongate member is clamped against the second elongate member; and (e) a retaining assembly arranged at a proximal end of the surgical stapler, wherein the retaining assembly comprises: (i) a latch member configured to releasably couple a proximal end of the first elongate member with a proximal end of the second elongate member, and (ii) a detent member configured to releasably retain the firing assembly in the first longitudinal position.

Example 17

The surgical stapler of Example 16, wherein the retaining assembly is rotatably coupled to a proximal end of the second elongate member.

Example 18

The surgical stapler of any of Examples 16 through 17, wherein the clamp member is movable from an unclamped position to a clamped position to clamp the first elongate member against the second elongate member, wherein the retaining assembly further comprises a release feature operable to actuate the latch member to release the proximal end of the first elongate member from the proximal end of the second elongate member, wherein the release feature is exposed when the clamp member is in the unclamped position, wherein the release feature is concealed when the clamp member is in the clamped position.

Example 19

A surgical stapler comprising: (a) a first elongate member having a distal portion that supports an anvil surface, wherein the anvil surface includes a plurality of staple forming pockets; (b) a second elongate member having a distal portion configured to receive a staple cartridge; (c) a clamp member operable to releasably clamp the first elongate member against the second elongate member; (d) a firing assembly, wherein the firing assembly is translatable from a first longitudinal position to a second longitudinal position to fire the staple cartridge when the first elongate member is clamped against the second elongate member; and (e) a retaining assembly, wherein the retaining assembly comprises: (i) a first moveable member configured to releasably couple a proximal end of the first elongate member with a proximal end of the second elongate member, and (ii) a second moveable member configured to releasably retain the firing assembly in the first longitudinal position, wherein the first moveable member and the second moveable member are moveable independently of one another.

Example 20

The surgical stapler of Example 19, wherein the first moveable member and the second moveable member are configured to rotate independently about the same rotational axis.

IX. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed on Feb. 6, 2018, issued as U.S. Pat. No. 10,631,866 on Apr. 28, 2020; U.S. application Ser. No. 15/889,370, entitled "Lockout Assembly for Linear Surgical Stapler," filed on Feb. 6, 2018, issued as U.S. Pat. No. 10,667,818 on Jun. 2, 2020; U.S. application Ser. No. 15/889,374, entitled "Features to Align and Close Linear Surgical Stapler"," filed on Feb. 6, 2018, published as U.S. Pub. No. 2019/0239886 on Aug. 8, 2019, issued as U.S. Pat. No. 10,932,781 on Mar. 2, 2021; U.S. application Ser. No. 15/889,376, entitled "Releasable Coupling Features for Proximal Portions of Linear Surgical Stapler," filed on Feb. 6, 2018, published as U.S. Pub. No. 2019/0239883 on Aug. 8, 2019, issued as U.S. Pat. No. 10,898,197 on Jan. 26, 2021; U.S. application Ser. No. 15/889,388, entitled "Firing Lever Assembly for Linear Surgical Stapler," filed on Feb. 6, 2018, published as U.S. Pub. No. 2019/0239884 on Aug. 8, 2019, issued as U.S. Pat. No. 10,874,398 on Dec. 29, 2020; and/or U.S. application Ser. No. 15/889,390, entitled "Clamping Mechanism for Linear Surgical Stapler," filed on Feb. 6, 2018, issued as U.S. Pat. No. 10,687,819 on Jun. 23, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
   (a) a first stapler portion having a first stapling surface;
   (b) a second stapler portion having a second stapling surface configured to cooperate with the first stapling surface to staple tissue;
   (c) a clamp member operable to releasably clamp the first stapler portion against the second stapler portion;
   (d) a firing assembly, wherein the firing assembly is translatable along a translational axis from a first longitudinal position to a second longitudinal position to fire staples into the tissue when the first stapler portion is clamped against the second stapler portion; and
   (e) a detent member rotatable about a rotational axis that is transverse to the translational axis, the detent member being configured to releasably retain the firing assembly in the first longitudinal position.

2. The surgical stapler of claim 1, the detent member including a central body and a stop tab, the stop tab being arranged on an outwardly facing lateral side of the central body.

3. The surgical stapler of claim 2, the stop tab being configured to abut a portion of the surgical stapler to thereby limit rotation of stop tab.

4. The surgical stapler of claim 2, the detent member being coupled with a spring, the spring being configured to rotationally bias the detent member such that the stop tab abuts the portion of the surgical stapler.

5. The surgical stapler of claim 4, the detent member further including a hook on a proximal portion of the detent member, wherein the stop tab is positioned on the proximal portion of the detent member, wherein the hook is configured to extend generally horizontally when the detent member is biased by the spring such that the stop tab is biased to abut the portion of the surgical stapler.

6. The surgical stapler of claim 1, the clamp member including a clamp lever latch member, the detent member including a hook, the detent member being rotatable such that the hook of the detent member is configured to hook over an upper tip of the clamp lever to thereby prevent the clamp lever from releasing a clamp.

7. The surgical stapler of claim 6, wherein the hook of the detent member is configured to hook over the upper tip of the clamp lever while the firing assembly is translating towards the second longitudinal position.

8. The surgical stapler of claim 6, wherein the hook of the detent member is configured to unhook from the upper tip of the clamp lever while the firing assembly is in the first longitudinal position to thereby allow clamp member to be released.

9. The surgical stapler of claim 1, wherein the detent member includes a distal finger and hook, wherein the distal finger is configured to interact with the firing assembly to thereby transition the hook between a hooked orientation and an unhooked orientation with the clamp member.

10. The surgical stapler of claim 9, wherein the detent member is coupled with a spring, wherein the spring is configured to bias the hook towards the hooked orientation.

11. A surgical stapler comprising:
   (a) a first stapler portion having a first stapling surface;
   (b) a second stapler portion having a second stapling surface configured to cooperate with the first stapling surface to staple tissue;
   (c) a clamp member operable to releasably clamp the first stapler portion against the second stapler portion, wherein the clamp member includes a latch member having a tip, the latch member being configured to releasably retain the clamp member in a clamped position;
   (d) a firing assembly, wherein the firing assembly is translatable from a first longitudinal position to a second longitudinal position to fire staples into the tissue when the first stapler portion is clamped against the second stapler portion; and
   (e) a detent member including a hook, wherein the detent member is rotatable, wherein the hook is configured to releasably capture the tip to thereby prevent the clamp member from unclamping the first stapler portion from the second stapler portion.

12. The surgical stapler of claim 11, wherein the hook is rotatably biased via a spring to thereby couple with the tip.

13. The surgical stapler of claim 11, wherein the hook is configured to prevent the latch member from rotating while the hook is coupled with the tip.

14. The surgical stapler of claim 13, wherein each of the detent member and the clamp member include an axis of rotation that are parallel to each other, wherein the hook and the tip are each configured to rotate away from each other about there respective axis of rotation to thereby release the first stapler portion from the second stapler portion.

15. The surgical stapler of claim 11, wherein the hook is configured to wrap around a portion of the tip.

16. The surgical stapler of claim 11, wherein the second stapler portion includes a stop notch at a proximal end, the detent member further including a stop tab configured to contact the stop notch to thereby limit a movement of the detent member relative to the second stapler portion.

17. The surgical stapler of claim 16, wherein the stop tab extends from a body of the detent member in a direction that is parallel to an axis of rotation of the detent member.

18. A method of using a surgical stapler, the surgical stapler including a first stapler portion, a second stapler portion, a clamp member, a firing assembly, and a detent member, the method comprising:
   (a) retaining the first and second stapler portions in a clamped state with the clamp member in a clamped position; and
   (b) in response to the firing assembly advancing from a proximal home position toward a distal fired position, rotating the detent member so that a hook of the detent member captures a portion of the clamp member and thereby inhibits the clamp member from transitioning to an unclamped position while the firing assembly is distal to the proximal home position.

19. The method of claim 18, the method further including wrapping a portion of the hook around a tip of a latch member of the clamp member during rotation of the hook.

20. The method of claim 18, the method further including limiting a rotation of the hook of the detent member relative to the second stapler portion via a stop tab of the detent member.

* * * * *